United States Patent [19]

Morishita et al.

[11] Patent Number: 5,409,895
[45] Date of Patent: Apr. 25, 1995

[54] PROTEASE INHIBITORY POLYPEPTIDES DERIVED FROM URINARY TRYPSIN INHIBITOR AND COMPOSITIONS THEREOF

[75] Inventors: Hideaki Morishita; Toshinori Kanamori; Masahiro Nobuhara, all of Tokyo, Japan

[73] Assignee: Mochida Pharmaceutical Co., Ltd., Tokyo, Japan

[21] Appl. No.: 791,213

[22] Filed: Nov. 13, 1991

[30] Foreign Application Priority Data

Nov. 13, 1990 [JP] Japan .................. 2-306745

[51] Int. Cl.⁶ .................. A61K 37/64; C07K 7/10
[52] U.S. Cl. .................. 514/12; 530/324; 435/69.2
[58] Field of Search .................. 424/94.1; 514/2, 12, 514/822, 825, 838, 870; 530/324

[56] References Cited

U.S. PATENT DOCUMENTS 4,894,436 1/1990 Auerswald et al. .................. 530/324

FOREIGN PATENT DOCUMENTS 0073251 3/1982 European Pat. Off. .
0255011 3/1988 European Pat. Off. .
0401508 12/1990 European Pat. Off. .
3-59079 9/1991 Japan .

OTHER PUBLICATIONS

Lau, P. et al.: Proteolytic Degradation of Human Recombinant Proinsulin/Insulin by Sera from Acute Pancreatitis Patients and Complete Inhibition by Eglin C. Pancreas 5:17–26 (1990).
Hochstrasser et al., Hoppe-Seyler's Z. Physiol. Chem. 360: 1285–1296 (1979).
Hirano et al., Digestive Dis. Sci. 38:660–664 (1993).
Lau et al.,; Pancreas 5:17–26 (1990).
Hiroshi Kido et al, "Kunitz-type Protease Inhibitor Found in Rat Mast Cells", The Journal of Biological Chemistry, vol. 263, No. 34, pp. 18104–18107, 1988.
Wallace L. McKeehan et al., The Journal of Biological Chemistry, vol. 261, No. 12 (Apr., 1986), pp. 5378–5383, "Two Apparent Endothelial Cell Growth Factors from Human Hepatoma Cells are Tumor-Associated Proteinase Inhibitors".
Kenji Yoshida et al., Nippon Rinsho, vol. 48, No. 1 (1990), pp. 165–172, "Antienzyme preparations in the treatment of acute pancreatitis".
G. J. Proksch et al., J. Lab. Clin. Med., vol. 79, No. 3 (1972), pp. 491–499, "The purification of the trypsin inhibitor from human pregnancy urine".
Hiroyuki Sumi et al., J. Physiol. Soc. Japan, vol. 39 (1977), pp. 53–58, "Trypsin inhibitors in human urine".
J. Bourguignon et al., Biochemical and Biophysical Research Communications, vol. 131, No. 3 (1985), pp. 1146–1153, "Human Inter-Alpha-Typsin-Inhibitor: Characterization and Partial Nucleotide Sequencing of a Light Chain-Encoding cDNA".
Hiroyuki Sumi et al., Blood & Vessel, vol. 19 (1988), pp. 545–557, "Structure, function and distribution of acid-stable trypsin-plasmin inhibitors (urinary trypsin inhibitor related substances)".

(List continued on next page.)

Primary Examiner—Robert A. Wax
Assistant Examiner—Eric Grimes
Attorney, Agent, or Firm—Burns, Doane, Swecker & Mathis

[57] ABSTRACT

This invention provides a novel polypeptide which comprises an amino acid sequence that constitutes a portion of urinary trypsin inhibitor (UTI) and which has no antigenicity against human and high activity to inhibit various proteases, as well as other novel polypeptides having excellent activities to inhibit various proteases obtained by mutation of the former novel polypeptide. This invention also provides novel enzyme inhibition processes, drug compositions and treating methods making use of the novel polypeptide, DNA fragments containing nucleotide sequences which encode the novel polypeptides, vectors containing the DNA fragments and transformants transformed with the DNA fragments or the vectors, as well as processes for the production of the novel polypeptides.

10 Claims, 34 Drawing Sheets

OTHER PUBLICATIONS

Tadahiro Shikimi, *Pharma Medica*, vol. 7, No. 11 (1989) pp. 169–174, "Biochemical background of human urinary trypsin inhibitor, urinastatin".

Haruo Ohnishi et al., *Folia Pharmacol.*, Japan, vol. 81 (1983), pp. 235–244, "Therapeutic effects of human urinary trypsin inhibitor on acute experimental pancreatitis".

Karl Hochstrasser et al., *Hoppe-Seyler's Z. Physiol. Chem.*, vol. 364 (1983), pp. 1689–1696, "Kunitz-Type Proteinase Inhibitors Derived by Limited Proteolysis of the Inter-Alpha-Trypsin Inhibitor, VIII[1-7]".

*Chemical Abstracts* 100(15): 117045t, Sumi et al., "Enzymic modification of fibrinolytic and antifibrinolytic components," 1984, p. 246.

Albrecht, et al., "Elastase Inhibition by the Inter-α-Trypsin Inhibitor and Derived Inhibitors . . . ," Hoppe-Seyler's Z. Physiol. Chem., Bd. 364, Dec. 1983, pp. 1703–1708.

Wachter, et al., "Kunitz-Type Proteinase Inhibitors Derived by Limited Proteolysis . . ." IV[1-3], Hoppe-Seyler's Z. Physiol. Chem., Bd. 362, Oct. 1981, pp. 1351–1355.

Reisinger, et al., "Human Inter-α-Trypsin Inhibitor: Localization of the Kunitz-Type Domains in the . . . ," Biol. Chemistry Hoppe-Seyler, vol. 366, pp. 479–483, May 1985.

Kaumeyer, et al., "The mRNA for a proteinase inhibitor related to the HI-30 domain of inter-alpha-trypsin . . . ," Nucleic Acids Research, vol. 14 No. 20, 1986, pp. 7839–7848.

Sakuragawa et al., "Effect of urinastatin on coagulation, fibrinolysis, and platelet, aggregation . . . ," Abstract No. 107:228724c, Chemical Abstracts, vol. 107, 1987, p. 46.

Sakuragawa et al., Saishin Igaku (Current Medicine), vol. 42, 1987, pp. 820–830.

Fukutake et al., Folia pharmacol. Japan, vol. 90, 1987, pp. 163–169.

S33

5'  AGCTTAAAAA AGGGTATAAA ATAAAATGAA AC
         ATTTTT TCCCATATTT TATTTTACTT TGTTTCATGA  5'
                                                  S34

S35

5'  AAAGTACTAT TGCACTGGCA CTCTTACCGT TACTGTTT
            TA ACGTGACCGT GAGAATGGCA ATGACAAA TGGGGA  5'
                                                      S18

S19
5'  ACCCCTGTGA CAAAAGCCGA CTCCCTAGGT CG
           CACT GTTTTCGGCT GAGGGATCCA GC  5'
                                          S20

FIG. 1

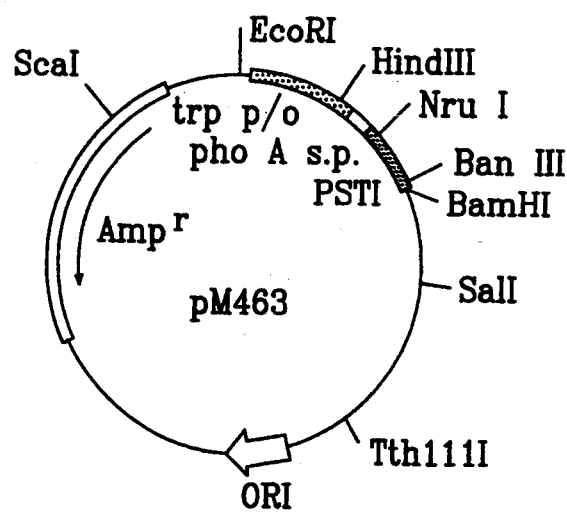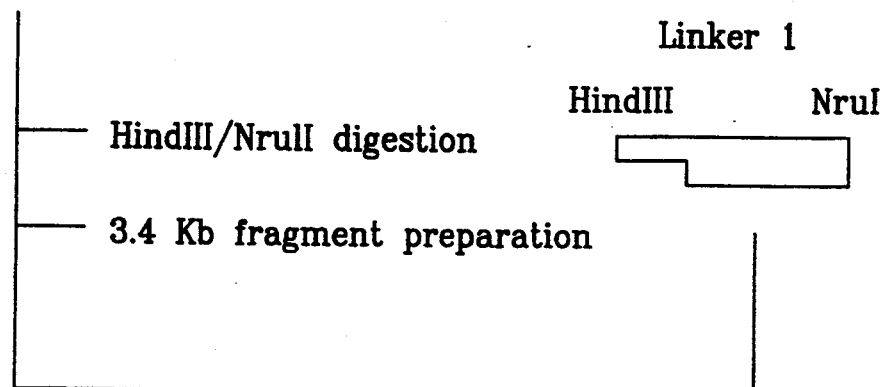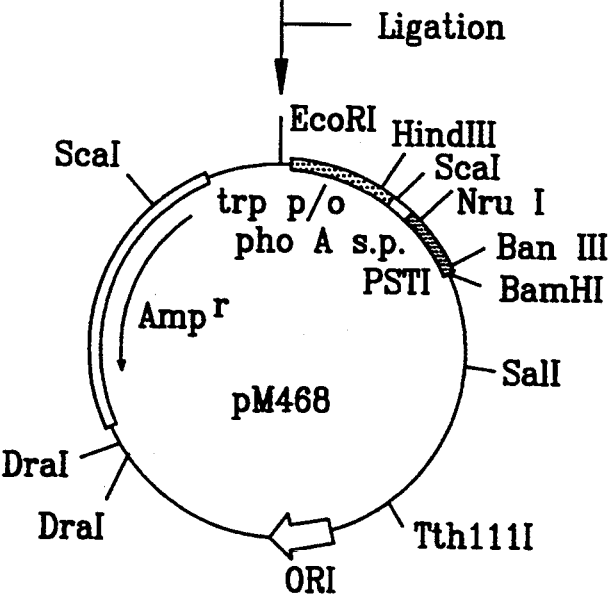
FIG. 2 p-s01    5'   TTGGCCACC GTC GCC GCC TGC AAC CTG CC
              Eae I                 T   T   C

_____ ∨ _____/

FIG. 4A p-a01    5'   TGGATCCAGTTG TCA GTT GGA GAA GC
              BamHI

Linker 2

5' ACTATTGCAC TGGCACTCTT ACCGTTACTG TTTACCCCTG TGACAAA
   TGATAACGTG ACCGTGAGAA TGGCAATGAC AAATGGGGAC ACTGTTT CCGG 5'

Linker 3

FIG. 5

```
                                    -20              -15              -10
5'-AAGCTTAAAAAGGGTATAAATAAA ATG AAA CAA AGT ACT ATT GCA CTG GCA CTC TTA CCG
   Hind III                  Met Lys Gln Ser Thr Ile Ala Leu Ala Leu Leu Pro
                                    phoA signal peptide
                  -5                           -1  1         5                T  C  G        10
        5'-TTG GCC ACC GTC GCC GCC GCC TTC AAT CTC CC-3'
        5'-TTG GCC ACC GTC ACA AAG GCC GTC GCC GCC TGC AAT CTC CCC ATA GTC
                                p-s01
           Leu Leu Phe Thr Pro Val Thr Lys Ala│Thr Val Ala Ala Cys Asn Leu Pro Ile Val
                                              polypeptide TN70
                  15                  20                  25
TTA CTG TTT ACC CCT GTG ACA AAG GCC GTC GCC GCC TGC AAT CTC CCC ATA GTC
Leu Leu Phe Thr Pro Val Thr Lys Ala Thr Val Ala Ala Cys Asn Leu Pro Ile Val 30                  35                  40                  45
CGG GGC CCC TGC CGA GCC TTC ATC CAG CTC TGG GCA TTT GAT GCT GTC AAG GGG AAG
Arg Gly Pro Cys Arg Ala Phe Ile Gln Leu Trp Ala Phe Asp Ala Val Lys Gly Lys 50                  55                  60                  65
TGC GTC CTC TTC CCC TAC GGG GGC TGC CAG GGC AAC GGG AAC AAG TTC TAC TCA GAG
Cys Val Leu Phe Pro Tyr Gly Gly Cys Gln Gly Asn Gly Asn Lys Phe Tyr Ser Glu 70
AAG GAG TGC AGA GAG TAC TGC TGC GGT GTC CCT GGT GAT GGT GAT GAG GAG CTG CGC
Lys Glu Cys Arg Glu Tyr Cys Cys Gly Val Pro Gly Asp Gly Asp Glu Glu Leu Leu Arg 3'-CG
TTC TCC AAC TGA CAACTGGATCC-3'
Phe Ser Asn ***      BamHI AAG AGG TTG ACT GTTGACCTAGGT-5'
        p-a01
```

FIG. 7

ScaI sense primer    5' ACT ATT GCA CTG GCA CTC TTA 3'

FIG. 8A p-ao2    5' TGGATCCTA GCA GTA CTC TCT GCA CTC CTT 3'

FIG. 8B

HindIII sense primer    5' ACGCAAGTTCACGTAAAAAGC 3'

FIG. 9A p-ao3    5' AT GGG GAG ATT GCA GGC CTT TGT CAC AG 3'

FIG. 9B

BamHI antisense primer    5' ACGATGCGTTCCGGGCGTAGAG 3'

HindIII sense primer
5'-ACGCAAGTTCACGTAAAAGC-3'
5'-ACGCAAGTTCACGTAAAAAGCTTAAAAAAGGGTATAAATAAA ATG AAA CAA AGT ACT ATT
                       HindIII                              Met Lys Gln Ser Thr Ile
                                                            phoA signal peptide
                              -20                                   -5         -1  1

5'-ACT ATT

ScaI sense primer
5'-GCA CTG GCA CTC TTA-3'
GCA CTG GCA CTC TTA CCG TTA CTG TTT ACC CCT GTG ACA AAG GCC | TGC AAT
Ala Leu Ala Leu Leu Pro Leu Leu Phe Thr Pro Val Thr Lys Ala | Cys Asn
                                                              p-a03
       -10                   -5                                   -1  1

3'-GA CAC TGT TTC CGG ACG TTA
                                                         polypeptide CC51
                                                                      15

CTC CCC ATA GTC CGG GGC CCC TGC CGA GCC TTC ATC CAG CTC TGG GCA TTT
Leu Pro Ile Val Arg Gly Pro Cys Arg Ala Phe Ile Gln Leu Trp Ala Phe
        5              10                    15

GAG GGG TA-5'
    20

GAT GCT GTC AAG GGG AAG TGC GTC CTC TTC CCC TAC GGG GGC TGC CAG GGC
Asp Ala Val Lys Gly Lys Cys Val Leu Phe Pro Tyr Gly Gly Cys Gln Gly
            25                     30                     35

3'-TTC CTC ACG TCT CTC ATG ACG AT
                                                      p-a02

AAC GGG AAC AAG TTC TAC TCA GAG AAG GAG TGC AGA GAG TAC TGC TA
Asn Gly Asn Lys Phe Tyr Ser Glu Lys Glu Cys Arg Glu Tyr Cys ..
        40                     45                     50

BamHI
GGATCCTCTACGCCGGAACGCATCGT-3'
 3'-GAGATGCGGCCTTGCGTAGCA-5'
CCTAGGT-5'  BamHI antisense primer p-a04   5' TGGATCCTA CAG CAG CAG CTC CTC CTC ATC ATC ACC ATC 3'

FIG. 12

```
5'- AAGCTTAAAAAAGGGTATAAAATAAA ATG AAA CAA AGT ACT ATT GCA CTG GCA CTC TTA CCG
    HindIII                    Met Lys Gln Ser Thr Ile Ala Leu Ala Leu Leu Pro
                                                 phoA signal peptide
                                        -1 1              p-s01       T   C   G
                              5'- TTG GCC ACC GTC GCC GCC TGC AAT CTC CC-3'

TTA CTG TTT ACC CCT GTG ACA AAG GCC ACC GTC GCC GCC TGC AAT CTC CCC ATA GTC
Leu Leu Phe Thr Pro Val Thr Lys Ala │Thr Val Ala Ala Cys Asn Leu Pro Ile Val
                                    └── polypeptide TL86

CGG GGC CCC TGC CGA GCC TTC ATC CAG CTC TGG GCA TTT GAT GCT GTC AAG GGG AAG
Arg Gly Pro Cys Arg Ala Phe Ile Gln Leu Trp Ala Phe Asp Ala Val Lys Gly Lys

TGC GTC CTC TTC CCC TAC GGG GGC TGC CAG GGC AAC AAG TTC TAC TCA GAG
Cys Val Leu Phe Pro Tyr Gly Gly Cys Gln Gly Asn Lys Phe Tyr Ser Glu

AAG GAG TGC AGA GAG TAC TGC GGT GTC CCT GGT GAT GGT GAT GAG GAG CTG
Lys Glu Cys Arg Glu Tyr Cys Gly Val Pro Gly Asp Gly Asp Glu Glu Leu Leu
                                    3'-CTA CCA CTA CTC CTC GAC GAC
                                                 p-a04
  BamHI
  TAGGATCC-3'
  ***
  ATCCTAGGT-5'
```

FIG. 13

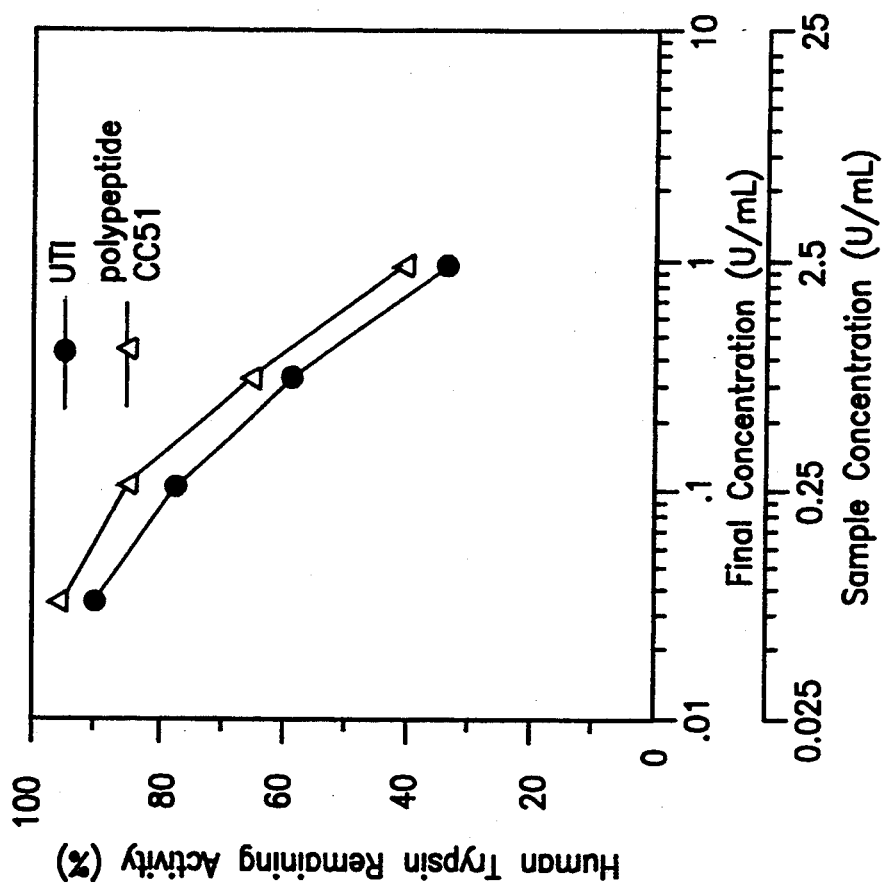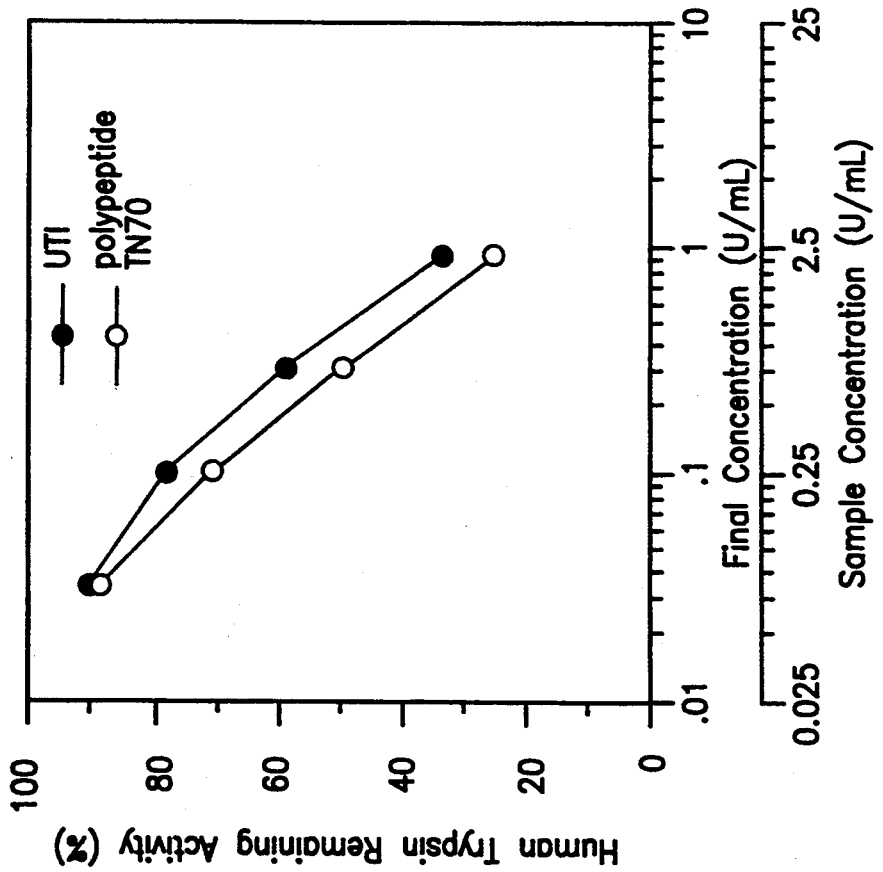

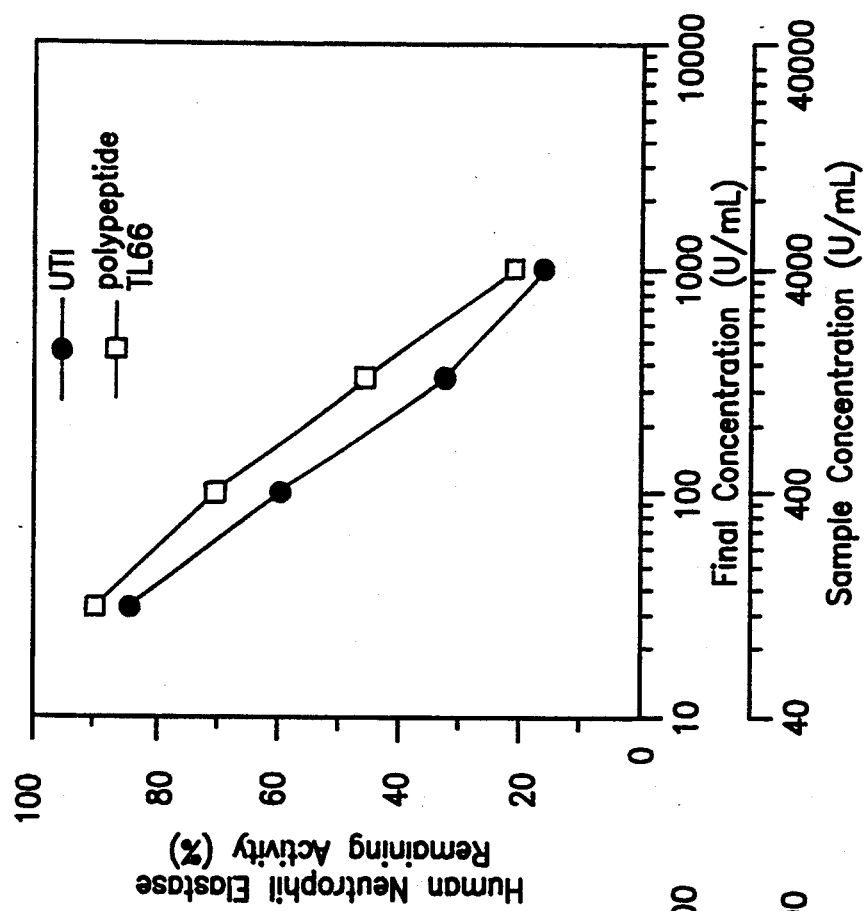
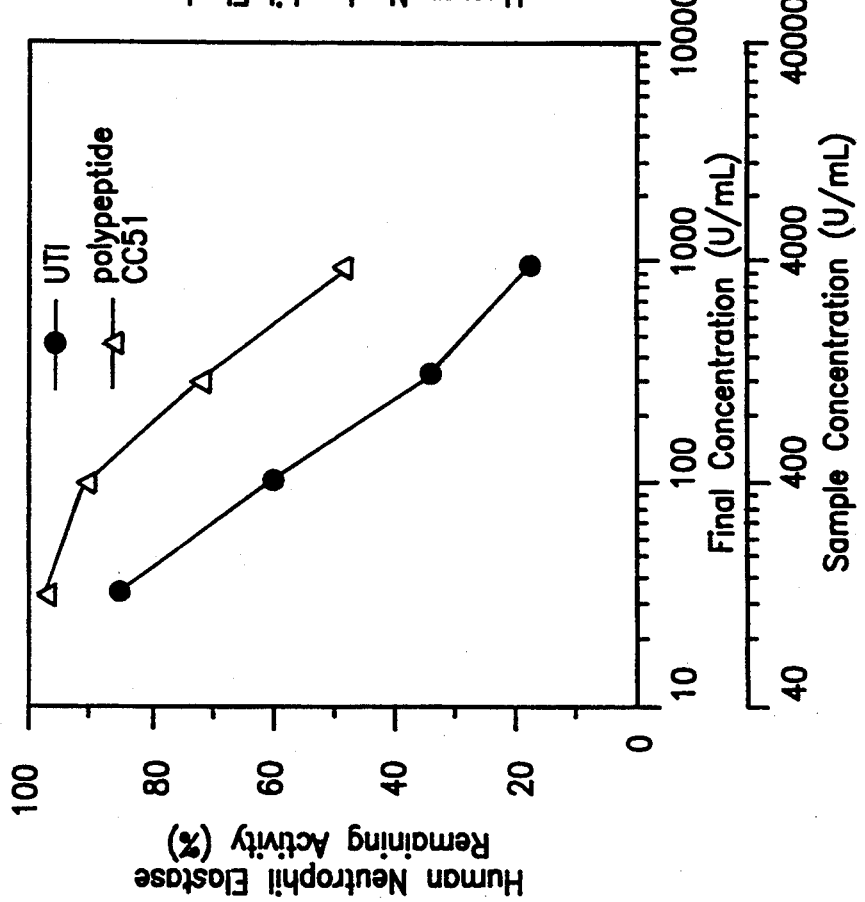
FIG. 15C
FIG. 15B

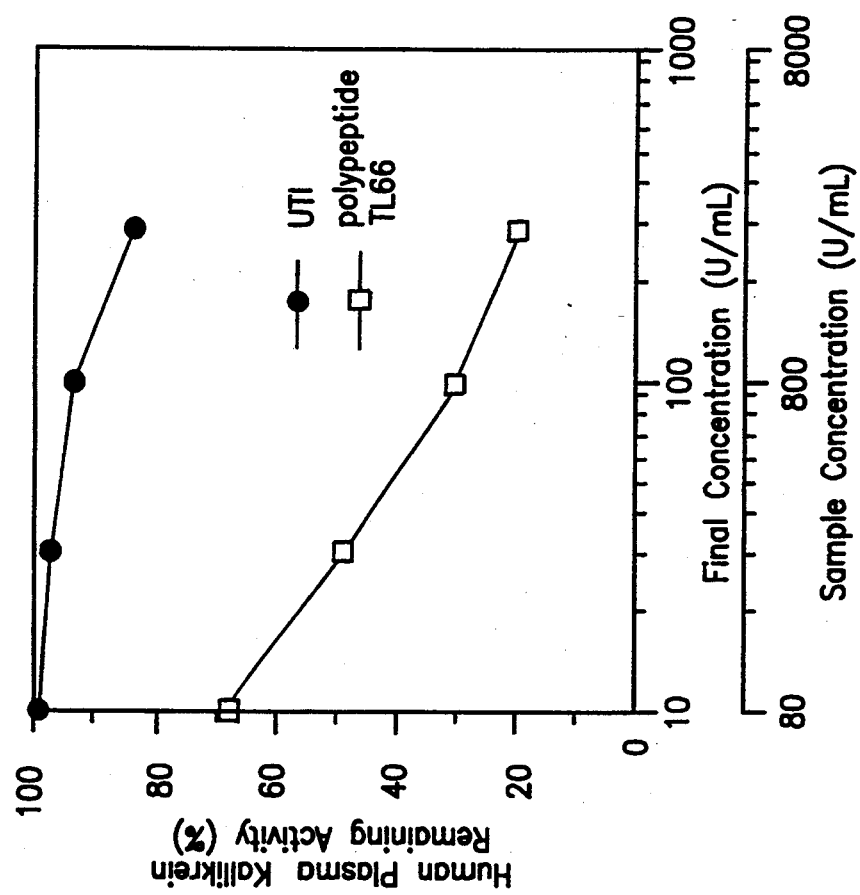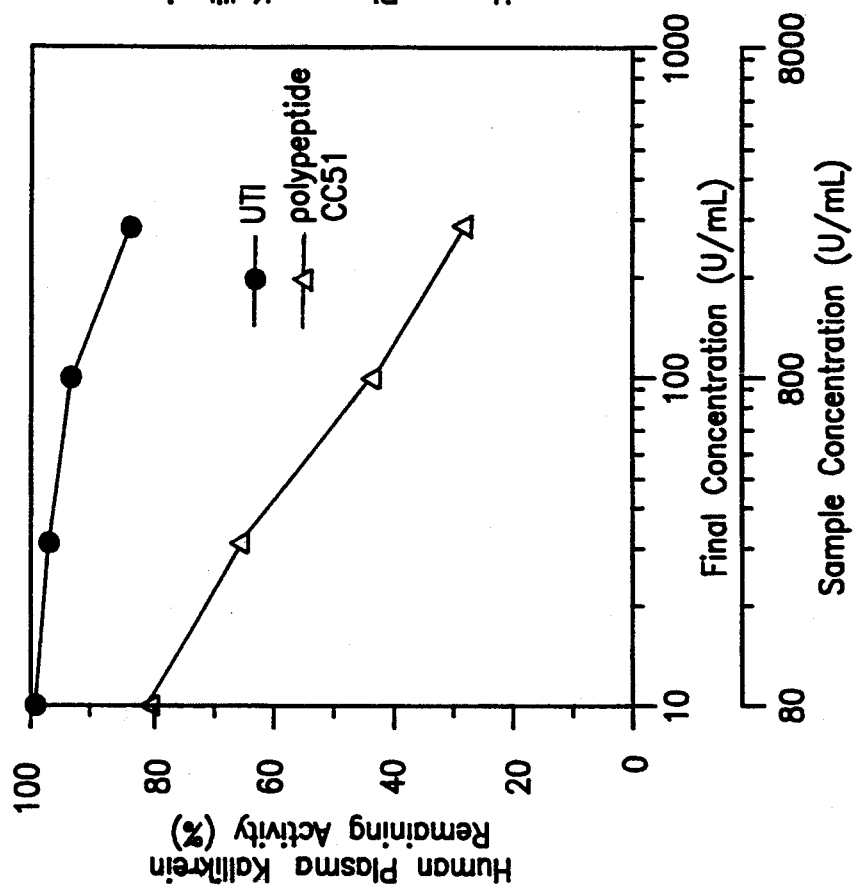

Oligomer Y46E     5' GG AAC AAG TTC GAA TCA GAG AAG GA 3'

```
                                               -10
                             -15      ScaI sense primer
         -20                        5'- ACT ATT GCA CTG GCA CTC TTA-3'
5'-AAGCTTAAAAAAGGGTATAAATAAA ATG AAA CAA AGT ACT ATT GCA CTG GCA CTC TTA CCG
   HindIII                  Met Lys Gln Ser Thr Ile Ala Leu Ala Leu Leu Pro
                                      phoA signal peptide
           -5              -1   1                         5                10
TTA CTG TTT ACC CCT GTG ACA AAG GCC|ACC GTC GCC GCC TGC AAT CTC CCC ATA GTC
Leu Leu Phe Thr Pro Val Thr Lys Ala|Thr Val Ala Ala Cys Asn Leu Pro Ile Val
                                        polypeptide Y46E
              15                  20                  25
CGG GGC CCC TGC CGA GCC TTC ATC CAG CTC TGG GCA TTT GAT GCT GTC AAG GGG AAG
Arg Gly Pro Cys Arg Ala Phe Ile Gln Leu Trp Ala Phe Asp Ala Val Lys Gly Lys
30                  35                  40                  45
                                                        Oligomer Y46E
                                           5'-GG AAC AAG TTC GAA TCA GAG
TGC GTC CTC TTC CCC TAC GGG GGC TGC CAG GGC AAC AAG TTC GAA TCA GAG
Cys Val Leu Phe Pro Tyr Gly Gly Cys Gln Gly Asn Lys Phe Glu Ser Glu
            50                  55                  60                  65
AAG GA-3'
AAG GAG TGC AGA GAG TAC TGC GGT GTC CCT GGT GAT GGT GAC GAG GAG CTG CTG CGC
Lys Glu Cys Arg Glu Tyr Cys Gly Val Pro Gly Asp Gly Asp Glu Glu Leu Leu Arg
                                                                      3'-CG
          BamHI
TTC TCC AAC TGA CAACTGGATCC
Phe Ser Asn ...
AAG AGG TTG ACT GTTGACCTAGGT-5'
p-e01
```

FIG. 21

Oligomer TV12DD 5' TG ACA AAG GCC GAC GAC GCC GCC TGC AA 3' p-a05    5' C AAA TGC CCA GAG CTT GAT GAA GGC TCG GCA 3'

```
                                                                          -20
         HindIII sense primer
5' - ACGCAAGTTCACGTAAAAAGC-3'                                                                    5'- ACT ATT
5' -ACGCAAGTTCACGTAAAAAGCTTAAAAAGGGTATAAAAATAAA ATG AAA CAA AGT ACT ATT
         HindIII                                                 Met Lys Gln Ser Thr Ile
                                                                 phoA signal peptide
  -15                     -10                     -5
ScaI sense primer                                        Oligomer TV12DD            1
                                                    5'-TG ACA AAG GCC GAC GAC
GCA CTG GCA CTC TTA-3'
GCA CTG GCA CTC TTA CCG TTA CTG TTT ACC CCT GTG ACA AAG GCC GAC GAC
Ala Leu Ala Leu Leu Pro Leu Leu Phe Thr Pro Val Thr Lys Ala | Asp Asp
                     5                      10                  15
GCC GCC TGC AA-3'
GCC GCC TGC AAT CTC CCC ATA GTC CGG GGC CCC TGC CGA GCC TTC ATC AAG
Ala Ala Cys Asn Leu Pro Ile Val Arg Gly Pro Cys Arg Ala Phe Ile Lys
polypeptide Q19K                                  3'-ACG GCT CGG AAG TAG TTC
                                                                  p-a05
                     25                     30                     35
CTC TGG GCA TTT GAT GCT GTC AAG GGG AAG TGC GTC CTC TTC CCC TAC GGG
Leu Trp Ala Phe Asp Ala Val Lys Gly Lys Cys Val Leu Phe Pro Tyr Gly
GAG ACC CGT AAA C-5'
                     40                     45                     50
GGC TGC CAG GGC AAC GGG AAC AAG TTC TAC TCA GAG AAG TGC AGA GAG
Gly Cys Gln Gly Asn Gly Asn Lys Phe Tyr Ser Glu Lys Cys Arg Glu
                     55                     60                     65                   70
TAC TGC GGT GTC CCT GGT GAT GAG GAG CTG CGC TTC TCC AAC
Tyr Cys Gly Val Pro Gly Asp Glu Glu Leu Arg Phe Ser Asn
              BamHI
TGA CAACTGGATCCTCTACGCCGGAACGCATCGT-3'
   3'-GAGATGCGGCCCTTGCGTAGCA-5'
     BamHI antisense primer

FIG. 24
``` p-a06  5' TGG ATC CTA GTA CTC TCT GCA CTC CTT CT 3'

HindIII sense primer
5'-ACGCAAGTTCACGTAAAAGC-3'

5'-ACGCAAGTTCACGTAAAAGCTTAAAAAGGGTATAAATAAA ATG AAA CAA AGT ACT ATT
                     HindIII                                -20
                                                Met Lys Gln Ser Thr Ile
                                                phoA signal peptide

```
-15                    -10                  -5                   -1  1
GCA CTG GCA CTC TTA CCG TTA CTG TTT ACC CCT GTG ACA AAG GCC|ACC GTC
Ala Leu Ala Leu Leu Pro Leu Leu Phe Thr Pro Val Thr Lys Ala|Thr Val 5                    10                  15
GCC GCC TGC AAT CTC CCC ATA GTC CGG GGC CCC TGC CGA GCC TTC ATC CAG
Ala Ala Cys Asn Leu Pro Ile Val Arg Gly Pro Cys Arg Ala Phe Ile Gln
polypeptide TY54

20                  25                  30                  35
CTC TGG GCA TTT GAT GCT GTC AAG GGG AAC TGC GTC CTC TTC CCC TAC GGG
Leu Trp Ala Phe Asp Ala Val Lys Gly Asn Cys Val Leu Phe Pro Tyr Gly
                        40                  45                  50

GGC TGC CAG GGC AAC GGG AAC AAG TTC TAC TCA GAG AAG GAG TGC AGA GAG
Gly Cys Gln Gly Asn Gly Asn Lys Phe Tyr Ser Glu Lys Glu Cys Arg Glu

3'-TC TTC CTC ACG TCT CTC
                                        p-a06
```

BamHI
TAC TAGGATCC-3'
Tyr ***
ATG ATCCTAGGT-5'

FIG. 28 p-a07    5' TGGATCCTA ACC GCA GTA CTC TCT GCA CTC 3'

FIG. 29 p-s02    5' GTG ACA AAG GCC AAT CTC CCC ATA 3'

HindIII sense primer
5'-ACGCAAGTTCACGTAAAAAGC-3'
5'-ACGCAAGTTCACGTAAAAAGCTTAAAAAAGGGTATAAAAATAAA ATG AAA CAA AGT ACT ATT
                        HindIII                                Met Lys Gln Ser Thr Ile
                                                               phoA signal peptide

5'-ACT ATT
                                           -20

-1  1
                           p-s02
       5'- GTG ACA AAG GCC AAT CTC
GCA CTG GCA CTC TTA-3'
GCA CTG GCA CTC TTA CCG TTA CTG TTT ACC CCT GTG ACA AAG GCC AAT CTC
GCA CTG GCA CTC TTA CCG TTA CTG TTT ACC CCT GTG ACA AAG GCC AAT CTC
Ala Leu Ala Leu Leu Pro Leu Leu Phe Thr Pro Val Thr Lys Ala | Asn Leu
ScaI sense primer
-15            -10              -5                         1
                                                           5                    15

CCC ATA-3'
CCC ATA GTC CGG GGC CCC TGC CGA GCC TTC ATC CAG CTC TGG GCA TTT GAT
Pro Ile Val Arg Gly Pro Cys Arg Ala Phe Ile Gln Leu Trp Ala Phe Asp
polypeptide NG51
     20                                                              35
                    25                            30

GCT GTC AAG GGG AAG TGC GTC CTC TTC CCC TAC GGG GGC TGC CAG GGC AAC
Ala Val Lys Gly Lys Cys Val Leu Phe Pro Tyr Gly Gly Cys Gln Gly Asn
                40                    45                        50

GGG AAC AAG TTC TAC TCA GAG AAG TGC GAG TAC TGC GGT
Gly Asn Lys Phe Tyr Ser Glu Lys Cys Glu Tyr Cys Gly
                                   3'-CTC ACG TCT CTC ATG ACG CCA
                                              p-a07

BamHI
TAGGATCCTCTACGCCGGAACGCATCGT-3'
...3'-GAGATGCGGCCTTGCGTAGCA-5'
ATCCTAGGT-5'   BamHI antisense primer p-s03    5' CC TAC GGG GGC TCT CAG GGC AAC GG 3'

FIG. 32

```
         HindIII sense primer
      5'-ACGCAAGTTCACGTAAAAAGC-3'
      5'-ACGCAAGTTCACGTAAAAAGCTTAAAAAGGGTATAAATAAA ATG AAA CAA AGT ACT ATT
                              HindIII                   Met Lys Gln Ser Thr Ile
                                                                phoA signal peptide
                                                      -20
-15                             -10                    -5                      -1   1
GCA CTG GCA CTC TTA CCG TTT ACC CCT GTG ACA AAG GCC ACC GTC
Ala Leu Ala Leu Leu Pro Phe Thr Pro Val Thr Lys Ala Thr Val 5                       10                      15
GCC GCC TGC AAT CTC CCC ATA GTC CGG GGC CCC TGC CGA GCC TTC ATC CAG
Ala Ala Cys Asn Leu Pro Ile Val Arg Gly Pro Cys Arg Ala Phe Ile Gln
polypeptide C38S
     20                      25                      30                      35
                                                                           5'- CC TAC GGG
CTC TGG GCA TTT GAT GCT GTC AAG GGG AAC AAG TGC GTC CTC TTC CCC TAC GGG
Leu Trp Ala Phe Asp Ala Val Lys Gly Asn Lys Cys Val Leu Phe Pro Tyr Gly
p-s03                 40                      45                      50
GGC TCT CAG GGC AAC GG-3'
GGC TCT CAG GGC AAC GGG AAC AAG TTC TAC TCA GAG AAG TGC GAG TGC AGA GAG
Gly Ser Gln Gly Asn Gly Asn Lys Phe Tyr Ser Glu Lys Cys Glu Cys Arg Glu
              55                      60                      65                      70
TAC TGC GGT GTC CCT GGT GAT GGT GGT GAT CCT CGC CTG CGC CTG CGC TTC TCC AAC
Tyr Cys Gly Val Pro Gly Asp Gly Gly Asp Pro Arg Ala Glu Glu Leu Arg Phe Ser Asn
                          BamHI
TGA CAACTGGATCCTCTACGCCCGAACGCATCGT-3'
   3'-GAGATGCGGGCCTTGCGTAGCA-5'
        BamHI antisense primer
```

FIG. 33 p-s04    5' TCA GAG AAG GAG TCT AGA GAG TAC TGC 3'

HindIII sense primer
5'-ACGCAAGTTCACGTAAAAGC-3'
5'-ACGCAAGTTCACGTAAAGCTTAAAAAAGGGTATAAATAAA ATG AAA CAA AGT ACT ATT
                         HindIII                              Met Lys Gln Ser Thr Ile
                                                                              phoA signal peptide
                    -15              -10              -5                            -20

GCA CTG GCA CTC TTA CCG TTA CTG TTT ACC CCT GTG ACA AAG GCC | ACC GTC
Ala Leu Ala Leu Leu Pro Leu Leu Phe Thr Pro Val Thr Lys Ala | Thr Val
                                                                      -1  1

GCC GCC TGC AAT CTC CCC ATA GTC CGG GGC CCC TGC CGA GCC TTC ATC CAG
Ala Ala Cys Asn Leu Pro Ile Val Arg Gly Pro Cys Arg Ala Phe Ile Gln
         5                   10                  15 polypeptide C51S
20                     25                    30                    35

CTC TGG GCA TTT GAT GCT GTC AAG GGG AAC AAG TGC GTC CTC TTC CCC TAC GGG
Leu Trp Ala Phe Asp Ala Val Lys Gly Asn Lys Cys Val Leu Phe Pro Tyr Gly
                  40                    45                    50

5'- TCA GAG AAC CAG TCT AGA GAG
                                                              p-s04
GGC TGC CAG GGC AAC AAG TTC TAC TCA GAG AAC CAG TCT AGA GAG
Gly Cys Gln Gly Asn Lys Phe Tyr Ser Glu Asn Gln Ser Arg Glu
                                    55                   65                      70
                      BamHI
TAC TCC-3'
TAC TGC GGT GTC CCT GGT GAT GGT GAT GAG GAG CTG CGC TTC TCC AAC
Tyr Cys Gly Val Pro Gly Asp Gly Asp Glu Glu Leu Arg Phe Ser Asn

TGA CAACTGGATCTCTACGCCGGAACGCATCGT-3'
    3'-GAGATGCGGCCTTGCGTAGCA-5'
         BamHI antisense primer

SEQUENCE LISTING ( 1 ) GENERAL INFORMATION:

( i i i ) NUMBER OF SEQUENCES: 108

( 2 ) INFORMATION FOR SEQ ID NO:1:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Cys Asn Leu Pro Ile Val Arg Gly Pro Cys Arg Ala Phe Ile Gln Leu
 1               5                  10                  15

Trp Ala Phe Asp Ala Val Lys Gly Lys Cys Val Leu Phe Pro Tyr Gly
                20                  25                  30

Gly Cys Gln Gly Asn Gly Asn Lys Phe Tyr Ser Glu Lys Glu Cys Arg
                35                  40                  45

Glu Tyr Cys
                50
```

( 2 ) INFORMATION FOR SEQ ID NO:2:

( i ) SEQUENCE CHARACTERISTICS:

(A) LENGTH: 51 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa-1 is selected from SEQ ID NOS:20 to 24, respectively, and 107."

(ix) FEATURE:
(A) NAME/KEY: Modified-site
(B) LOCATION: 51
(D) OTHER INFORMATION: /note="Xaa-2 is selected from SEQ ID NOS:25 to 40, respectively."

(xi) SEQUENCE DESCRIPTION: SEQ ID NO:2:

| Xaa | Asn | Leu | Pro | Ile | Val | Arg | Gly | Pro | Cys | Arg | Ala | Phe | Ile | Gln | Leu |
|---|---|---|---|---|---|---|---|---|---|---|---|---|---|---|---|
| 1 | | | | 5 | | | | | 10 | | | | | | 15 |
| Trp | Ala | Phe | Asp | Ala | Val | Lys | Gly | Lys | Cys | Val | Leu | Phe | Pro | Tyr | Gly |
| | | | 20 | | | | | 25 | | | | | 30 | | |
| Gly | Cys | Gln | Gly | Asn | Gly | Asn | Lys | Phe | Tyr | Ser | Glu | Lys | Glu | Cys | Arg |
| | | 35 | | | | 40 | | | | | 45 | | | | |
| Glu | Tyr | Xaa | | | | | | | | | | | | | |
| | | 50 | | | | | | | | | | | | | |

(2) INFORMATION FOR SEQ ID NO:3:

(i) SEQUENCE CHARACTERISTICS:
(A) LENGTH: 70 amino acids
(B) TYPE: amino acid
(D) TOPOLOGY: linear (ii) MOLECULE TYPE: peptide (xi) SEQUENCE DESCRIPTION: SEQ ID NO:3:

| Thr | Val | Ala | Ala | Cys | Asn | Leu | Pro | Ile | Val | Arg | Gly | Pro | Cys | Arg | Ala |
|---|---|---|---|---|---|---|---|---|---|---|---|---|---|---|---|
| 1 | | | | 5 | | | | | 10 | | | | | 15 | |
| Phe | Ile | Gln | Leu | Trp | Ala | Phe | Asp | Ala | Val | Lys | Gly | Lys | Cys | Val | Leu |
| | | | 20 | | | | | 25 | | | | | 30 | | |
| Phe | Pro | Tyr | Gly | Gly | Cys | Gln | Gly | Asn | Gly | Asn | Lys | Phe | Tyr | Ser | Glu |
| | | | 35 | | | | | 40 | | | | | 45 | | |
| Lys | Glu | Cys | Arg | Glu | Tyr | Cys | Gly | Val | Pro | Gly | Asp | Gly | Asp | Glu | Glu |
| | 50 | | | | | 55 | | | | | 60 | | | | |
| Leu | Leu | Arg | Phe | Ser | Asn | | | | | | | | | | |
| 65 | | | | | 70 | | | | | | | | | | |

(2) INFORMATION FOR SEQ ID NO:4:

(i) SEQUENCE CHARACTERISTICS:
(A) LENGTH: 51 amino acids
(B) TYPE: amino acid
(D) TOPOLOGY: linear (ii) MOLECULE TYPE: peptide (ix) FEATURE:
(A) NAME/KEY: Modified-site
(B) LOCATION: 15
(D) OTHER INFORMATION: /note="Xaa-1 is Gln or Lys."

(ix) FEATURE:
(A) NAME/KEY: Modified-site
(B) LOCATION: 42
(D) OTHER INFORMATION: /note="Xaa-2 is Tyr when Xaa-1 is Lys; and Xaa-2 is Glu when Xaa-1 is Gln."

(xi) SEQUENCE DESCRIPTION: SEQ ID NO:4:

```
Cys  Asn  Leu  Pro  Ile  Val  Arg  Gly  Pro  Cys  Arg  Ala  Phe  Ile  Xaa  Leu
1              5                        10                       15

Trp  Ala  Phe  Asp  Ala  Val  Lys  Gly  Lys  Cys  Val  Leu  Phe  Pro  Tyr  Gly
               20                       25                       30

Gly  Cys  Gln  Gly  Asn  Gly  Asn  Lys  Phe  Xaa  Ser  Glu  Lys  Glu  Cys  Arg
          35                       40                       45

Glu  Tyr  Cys
          50
```

( 2 ) INFORMATION FOR SEQ ID NO:5:

( i ) SEQUENCE CHARACTERISTICS:
    ( A ) LENGTH: 70 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

```
Thr  Val  Ala  Ala  Cys  Asn  Leu  Pro  Ile  Val  Arg  Gly  Pro  Cys  Arg  Ala
1              5                        10                       15

Phe  Ile  Gln  Leu  Trp  Ala  Phe  Asp  Ala  Val  Lys  Gly  Lys  Cys  Val  Leu
          20                       25                       30

Phe  Pro  Tyr  Gly  Gly  Cys  Gln  Gly  Asn  Gly  Asn  Lys  Phe  Glu  Ser  Glu
          35                       40                       45

Lys  Glu  Cys  Arg  Glu  Tyr  Cys  Gly  Val  Pro  Gly  Asp  Gly  Asp  Glu  Glu
     50                       55                       60

Leu  Leu  Arg  Phe  Ser  Asn
65                  70
```

( 2 ) INFORMATION FOR SEQ ID NO:6:

( i ) SEQUENCE CHARACTERISTICS:
    ( A ) LENGTH: 70 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:6:

```
Asp  Asp  Ala  Ala  Cys  Asn  Leu  Pro  Ile  Val  Arg  Gly  Pro  Cys  Arg  Ala
1              5                        10                       15

Phe  Ile  Lys  Leu  Trp  Ala  Phe  Asp  Ala  Val  Lys  Gly  Lys  Cys  Val  Leu
          20                       25                       30

Phe  Pro  Tyr  Gly  Gly  Cys  Gln  Gly  Asn  Gly  Asn  Lys  Phe  Tyr  Ser  Glu
          35                       40                       45

Lys  Glu  Cys  Arg  Glu  Tyr  Cys  Gly  Val  Pro  Gly  Asp  Gly  Asp  Glu  Glu
     50                       55                       60

Leu  Leu  Arg  Phe  Ser  Asn
65                  70
```

( 2 ) INFORMATION FOR SEQ ID NO:7:

( i ) SEQUENCE CHARACTERISTICS:
    ( A ) LENGTH: 51 amino acids
    ( B ) TYPE: amino acid
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa-1 is selected from SEQ
      ID NOS:20 to 24, respectively."

( i x ) FEATURE:
    ( A ) NAME/KEY: Modified-site
    ( B ) LOCATION: 51
    ( D ) OTHER INFORMATION: /note="Xaa-2 is selected from SEQ
        ID NOS:25- 40, respectively."

( x i ) SEQUENCE DESCRIPTION: SEQ ID NO:7:

| Xaa | Asn | Leu | Pro | Ile | Val | Arg | Gly | Pro | Cys | Arg | Ala | Phe | Ile | Gln | Leu |
|---|---|---|---|---|---|---|---|---|---|---|---|---|---|---|---|
| 1 | | | | 5 | | | | | 10 | | | | | 15 | |

| Trp | Ala | Phe | Asp | Ala | Val | Lys | Gly | Lys | Cys | Val | Leu | Phe | Pro | Tyr | Gly |
|---|---|---|---|---|---|---|---|---|---|---|---|---|---|---|---|
| | | | 20 | | | | 25 | | | | | | 30 | | |

| Gly | Cys | Gln | Gly | Asn | Gly | Asn | Lys | Phe | Tyr | Ser | Glu | Lys | Glu | Cys | Arg |
|---|---|---|---|---|---|---|---|---|---|---|---|---|---|---|---|
| | | 35 | | | | 40 | | | | | 45 | | | | |

| Glu | Tyr | Xaa |
|---|---|---|
| | | 50 |

( 2 ) INFORMATION FOR SEQ ID NO:8:

( i ) SEQUENCE CHARACTERISTICS:
        ( A ) LENGTH: 66 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

| Thr | Val | Ala | Ala | Cys | Asn | Leu | Pro | Ile | Val | Arg | Gly | Pro | Cys | Arg | Ala |
|---|---|---|---|---|---|---|---|---|---|---|---|---|---|---|---|
| 1 | | | | 5 | | | | | 10 | | | | | 15 | |

| Phe | Ile | Gln | Leu | Trp | Ala | Phe | Asp | Ala | Val | Lys | Gly | Lys | Cys | Val | Leu |
|---|---|---|---|---|---|---|---|---|---|---|---|---|---|---|---|
| | | | 20 | | | | | 25 | | | | | 30 | | |

| Phe | Pro | Tyr | Gly | Gly | Cys | Gln | Gly | Asn | Gly | Asn | Lys | Phe | Tyr | Ser | Glu |
|---|---|---|---|---|---|---|---|---|---|---|---|---|---|---|---|
| | | | 35 | | | | | 40 | | | | | 45 | | |

| Lys | Glu | Cys | Arg | Glu | Tyr | Cys | Gly | Val | Pro | Gly | Asp | Gly | Asp | Glu | Glu |
|---|---|---|---|---|---|---|---|---|---|---|---|---|---|---|---|
| | 50 | | | | | 55 | | | | | 60 | | | | |

| Leu | Leu |
|---|---|
| 65 | |

( 2 ) INFORMATION FOR SEQ ID NO:9:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
TGCAATCTCC CCATAGTCCG GGGCCCCTGC CGAGCCTTCA TCCAGCTCTG GGCATTTGAT    60

GCTGTCAAGG GGAAGTGCGT CCTCTTCCCC TACGGGGGCT GCCAGGGCAA CGGGAACAAG   120

TTCTACTCAG AGAAGGAGTG CAGAGAGTAC TGC                                153
```

( 2 ) INFORMATION FOR SEQ ID NO:10:

( i ) SEQUENCE CHARACTERISTICS:
        ( A ) LENGTH: 149 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscdifference
        ( B ) LOCATION: replace(1, "")
        ( D ) OTHER INFORMATION: /note="N-1 is selected from SEQ ID
            NOS:41 to 46, respectively."

( i x ) FEATURE:
    ( A ) NAME/KEY: miscdifference
    ( B ) LOCATION: replace(149, "")
    ( D ) OTHER INFORMATION: /note="N-2 is selected from SEQ ID
    NOS:47 to 62, respectively."

( x i ) SEQUENCE DESCRIPTION: SEQ ID NO:10:

| | | | | | |
|---|---|---|---|---|---|
| NAATCTCCCC | ATAGTCCGGG | GCCCCTGCCG | AGCCTTCATC | CAGCTCTGGG | CATTTGATGC | 60
| TGTCAAGGGG | AAGTGCGTCC | TCTTCCCCTA | CGGGGGCTGC | CAGGGCAACG | GGAACAAGTT | 120
| CTACTCAGAG | AAGGAGTGCA | GAGAGTACN | | | | 149

( 2 ) INFORMATION FOR SEQ ID NO:11:

( i ) SEQUENCE CHARACTERISTICS:
        ( A ) LENGTH: 210 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| ACCGTCGCCG | CCTGCAATCT | CCCCATAGTC | CGGGGCCCCT | GCCGAGCCTT | CATCCAGCTC | 60
| TGGGCATTTG | ATGCTGTCAA | GGGGAAGTGC | GTCCTCTTCC | CCTACGGGGG | CTGCCAGGGC | 120
| AACGGGAACA | AGTTCTACTC | AGAGAAGGAG | TGCAGAGAGT | ACTGCGGTGT | CCCTGGTGAT | 180
| GGTGATGAGG | AGCTGCTGCG | CTTCTCCAAC | | | | 210

( 2 ) INFORMATION FOR SEQ ID NO:12:

( i ) SEQUENCE CHARACTERISTICS:
        ( A ) LENGTH: 198 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

| | | | | | |
|---|---|---|---|---|---|
| ACCGTCGCCG | CCTGCAATCT | CCCCATAGTC | CGGGGCCCCT | GCCGAGCCTT | CATCCAGCTC | 60
| TGGGCATTTG | ATGCTGTCAA | GGGGAAGTGC | GTCCTCTTCC | CCTACGGGGG | CTGCCAGGGC | 120
| AACGGGAACA | AGTTCTACTC | AGAGAAGGAG | TGCAGAGAGT | ACTGCGGTGT | CCCTGGTGAT | 180
| GGTGATGAGG | AGCTGCTG | | | | | 198

( 2 ) INFORMATION FOR SEQ ID NO:13:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscdifference
        ( B ) LOCATION: replace(43..45, "")
        ( D ) OTHER INFORMATION: /note="NNN-1 is CAG or AAG."

( i x ) FEATURE:
        ( A ) NAME/KEY: miscdifference
        ( B ) LOCATION: replace(124..126, "")
        ( D ) OTHER INFORMATION: /note="NNN-2 is GAA when NNN-1 is
        CAG, and NNN-2 is TAC when NNN-1 is AAG."

( x i ) SEQUENCE DESCRIPTION: SEQ ID NO:13:

| | | | | | |
|---|---|---|---|---|---|
| TGCAATCTCC | CCATAGTCCG | GGGCCCCTGC | CGAGCCTTCA | TCNNNCTCTG | GGCATTTGAT | 60

GCTGTCAAGG GGAAGTGCGT CCTCTTCCCC TACGGGGGCT GCCAGGGCAA CGGGAACAAG 120

TTCNNNTCAG AGAAGGAGTG CAGAGAGTAC TGC 153

( 2 ) INFORMATION FOR SEQ ID NO:14:

( i ) SEQUENCE CHARACTERISTICS:
        ( A ) LENGTH: 210 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

ACCGTCGCCG CCTGCAATCT CCCCATAGTC CGGGGCCCCT GCCGAGCCTT CATCCAGCTC 60

TGGGCATTTG ATGCTGTCAA GGGGAAGTGC GTCCTCTTCC CCTACGGGGG CTGCCAGGGC 120

AACGGGAACA AGTTCGAATC AGAGAAGGAG TGCAGAGAGT ACTGCGGTGT CCCTGGTGAT 180

GGTGATGAGG AGCTGCTGCG CTTCTCCAAC 210

( 2 ) INFORMATION FOR SEQ ID NO:15:

( i ) SEQUENCE CHARACTERISTICS:
        ( A ) LENGTH: 209 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GACGACGCCG CCTGCAATCT CCCCATAGTC CGGGGCCCCT GCCGAGCCTT CATCAAGCTC 60

TGGGCATTTG ATGCTGTCAA GGGGAAGTGC GTCCTCTTCC CCTACGGGGG CTGCCAGGGC 120

AACGGGAACA AGTTCTACTC AGAGAAGGAG TGCAGAGAGT ACTGCGGTGT CCCTGGTGAT 180

GGTATGAGGA GCTGCTGCGC TTCTCCAAC 209

( 2 ) INFORMATION FOR SEQ ID NO:16:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

```
Thr Val Ala Ala Cys Asn Leu Pro Ile Val Arg Gly Pro Cys Arg Ala
 1               5                  10                 15
Phe Ile Gln Leu Trp Ala Phe Asp Ala Val Lys Gly Lys Cys Val Leu
             20                 25                 30
Phe Pro Tyr Gly Gly Cys Gln Gly Asn Gly Asn Lys Phe Tyr Ser Glu
             35                 40                 45
Lys Glu Cys Arg Glu Tyr
         50
```

( 2 ) INFORMATION FOR SEQ ID NO:17:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

```
    Asn Leu Pro Ile Val Arg Gly Pro Cys Arg Ala Phe Ile Gln Leu Trp
    1               5                   10                  15

Ala Phe Asp Ala Val Lys Gly Lys Cys Val Leu Phe Pro Tyr Gly Gly
                    20                  25                  30

Cys Gln Gly Asn Gly Asn Lys Phe Tyr Ser Glu Lys Glu Cys Arg Glu
                35                  40                  45

Tyr Cys Gly
            50
```

(2) INFORMATION FOR SEQ ID NO:18:

(i) SEQUENCE CHARACTERISTICS:
        (A) LENGTH: 70 amino acids
        (B) TYPE: amino acid
        (D) TOPOLOGY: linear (ii) MOLECULE TYPE: peptide (xi) SEQUENCE DESCRIPTION: SEQ ID NO:18:

```
    Thr Val Ala Ala Cys Asn Leu Pro Ile Val Arg Gly Pro Cys Arg Ala
    1               5                   10                  15

Phe Ile Gln Leu Trp Ala Phe Asp Ala Val Lys Gly Lys Cys Val Leu
                      20                  25                  30

Phe Pro Tyr Gly Gly Ser Gln Gly Asn Gly Asn Lys Phe Tyr Ser Glu
                35                  40                  45

Lys Glu Cys Arg Glu Tyr Cys Gly Val Pro Gly Asp Gly Asp Glu Glu
                50                  55                  60

Leu Leu Arg Phe Ser Asn
    65                  70
```

(2) INFORMATION FOR SEQ ID NO:19:

(i) SEQUENCE CHARACTERISTICS:
        (A) LENGTH: 70 amino acids
        (B) TYPE: amino acid
        (D) TOPOLOGY: linear (ii) MOLECULE TYPE: peptide (xi) SEQUENCE DESCRIPTION: SEQ ID NO:19:

```
    Thr Val Ala Ala Cys Asn Leu Pro Ile Val Arg Gly Pro Cys Arg Ala
    1               5                   10                  15

Phe Ile Gln Leu Trp Ala Phe Asp Ala Val Lys Gly Lys Cys Val Leu
                    20                  25                  30

Phe Pro Tyr Gly Gly Cys Gln Gly Asn Gly Asn Lys Phe Tyr Ser Glu
                35                  40                  45

Lys Glu Ser Arg Glu Tyr Cys Gly Val Pro Gly Asp Gly Asp Glu Glu
                50                  55                  60

Leu Leu Arg Phe Ser Asn
    65                  70
```

(2) INFORMATION FOR SEQ ID NO:20:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:20:

```
    Thr Val Ala Ala Cys
    1               5
```

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:21:

Val  Ala  Ala  Cys
    1

( 2 ) INFORMATION FOR SEQ ID NO:22:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:22:

Ala  Ala  Cys
    1

( 2 ) INFORMATION FOR SEQ ID NO:23:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:23:

Ala  Cys
    1

( 2 ) INFORMATION FOR SEQ ID NO:24:

( i ) SEQUENCE CHARACTERISTICS:
        ( A ) LENGTH: 1 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:24:

Cys
    1

( 2 ) INFORMATION FOR SEQ ID NO:25:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:25:

Cys  Gly  Val  Pro  Gly  Asp  Gly  Asp  Glu  Glu  Leu  Leu  Arg  Phe  Ser  Asn
    1                5                        10                      15

( 2 ) INFORMATION FOR SEQ ID NO:26:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:26:

Cys Gly Val Pro Gly Asp Gly Asp Glu Glu Leu Leu Arg Phe Ser
1               5                   10                  15

( 2 ) INFORMATION FOR SEQ ID NO:27:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:27:

Cys Gly Val Pro Gly Asp Gly Asp Glu Glu Leu Leu Arg Phe
1               5                   10

( 2 ) INFORMATION FOR SEQ ID NO:28:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:28:

Cys Gly Val Pro Gly Asp Gly Asp Glu Glu Leu Leu Arg
1               5                   10

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:29:

Cys Gly Val Pro Gly Asp Gly Asp Glu Glu Leu Leu
1               5                   10

( 2 ) INFORMATION FOR SEQ ID NO:30:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:30:

Cys Gly Val Pro Gly Asp Gly Asp Glu Glu Leu
1               5                   10

( 2 ) INFORMATION FOR SEQ ID NO:31:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:31:

Cys Gly Val Pro Gly Asp Gly Asp Glu Glu
1               5                   10

( 2 ) INFORMATION FOR SEQ ID NO:32:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

Cys Gly Val Pro Gly Asp Gly Asp Glu
    1                   5

( 2 ) INFORMATION FOR SEQ ID NO:33:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

Cys Gly Val Pro Gly Asp Gly Asp
    1                   5

( 2 ) INFORMATION FOR SEQ ID NO:34:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

Cys Gly Val Pro Gly Asp Gly
    1                   5

( 2 ) INFORMATION FOR SEQ ID NO:35:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:35:

Cys Gly Val Pro Gly Asp
    1                   5

( 2 ) INFORMATION FOR SEQ ID NO:36:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:36:

Cys Gly Val Pro Gly
    1               5

( 2 ) INFORMATION FOR SEQ ID NO:37:

( i ) SEQUENCE CHARACTERISTICS:
        ( A ) LENGTH: 4 amino acids
        ( B ) TYPE: amino acid ( D ) TOPOLOGY: linear ( i i ) MOLECULE TYPE: peptide ( x i ) SEQUENCE DESCRIPTION: SEQ ID NO:37:

Cys Gly Val Pro
1

( 2 ) INFORMATION FOR SEQ ID NO:38:

( i ) SEQUENCE CHARACTERISTICS:
( A ) LENGTH: 3 amino acids
( B ) TYPE: amino acid
( D ) TOPOLOGY: linear ( i i ) MOLECULE TYPE: peptide ( x i ) SEQUENCE DESCRIPTION: SEQ ID NO:38:

Cys Gly Val
1

( 2 ) INFORMATION FOR SEQ ID NO:39:

( i ) SEQUENCE CHARACTERISTICS:
( A ) LENGTH: 2 amino acids
( B ) TYPE: amino acid
( D ) TOPOLOGY: linear ( i i ) MOLECULE TYPE: peptide ( x i ) SEQUENCE DESCRIPTION: SEQ ID NO:39:

Cys Gly
1

( 2 ) INFORMATION FOR SEQ ID NO:40:

( i ) SEQUENCE CHARACTERISTICS:
( A ) LENGTH: 1 amino acids
( B ) TYPE: amino acid
( D ) TOPOLOGY: linear ( i i ) MOLECULE TYPE: peptide ( x i ) SEQUENCE DESCRIPTION: SEQ ID NO:40:

Cys
1

( 2 ) INFORMATION FOR SEQ ID NO:41:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:41:

ACTGTGGCGG CCTGC 15

( 2 ) INFORMATION FOR SEQ ID NO:42:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:42:

ACCGTCGCCG CCTGC                                                                      15

( 2 ) INFORMATION FOR SEQ ID NO:43:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

GTCGCCGCCT GC                                                                         12

( 2 ) INFORMATION FOR SEQ ID NO:44:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

GCCGCCTGC                                                                             9

( 2 ) INFORMATION FOR SEQ ID NO:45:

( i ) SEQUENCE CHARACTERISTICS:
        ( A ) LENGTH: 6 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

GCCTGC                                                                                6

( 2 ) INFORMATION FOR SEQ ID NO:46:

( i ) SEQUENCE CHARACTERISTICS:
        ( A ) LENGTH: 3 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

TGC                                                                                   3

( 2 ) INFORMATION FOR SEQ ID NO:47:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:47:

TGCGGTGTCC CTGGTGATGG TGATGAGGAG CTGCTGCGCT TCTCCAAC                                   48

( 2 ) INFORMATION FOR SEQ ID NO:48:

( i ) SEQUENCE CHARACTERISTICS:
        ( A ) LENGTH: 45 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:48:

TGCGGTGTCC CTGGTGATGG TGATGAGGAG CTGCTGCGCT TCTCC    45

(2) INFORMATION FOR SEQ ID NO:49:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:49:

TGCGGTGTCC CTGGTGATGG TGATGAGGAG CTGCTGCGCT TC    42

(2) INFORMATION FOR SEQ ID NO:50:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:50:

TGCGGTGTCC CTGGTGATGG TGATGAGGAG CTGCTGCGC    39

(2) INFORMATION FOR SEQ ID NO:51:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:51:

TGCGGTGTCC CTGGTGATGG TGATGAGGAG CTGCTG    36

(2) INFORMATION FOR SEQ ID NO:52:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:52:

TGCGGTGTCC CTGGTGATGG TGATGAGGAG CTG    33

(2) INFORMATION FOR SEQ ID NO:53:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:53:

TGCGGTGTCC CTGGTGATGG TGATGAGGAG                                                      30

( 2 ) INFORMATION FOR SEQ ID NO:54:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

TGCGGTGTCC CTGGTGATGG TGATGAG                                                         27

( 2 ) INFORMATION FOR SEQ ID NO:55:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

TGCGGTGTCC CTGGTGATGG TGAT                                                            24

( 2 ) INFORMATION FOR SEQ ID NO:56:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

TGCGGTGTCC CTGGTGATGG T                                                               21

( 2 ) INFORMATION FOR SEQ ID NO:57:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

TGCGGTGTCC CTGGTGAT                                                                   18

( 2 ) INFORMATION FOR SEQ ID NO:58:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

TGCGGTGTCC CTGGT                                                                      15

( 2 ) INFORMATION FOR SEQ ID NO:59:

( i ) SEQUENCE CHARACTERISTICS:

(A) LENGTH: 12 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:59:

TGCGGTGTCC CT                                                                 12

(2) INFORMATION FOR SEQ ID NO:60:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:60:

TGCGGTGTC                                                                      9

(2) INFORMATION FOR SEQ ID NO:61:

(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:61:

TGCGGT                                                                         6

(2) INFORMATION FOR SEQ ID NO:62:

(i) SEQUENCE CHARACTERISTICS:
(A) LENGTH: 3 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:62:

TGC                                                                            3

(2) INFORMATION FOR SEQ ID NO:63:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:63:

AGCTTAAAAA AGGGTATAAA ATAAAATGAA AC                                            32

(2) INFORMATION FOR SEQ ID NO:64:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

( i x ) FEATURE:
    ( A ) NAME/KEY: miscfeature
    ( B ) LOCATION: complement (1..36)

( x i ) SEQUENCE DESCRIPTION: SEQ ID NO:64:

ATTTTTTCCC ATATTTTATT TTACTTTGTT TCATGA    36

( 2 ) INFORMATION FOR SEQ ID NO:65:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

AAAGTACTAT TGCACTGGCA CTCTTACCGT TACTGTTT    38

( 2 ) INFORMATION FOR SEQ ID NO:66:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: complement (1..36)

( x i ) SEQUENCE DESCRIPTION: SEQ ID NO:66:

TAACGTGACC GTGAGAATGG CAATGACAAA TGGGGA    36

( 2 ) INFORMATION FOR SEQ ID NO:67:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

ACCCCTGTGA CAAAAGCCGA CTCCCTAGGT CG    32

( 2 ) INFORMATION FOR SEQ ID NO:68:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: miscfeature
        ( B ) LOCATION: complement (1..26)

( x i ) SEQUENCE DESCRIPTION: SEQ ID NO:68:

CACTGTTTTC GGCTGAGGGA TCCAGC    26

( 2 ) INFORMATION FOR SEQ ID NO:69:

( i ) SEQUENCE CHARACTERISTICS:
        ( A ) LENGTH: 29 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:69:

TTGGCCACCG TCGCCGCCTG CAACCTGCC 29

( 2 ) INFORMATION FOR SEQ ID NO:70:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( v ) FRAGMENT TYPE: N-terminal ( x i ) SEQUENCE DESCRIPTION: SEQ ID NO:70:

Thr Val Ala Ala Cys Asn Leu Pro
1               5

( 2 ) INFORMATION FOR SEQ ID NO:71:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:71:

TGGATCCAGT TGTCAGTTGG AGAAGC 26

( 2 ) INFORMATION FOR SEQ ID NO:72:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( v ) FRAGMENT TYPE: C-terminal ( x i ) SEQUENCE DESCRIPTION: SEQ ID NO:72:

Arg Phe Ser Asn
1

( 2 ) INFORMATION FOR SEQ ID NO:73:

( i ) SEQUENCE CHARACTERISTICS:
( A ) LENGTH: 47 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:73:

ACTATTGCAC TGGCACTCTT ACCGTTACTG TTTACCCCTG TGACAAA 47

( 2 ) INFORMATION FOR SEQ ID NO:74:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear (  i i  ) MOLECULE TYPE: DNA (genomic)

(  i x  ) FEATURE:
    ( A ) NAME/KEY: miscfeature
    ( B ) LOCATION: complement (1..51)

( x i ) SEQUENCE DESCRIPTION: SEQ ID NO:74:

```
TGATAACGTG ACCGTGAGAA TGGCAATGAC AAATGGGGAC ACTGTTTCCG G         51
```

( 2 ) INFORMATION FOR SEQ ID NO:75:

( i ) SEQUENCE CHARACTERISTICS:
        ( A ) LENGTH: 313 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 27..303

( x i ) SEQUENCE DESCRIPTION: SEQ ID NO:75:

```
AAGCTTAAAA AAGGGTATAA AATAAA ATG AAA CAA AGT ACT ATT GCA CTG GCA      53
                              Met Lys Gln Ser Thr Ile Ala Leu Ala
                               1               5

CTC TTA CCG TTA CTG TTT ACC CCT GTG ACA AAG GCC ACC GTC GCC GCC     101
Leu Leu Pro Leu Leu Phe Thr Pro Val Thr Lys Ala Thr Val Ala Ala
 10              15                  20                  25

TGC AAT CTC CCC ATA GTC CGG GGC CCC TGC CGA GCC TTC ATC CAG CTC     149
Cys Asn Leu Pro Ile Val Arg Gly Pro Cys Arg Ala Phe Ile Gln Leu
                 30                  35                  40

TGG GCA TTT GAT GCT GTC AAG GGG AAG TGC GTC CTC TTC CCC TAC GGG     197
Trp Ala Phe Asp Ala Val Lys Gly Lys Cys Val Leu Phe Pro Tyr Gly
             45                  50                  55

GGC TGC CAG GGG AAC GGG AAC AAG TTC TAC TCA GAG AAG GAG TGC AGA     245
Gly Cys Gln Gly Asn Gly Asn Lys Phe Tyr Ser Glu Lys Glu Cys Arg
         60                  65                  70

GAG TAC TGC GGT GTC CCT GGT GAT GGT GAT GAG GAG CTG CTG CGC TTC     293
Glu Tyr Cys Gly Val Pro Gly Asp Gly Asp Glu Glu Leu Leu Arg Phe
     75                  80                  85

TCC AAC TGA C AACTGGATCC                                             313
Ser Asn  *
 90
```

( 2 ) INFORMATION FOR SEQ ID NO:76:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

```
Met Lys Gln Ser Thr Ile Ala Leu Ala Leu Leu Pro Leu Leu Phe Thr
 1               5                  10                  15

Pro Val Thr Lys Ala Thr Val Ala Ala Cys Asn Leu Pro Ile Val Arg
                 20                  25                  30

Gly Pro Cys Arg Ala Phe Ile Gln Leu Trp Ala Phe Asp Ala Val Lys
             35                  40                  45

Gly Lys Cys Val Leu Phe Pro Tyr Gly Gly Cys Gln Gly Asn Gly Asn
         50                  55                  60

Lys Phe Tyr Ser Glu Lys Glu Cys Arg Glu Tyr Cys Gly Val Pro Gly
 65                  70                  75                  80
```

Asp Gly Asp Glu Glu Leu Leu Arg Phe Ser Asn
              85                          90

( 2 ) INFORMATION FOR SEQ ID NO:77:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:77:

ACTATTGCAC TGGCACTCTT A                                                    21

( 2 ) INFORMATION FOR SEQ ID NO:78:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:78:

TGGATCCTAG CAGTACTCTC TGCACTCCTT                                           30

( 2 ) INFORMATION FOR SEQ ID NO:79:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:79:

ACGCAAGTTC ACGTAAAAAG C                                                    21

( 2 ) INFORMATION FOR SEQ ID NO:80:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:80:

ATGGGGAGAT TGCAGGCCTT TGTCACAG                                             28

( 2 ) INFORMATION FOR SEQ ID NO:81:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:81:

ACGATGCGTT CCGGCGTAGA G                                                    21

( 2 ) INFORMATION FOR SEQ ID NO:82:

(i) SEQUENCE CHARACTERISTICS:
    (A) LENGTH: 287 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 44..263

(xi) SEQUENCE DESCRIPTION: SEQ ID NO:82:

| ACGCAAGTTC | ACGTAAAAAG | CTTAAAAAAG | GGTATAAAAT | AAA | ATG | AAA | CAA | AGT | 55 |
|---|---|---|---|---|---|---|---|---|---|
|  |  |  |  |  | Met | Lys | Gln | Ser |  |
|  |  |  |  |  | 1 |  |  |  |  |

| ACT | ATT | GCA | CTG | GCA | CTC | TTA | CCG | TTA | CTG | TTT | ACC | CCT | GTG | ACA | AAG | 103 |
|---|---|---|---|---|---|---|---|---|---|---|---|---|---|---|---|---|
| Thr | Ile | Ala | Leu | Ala | Leu | Leu | Pro | Leu | Leu | Phe | Thr | Pro | Val | Thr | Lys |  |
| 5 |  |  |  | 10 |  |  |  |  | 15 |  |  |  |  | 20 |  |  |

| GCC | TGC | AAT | CTC | CCC | ATA | GTC | CGG | GGC | CCC | TGC | CGA | GCC | TTC | ATC | CAG | 151 |
|---|---|---|---|---|---|---|---|---|---|---|---|---|---|---|---|---|
| Ala | Cys | Asn | Leu | Pro | Ile | Val | Arg | Gly | Pro | Cys | Arg | Ala | Phe | Ile | Gln |  |
|  |  |  | 25 |  |  |  |  | 30 |  |  |  |  | 35 |  |  |  |

| CTC | TGG | GCA | TTT | GAT | GCT | GTC | AAG | GGG | AAG | TGC | GTC | CTC | TTC | CCC | TAC | 199 |
|---|---|---|---|---|---|---|---|---|---|---|---|---|---|---|---|---|
| Leu | Trp | Ala | Phe | Asp | Ala | Val | Lys | Gly | Lys | Cys | Val | Leu | Phe | Pro | Tyr |  |
|  |  |  | 40 |  |  |  | 45 |  |  |  |  | 50 |  |  |  |  |

| GGG | GGC | TGC | CAG | GGC | AAC | GGG | AAC | AAG | TTC | TAC | TCA | GAG | AAG | GAG | TGC | 247 |
|---|---|---|---|---|---|---|---|---|---|---|---|---|---|---|---|---|
| Gly | Gly | Cys | Gln | Gly | Asn | Gly | Asn | Lys | Phe | Tyr | Ser | Glu | Lys | Glu | Cys |  |
|  |  | 55 |  |  |  | 60 |  |  |  |  | 65 |  |  |  |  |  |

| AGA | GAG | TAC | TGC | TAG | G ATCCTCTACG | CCGGAACGCA | TCGT | 287 |
|---|---|---|---|---|---|---|---|---|
| Arg | Glu | Tyr | Cys | * |  |  |  |  |
| 70 |  |  |  |  |  |  |  |  |

(2) INFORMATION FOR SEQ ID NO:83:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO:83:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 |  |  |  | 5 |  |  |  |  | 10 |  |  |  |  | 15 |  |

| Pro | Val | Thr | Lys | Ala | Cys | Asn | Leu | Pro | Ile | Val | Arg | Gly | Pro | Cys | Arg |
|---|---|---|---|---|---|---|---|---|---|---|---|---|---|---|---|
|  |  |  | 20 |  |  |  |  | 25 |  |  |  |  | 30 |  |  |

| Ala | Phe | Ile | Gln | Leu | Trp | Ala | Phe | Asp | Ala | Val | Lys | Gly | Lys | Cys | Val |
|---|---|---|---|---|---|---|---|---|---|---|---|---|---|---|---|
|  |  | 35 |  |  |  |  | 40 |  |  |  |  | 45 |  |  |  |

| Leu | Phe | Pro | Tyr | Gly | Gly | Cys | Gln | Gly | Asn | Gly | Asn | Lys | Phe | Tyr | Ser |
|---|---|---|---|---|---|---|---|---|---|---|---|---|---|---|---|
|  | 50 |  |  |  |  | 55 |  |  |  |  | 60 |  |  |  |  |

| Glu | Lys | Glu | Cys | Arg | Glu | Tyr | Cys |
|---|---|---|---|---|---|---|---|
| 65 |  |  |  |  | 70 |  |  |

(2) INFORMATION FOR SEQ ID NO:84:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

TGGATCCTAC AGCAGCTCCT CATCACCATC                                30

( 2 ) INFORMATION FOR SEQ ID NO:85:

( i ) SEQUENCE CHARACTERISTICS:
    ( A ) LENGTH: 295 base pairs
    ( B ) TYPE: nucleic acid
    ( C ) STRANDEDNESS: single
    ( D ) TOPOLOGY: linear ( i i ) MOLECULE TYPE: DNA (genomic)

( i x ) FEATURE:
    ( A ) NAME/KEY: CDS
    ( B ) LOCATION: 27..290

( x i ) SEQUENCE DESCRIPTION: SEQ ID NO:85:

```
AAGCTTAAAA AAGGGTATAA AATAAA ATG AAA CAA AGT ACT ATT GCA CTG GCA      53
                                Met Lys Gln Ser Thr Ile Ala Leu Ala
                                 1               5

CTC TTA CCG TTA CTG TTT ACC CCT GTG ACA AAG GCC ACC GTC GCC GCC      101
Leu Leu Pro Leu Leu Phe Thr Pro Val Thr Lys Ala Thr Val Ala Ala
 10              15                  20                  25

TGC AAT CTC CCC ATA GTC CGG GGC CCC TGC CGA GCC TTC ATC CAG CTC      149
Cys Asn Leu Pro Ile Val Arg Gly Pro Cys Arg Ala Phe Ile Gln Leu
                 30                  35                  40

TGG GCA TTT GAT GCT GTC AAG GGG AAG TGC GTC CTC TTC CCC TAC GGG      197
Trp Ala Phe Asp Ala Val Lys Gly Lys Cys Val Leu Phe Pro Tyr Gly
             45                  50                  55

GGC TGC CAG GGC AAC GGG AAC AAG TTC TAC TCA GAG AAG GAG TGC AGA      245
Gly Cys Gln Gly Asn Gly Asn Lys Phe Tyr Ser Glu Lys Glu Cys Arg
                 60                  65                  70

GAG TAC TGC GGT GTC CCT GGT GAT GGT GAT GAG GAG CTG CTG TAGGATCC    295
Glu Tyr Cys Gly Val Pro Gly Asp Gly Asp Glu Glu Leu Leu
         75                  80                  85
```

( 2 ) INFORMATION FOR SEQ ID NO:86:

( i ) SEQUENCE CHARACTERISTICS:
    ( A ) LENGTH: 87 amino acids
    ( B ) TYPE: amino acid
    ( D ) TOPOLOGY: linear ( i i ) MOLECULE TYPE: protein ( x i ) SEQUENCE DESCRIPTION: SEQ ID NO:86:

```
Met Lys Gln Ser Thr Ile Ala Leu Ala Leu Leu Pro Leu Leu Phe Thr
 1               5                  10                  15

Pro Val Thr Lys Ala Thr Val Ala Ala Cys Asn Leu Pro Ile Val Arg
             20                  25                  30

Gly Pro Cys Arg Ala Phe Ile Gln Leu Trp Ala Phe Asp Ala Val Lys
             35                  40                  45

Gly Lys Cys Val Leu Phe Pro Tyr Gly Gly Cys Gln Gly Asn Gly Asn
         50                  55                  60

Lys Phe Tyr Ser Glu Lys Glu Cys Arg Glu Tyr Cys Gly Val Pro Gly
 65              70                  75                  80

Asp Gly Asp Glu Glu Leu Leu
             85
```

( 2 ) INFORMATION FOR SEQ ID NO:87:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:87:

GGAACAAGTT CGAATCAGAG AAGGA 25

( 2 ) INFORMATION FOR SEQ ID NO:88:

( i ) SEQUENCE CHARACTERISTICS:
        ( A ) LENGTH: 313 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 27..302

( x i ) SEQUENCE DESCRIPTION: SEQ ID NO:88:

```
AAGCTTAAAA AAGGGTATAA AATAAA ATG AAA CAA AGT ACT ATT GCA CTG GCA      53
                             Met Lys Gln Ser Thr Ile Ala Leu Ala
                              1               5

CTC TTA CCG TTA CTG TTT ACC CCT GTG ACA AAG GCC ACC GTC GCC GCC     101
Leu Leu Pro Leu Leu Phe Thr Pro Val Thr Lys Ala Thr Val Ala Ala
 10              15                  20                  25

TGC AAT CTC CCC ATA GTC CGG GGC CCC TGC CGA GCC TTC ATC CAG CTC     149
Cys Asn Leu Pro Ile Val Arg Gly Pro Cys Arg Ala Phe Ile Gln Leu
             30                  35                  40

TGG GCA TTT GAT GCT GTC AAG GGG AAG TGC GTC CTC TTC CCC TAC GGG     197
Trp Ala Phe Asp Ala Val Lys Gly Lys Cys Val Leu Phe Pro Tyr Gly
         45                  50                  55

GGC TGC CAG GGC AAC GGG AAC AAG TTC GAA TCA GAG AAG GAG TGC AGA     245
Gly Cys Gln Gly Asn Gly Asn Lys Phe Glu Ser Glu Lys Glu Cys Arg
     60                  65                  70

GAG TAC TGC GGT GTC CCT GGT GAT GGT GAT GAG GAG CTG CTG CGC TTC     293
Glu Tyr Cys Gly Val Pro Gly Asp Gly Asp Glu Glu Leu Leu Arg Phe
 75                  80                  85

TCC AAC TGACAACTGG ATCC                                             313
Ser Asn
 90
```

( 2 ) INFORMATION FOR SEQ ID NO:89:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:89:

```
Met Lys Gln Ser Thr Ile Ala Leu Ala Leu Leu Pro Leu Leu Phe Thr
 1               5                  10                  15

Pro Val Thr Lys Ala Thr Val Ala Ala Cys Asn Leu Pro Ile Val Arg
                 20                  25                  30

Gly Pro Cys Arg Ala Phe Ile Gln Leu Trp Ala Phe Asp Ala Val Lys
             35                  40                  45

Gly Lys Cys Val Leu Phe Pro Tyr Gly Gly Cys Gln Gly Asn Gly Asn
         50                  55                  60

Lys Phe Glu Ser Glu Lys Glu Cys Arg Glu Tyr Cys Gly Val Pro Gly
 65                  70                  75                  80

Asp Gly Asp Glu Glu Leu Leu Arg Phe Ser Asn
                 85                  90
```

( 2 ) INFORMATION FOR SEQ ID NO:90:

( i ) SEQUENCE CHARACTERISTICS:

(A) LENGTH: 28 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:90:

TGACAAAGGC CGACGACGCC GCCTGCAA                    28

(2) INFORMATION FOR SEQ ID NO:91:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:91:

CAAATGCCCA GAGCTTGATG AAGGCTCGGC A                 31

(2) INFORMATION FOR SEQ ID NO:92:

(i) SEQUENCE CHARACTERISTICS:
(A) LENGTH: 350 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 44..319

(xi) SEQUENCE DESCRIPTION: SEQ ID NO:92:

| ACGCAAGTTC ACGTAAAAAG CTTAAAAAAG GGTATAAAAT AAA | ATG<br>Met<br>1 | AAA<br>Lys | CAA<br>Gln | AGT<br>Ser | 55 |
|---|---|---|---|---|---|

| ACT<br>Thr<br>5 | ATT<br>Ile | GCA<br>Ala | CTG<br>Leu | GCA<br>Ala | CTC<br>Leu<br>10 | TTA<br>Leu | CCG<br>Pro | TTA<br>Leu | CTG<br>Leu | TTT<br>Phe<br>15 | ACC<br>Thr | CCT<br>Pro | GTG<br>Val | ACA<br>Thr | AAG<br>Lys<br>20 | 103 |

| GCC<br>Ala | GAC<br>Asp | GAC<br>Asp | GCC<br>Ala | GCC<br>Ala<br>25 | TGC<br>Cys | AAT<br>Asn | CTC<br>Leu | CCC<br>Pro | ATA<br>Ile<br>30 | GTC<br>Val | CGG<br>Arg | GGC<br>Gly | CCC<br>Pro | TGC<br>Cys<br>35 | CGA<br>Arg | 151 |

| GCC<br>Ala | TTC<br>Phe | ATC<br>Ile | AAG<br>Lys<br>40 | CTC<br>Leu | TGG<br>Trp | GCA<br>Ala | TTT<br>Phe | GAT<br>Asp<br>45 | GCT<br>Ala | GTC<br>Val | AAG<br>Lys | GGG<br>Gly | AAG<br>Lys<br>50 | TGC<br>Cys | GTC<br>Val | 199 |

| CTC<br>Leu | TTC<br>Phe | CCC<br>Pro<br>55 | TAC<br>Tyr | GGG<br>Gly | GGC<br>Gly | TGC<br>Cys | CAG<br>Gln<br>60 | GGC<br>Gly | AAC<br>Asn | GGG<br>Gly | AAC<br>Asn | AAG<br>Lys<br>65 | TTC<br>Phe | TAC<br>Tyr | TCA<br>Ser | 247 |

| GAG<br>Glu | AAG<br>Lys<br>70 | GAG<br>Glu | TGC<br>Cys | AGA<br>Arg | GAG<br>Glu | TAC<br>Tyr<br>75 | TGC<br>Cys | GGT<br>Gly | GTC<br>Val | CCT<br>Pro | GGT<br>Gly<br>80 | GAT<br>Asp | GGT<br>Gly | GAT<br>Asp | GAG<br>Glu | 295 |

| GAG<br>Glu<br>85 | CTG<br>Leu | CTG<br>Leu | CGC<br>Arg | TTC<br>Phe | TCC<br>Ser<br>90 | AAC<br>Asn | TGACAACTGG ATCCTCTACG CCGGAACGCA | 346 |
|---|---|---|---|---|---|---|---|---|

TCGT                                              350

(2) INFORMATION FOR SEQ ID NO:93:

(i) SEQUENCE CHARACTERISTICS:
(A) LENGTH: 91 amino acids
(B) TYPE: amino acid
(D) TOPOLOGY: linear (ii) MOLECULE TYPE: protein ( x i ) SEQUENCE DESCRIPTION: SEQ ID NO:93:

| Met | Lys | Gln | Ser | Thr | Ile | Ala | Leu | Ala | Leu | Leu | Pro | Leu | Leu | Phe | Thr |
|---|---|---|---|---|---|---|---|---|---|---|---|---|---|---|---|
| 1 | | | | 5 | | | | | 10 | | | | | 15 | |

| Pro | Val | Thr | Lys | Ala | Asp | Asp | Ala | Ala | Cys | Asn | Leu | Pro | Ile | Val | Arg |
|---|---|---|---|---|---|---|---|---|---|---|---|---|---|---|---|
| | | | 20 | | | | | 25 | | | | | 30 | | |

| Gly | Pro | Cys | Arg | Ala | Phe | Ile | Lys | Leu | Trp | Ala | Phe | Asp | Ala | Val | Lys |
|---|---|---|---|---|---|---|---|---|---|---|---|---|---|---|---|
| | | 35 | | | | | 40 | | | | | 45 | | | |

| Gly | Lys | Cys | Val | Leu | Phe | Pro | Tyr | Gly | Gly | Cys | Gln | Gly | Asn | Gly | Asn |
|---|---|---|---|---|---|---|---|---|---|---|---|---|---|---|---|
| | 50 | | | | | 55 | | | | | 60 | | | | |

| Lys | Phe | Tyr | Ser | Glu | Lys | Glu | Cys | Arg | Glu | Tyr | Cys | Gly | Val | Pro | Gly |
|---|---|---|---|---|---|---|---|---|---|---|---|---|---|---|---|
| 65 | | | | | 70 | | | | | 75 | | | | | 80 |

| Asp | Gly | Asp | Glu | Glu | Leu | Leu | Arg | Phe | Ser | Asn |
|---|---|---|---|---|---|---|---|---|---|---|
| | | | | 85 | | | | | 90 | |

( 2 ) INFORMATION FOR SEQ ID NO:94:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:94:

TGGATCCTAG TACTCTCTGC ACTCCTTCT                    29

( 2 ) INFORMATION FOR SEQ ID NO:95:

( i ) SEQUENCE CHARACTERISTICS:
        ( A ) LENGTH: 276 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 44..271

( x i ) SEQUENCE DESCRIPTION: SEQ ID NO:95:

| ACGCAAGTTC | ACGTAAAAAG | CTTAAAAAAG | GGTATAAAAT | AAA | ATG | AAA | CAA | AGT | 55 |
|---|---|---|---|---|---|---|---|---|---|
| | | | | | Met | Lys | Gln | Ser | |
| | | | | | 1 | | | | |

| ACT | ATT | GCA | CTG | GCA | CTC | TTA | CCG | TTA | CTG | TTT | ACC | CCT | GTG | ACA | AAG | 103 |
|---|---|---|---|---|---|---|---|---|---|---|---|---|---|---|---|---|
| Thr | Ile | Ala | Leu | Ala | Leu | Leu | Pro | Leu | Leu | Phe | Thr | Pro | Val | Thr | Lys | |
| 5 | | | | | 10 | | | | | 15 | | | | | 20 | |

| GCC | ACC | GTC | GCC | GCC | TGC | AAT | CTC | CCC | ATA | GTC | CGG | GGC | CCC | TGC | CGA | 151 |
|---|---|---|---|---|---|---|---|---|---|---|---|---|---|---|---|---|
| Ala | Thr | Val | Ala | Ala | Cys | Asn | Leu | Pro | Ile | Val | Arg | Gly | Pro | Cys | Arg | |
| | | | | 25 | | | | | 30 | | | | | 35 | | |

| GCC | TTC | ATC | CAG | CTC | TGG | GCA | TTT | GAT | GCT | GTC | AAG | GGG | AAG | TGC | GTC | 199 |
|---|---|---|---|---|---|---|---|---|---|---|---|---|---|---|---|---|
| Ala | Phe | Ile | Gln | Leu | Trp | Ala | Phe | Asp | Ala | Val | Lys | Gly | Lys | Cys | Val | |
| | | | 40 | | | | | 45 | | | | | 50 | | | |

| CTC | TTC | CCC | TAC | GGG | GGC | TGC | CAG | GGC | AAC | GGG | AAC | AAG | TTC | TAC | TCA | 247 |
|---|---|---|---|---|---|---|---|---|---|---|---|---|---|---|---|---|
| Leu | Phe | Pro | Tyr | Gly | Gly | Cys | Gln | Gly | Asn | Gly | Asn | Lys | Phe | Tyr | Ser | |
| | | 55 | | | | | 60 | | | | | 65 | | | | |

| GAG | AAG | GAG | TGC | AGA | GAG | TAC | TAGGATCC | 276 |
|---|---|---|---|---|---|---|---|---|
| Glu | Lys | Glu | Cys | Arg | Glu | Tyr | | |
| | 70 | | | | | 75 | | |

( 2 ) INFORMATION FOR SEQ ID NO:96:

( i ) SEQUENCE CHARACTERISTICS:
        ( A ) LENGTH: 75 amino acids (B) TYPE: amino acid
(D) TOPOLOGY: linear (ii) MOLECULE TYPE: protein (xi) SEQUENCE DESCRIPTION: SEQ ID NO:96:

```
Met Lys Gln Ser Thr Ile Ala Leu Ala Leu Leu Pro Leu Leu Phe Thr
 1               5                  10                  15
Pro Val Thr Lys Ala Thr Val Ala Ala Cys Asn Leu Pro Ile Val Arg
                20                  25                  30
Gly Pro Cys Arg Ala Phe Ile Gln Leu Trp Ala Phe Asp Ala Val Lys
            35                  40                  45
Gly Lys Cys Val Leu Phe Pro Tyr Gly Gly Cys Gln Gly Asn Gly Asn
        50                  55                  60
Lys Phe Tyr Ser Glu Lys Glu Cys Arg Glu Tyr
65                  70                  75
```

(2) INFORMATION FOR SEQ ID NO:97:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:97:

TGGATCCTAA CCGCAGTACT CTCTGCACTC                                    30

(2) INFORMATION FOR SEQ ID NO:98:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:98:

GTGACAAAGG CCAATCTCCC CATA                                          24

(2) INFORMATION FOR SEQ ID NO:99:

(i) SEQUENCE CHARACTERISTICS:
(A) LENGTH: 287 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 44..262

(xi) SEQUENCE DESCRIPTION: SEQ ID NO:99:

```
ACGCAAGTTC ACGTAAAAAG CTTAAAAAAG GGTATAAAAT AAA ATG AAA CAA AGT      55
                                             Met Lys Gln Ser
                                              1

ACT ATT GCA CTG GCA CTC TTA CCG TTA CTG TTT ACC CCT GTG ACA AAG     103
Thr Ile Ala Leu Ala Leu Leu Pro Leu Leu Phe Thr Pro Val Thr Lys
  5              10                  15                  20

GCC AAT CTC CCC ATA GTC CGG GGC CCC TGC CGA GCC TTC ATC CAG CTC     151
Ala Asn Leu Pro Ile Val Arg Gly Pro Cys Arg Ala Phe Ile Gln Leu
                 25                  30                  35

TGG GCA TTT GAT GCT GTC AAG GGG AAG TGC GTC CTC TTC CCC TAC GGG     199
```

|   |   |   |   |   |   |   |   |   |   |   |   |   |   |   |
|---|---|---|---|---|---|---|---|---|---|---|---|---|---|---|
| Trp | Ala | Phe | Asp<br>40 | Ala | Val | Lys | Gly | Lys<br>45 | Cys | Val | Leu | Phe | Pro<br>50 | Tyr Gly |

| GGC | TGC | CAG | GGC | AAC | GGG | AAC | AAG | TTC | TAC | TCA | GAG | AAG | GAG | TGC | AGA | 247 |
|-----|-----|-----|-----|-----|-----|-----|-----|-----|-----|-----|-----|-----|-----|-----|-----|-----|
| Gly | Cys | Gln<br>55 | Gly | Asn | Gly | Asn | Lys<br>60 | Phe | Tyr | Ser | Glu | Lys<br>65 | Glu | Cys | Arg |  |

| GAG | TAC | TGC | GGT | TAGGATCCTC | TACGCCGGAA | CGCATCGT |  | 287 |
|-----|-----|-----|-----|------------|------------|----------|--|-----|
| Glu | Tyr<br>70 | Cys | Gly |  |  |  |  |  |

( 2 ) INFORMATION FOR SEQ ID NO:100:

( i ) SEQUENCE CHARACTERISTICS:
        ( A ) LENGTH: 72 amino acids
        ( B ) TYPE: amino acid
        ( D ) TOPOLOGY: linear ( i i ) MOLECULE TYPE: protein ( x i ) SEQUENCE DESCRIPTION: SEQ ID NO:100:

| Met<br>1 | Lys | Gln | Ser | Thr<br>5 | Ile | Ala | Leu | Ala | Leu<br>10 | Leu | Pro | Leu | Leu | Phe<br>15 | Thr |
|---|---|---|---|---|---|---|---|---|---|---|---|---|---|---|---|
| Pro | Val | Thr<br>20 | Lys | Ala | Asn | Leu | Pro | Ile<br>25 | Val | Arg | Gly | Pro | Cys<br>30 | Arg | Ala |
| Phe | Ile | Gln<br>35 | Leu | Trp | Ala | Phe | Asp<br>40 | Ala | Val | Lys | Gly | Lys<br>45 | Cys | Val | Leu |
| Phe | Pro<br>50 | Tyr | Gly | Gly | Cys | Gln<br>55 | Gly | Asn | Gly | Asn | Lys<br>60 | Phe | Tyr | Ser | Glu |
| Lys<br>65 | Glu | Cys | Arg | Glu | Tyr<br>70 | Cys | Gly |  |  |  |  |  |  |  |  |

( 2 ) INFORMATION FOR SEQ ID NO:101:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:101:

CCTACGGGGG CTCTCAGGGC AACGG    25

( 2 ) INFORMATION FOR SEQ ID NO:102:

( i ) SEQUENCE CHARACTERISTICS:
        ( A ) LENGTH: 350 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 44..319

( x i ) SEQUENCE DESCRIPTION: SEQ ID NO:102:

| ACGCAAGTTC | ACGTAAAAAG | CTTAAAAAAG | GGTATAAAAT | AAA | ATG | AAA | CAA | AGT | 55 |
|---|---|---|---|---|---|---|---|---|---|
|  |  |  |  |  | Met<br>1 | Lys | Gln | Ser |  |

| ACT | ATT | GCA | CTG | GCA | CTC | TTA | CCG | TTA | CTG | TTT | ACC | CCT | GTG | ACA | AAG | 103 |
|---|---|---|---|---|---|---|---|---|---|---|---|---|---|---|---|---|
| Thr | Ile | Ala | Leu | Ala | Leu | Leu | Pro | Leu | Leu | Phe | Thr | Pro | Val | Thr | Lys |  |
|  | 5 |  |  |  | 10 |  |  |  |  | 15 |  |  |  |  | 20 |  |

| GCC | ACC | GTC | GCC | GCC | TGC | AAT | CTC | CCC | ATA | GTC | CGG | GGC | CCC | TGC | CGA | 151 |
|---|---|---|---|---|---|---|---|---|---|---|---|---|---|---|---|---|
| Ala | Thr | Val | Ala | Ala | Cys | Asn | Leu | Pro | Ile | Val | Arg | Gly | Pro | Cys | Arg |  |
|  |  |  |  | 25 |  |  |  |  | 30 |  |  |  |  | 35 |  |  |

```
GCC TTC ATC CAG CTC TGG GCA TTT GAT GCT GTC AAG GGG AAG TGC GTC      199
Ala Phe Ile Gln Leu Trp Ala Phe Asp Ala Val Lys Gly Lys Cys Val
             40                  45                  50

CTC TTC CCC TAC GGG GGC TCT CAG GGC AAC GGG AAC AAG TTC TAC TCA      247
Leu Phe Pro Tyr Gly Gly Ser Gln Gly Asn Gly Asn Lys Phe Tyr Ser
         55                  60                  65

GAG AAG GAG TGC AGA GAG TAC TGC GGT GTC CCT GGT GAT GGT GAT GAG      295
Glu Lys Glu Cys Arg Glu Tyr Cys Gly Val Pro Gly Asp Gly Asp Glu
         70                  75                  80

GAG CTG CTG CGC TTC TCC AAC TGACAACTGG ATCCTCTACG CCGGAACGCA         346
Glu Leu Leu Arg Phe Ser Asn
 85                  90

TCGT                                                                  350
```

(2) INFORMATION FOR SEQ ID NO:103:

(i) SEQUENCE CHARACTERISTICS:
        (A) LENGTH: 91 amino acids
        (B) TYPE: amino acid
        (D) TOPOLOGY: linear (ii) MOLECULE TYPE: protein (xi) SEQUENCE DESCRIPTION: SEQ ID NO:103:

```
Met Lys Gln Ser Thr Ile Ala Leu Ala Leu Leu Pro Leu Leu Phe Thr
 1               5                  10                  15

Pro Val Thr Lys Ala Thr Val Ala Ala Cys Asn Leu Pro Ile Val Arg
             20                  25                  30

Gly Pro Cys Arg Ala Phe Ile Gln Leu Trp Ala Phe Asp Ala Val Lys
         35                  40                  45

Gly Lys Cys Val Leu Phe Pro Tyr Gly Gly Ser Gln Gly Asn Gly Asn
     50                  55                  60

Lys Phe Tyr Ser Glu Lys Glu Cys Arg Glu Tyr Cys Gly Val Pro Gly
 65                  70                  75                  80

Asp Gly Asp Glu Glu Leu Leu Arg Phe Ser Asn
                 85                  90
```

(2) INFORMATION FOR SEQ ID NO:104:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:104:

```
TCAGAGAAGG AGTCTAGAGA GTACTGC                                         27
```

(2) INFORMATION FOR SEQ ID NO:105:

(i) SEQUENCE CHARACTERISTICS:
        (A) LENGTH: 350 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 44..319

(xi) SEQUENCE DESCRIPTION: SEQ ID NO:105:

```
ACGCAAGTTC ACGTAAAAAG CTTAAAAAAG GGTATAAAAT AAA ATG AAA CAA AGT       55
                                             Met Lys Gln Ser
```

```
ACT ATT GCA CTG GCA CTC TTA CCG TTA CTG TTT ACC CCT GTG ACA AAG    103
Thr Ile Ala Leu Ala Leu Leu Pro Leu Leu Phe Thr Pro Val Thr Lys
 5              10                  15                  20

GCC ACC GTC GCC GCC TGC AAT CTC CCC ATA GTC CGG GGC CCC TGC CGA    151
Ala Thr Val Ala Ala Cys Asn Leu Pro Ile Val Arg Gly Pro Cys Arg
                 25                  30                  35

GCC TTC ATC CAG CTC TGG GCA TTT GAT GCT GTC AAG GGG AAG TGC GTC    199
Ala Phe Ile Gln Leu Trp Ala Phe Asp Ala Val Lys Gly Lys Cys Val
             40                  45                  50

CTC TTC CCC TAC GGG GGC TGC CAG GGC AAC GGG AAC AAG TTC TAC TCA    247
Leu Phe Pro Tyr Gly Gly Cys Gln Gly Asn Gly Asn Lys Phe Tyr Ser
         55                  60                  65

GAG AAG GAG TCT AGA GAG TAC TGC GGT GTC CCT GGT GAT GGT GAT GAG    295
Glu Lys Glu Ser Arg Glu Tyr Cys Gly Val Pro Gly Asp Gly Asp Glu
     70                  75                  80

GAG CTG CTG CGC TTC TCC AAC TGACAACTGG ATCCTCTACG CCGGAACGCA       346
Glu Leu Leu Arg Phe Ser Asn
 85                  90

TCGT                                                                350
```

( 2 ) INFORMATION FOR SEQ ID NO:106:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:106:

```
Met Lys Gln Ser Thr Ile Ala Leu Ala Leu Leu Pro Leu Leu Phe Thr
 1               5                  10                  15

Pro Val Thr Lys Ala Thr Val Ala Ala Cys Asn Leu Pro Ile Val Arg
                 20                  25                  30

Gly Pro Cys Arg Ala Phe Ile Gln Leu Trp Ala Phe Asp Ala Val Lys
             35                  40                  45

Gly Lys Cys Val Leu Phe Pro Tyr Gly Gly Cys Gln Gly Asn Gly Asn
         50                  55                  60

Lys Phe Tyr Ser Glu Lys Glu Ser Arg Glu Tyr Cys Gly Val Pro Gly
 65                  70                  75                  80

Asp Gly Asp Glu Glu Leu Leu Arg Phe Ser Asn
                 85                  90
```

( 2 ) INFORMATION FOR SEQ ID NO:107:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:107:

```
Asp Asp Ala Ala Cys
 1               5
```

( 2 ) INFORMATION FOR SEQ ID NO:108:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: peptide (ix) FEATURE:
    (A) NAME/KEY: Modified-site
    (B) LOCATION: 1
    (D) OTHER INFORMATION: /note="Xaa-1 is selected from SEQ ID NO:20 to 24 and 107."

(ix) FEATURE:
    (A) NAME/KEY: Modified-site
    (B) LOCATION: 15
    (D) OTHER INFORMATION: /note="Xaa-2 is Gln or Lys."

(ix) FEATURE:
    (A) NAME/KEY: Modified-site
    (B) LOCATION: 42
    (D) OTHER INFORMATION: /note="Xaa-3 is Glu or Tyr."

(ix) FEATURE:
    (A) NAME/KEY: Modified-site
    (B) LOCATION: 51
    (D) OTHER INFORMATION: /note="Xaa-4 is selected from SEQ ID NOS:25 to 40."

(xi) SEQUENCE DESCRIPTION: SEQ ID NO:108:

```
Xaa Asn Leu Pro Ile Val Arg Gly Pro Cys Arg Ala Phe Ile Xaa Leu
 1               5                   10                  15
Trp Ala Phe Asp Ala Val Lys Gly Lys Cys Val Leu Phe Pro Tyr Gly
                20              25                  30
Gly Cys Gln Gly Asn Gly Asn Lys Phe Xaa Ser Glu Lys Glu Cys Arg
            35              40                  45
Gly Tyr Xaa
        50
```

PROTEASE INHIBITORY POLYPEPTIDES DERIVED FROM URINARY TRYPSIN INHIBITOR AND COMPOSITIONS THEREOF

FIELD OF THE INVENTION

This invention relates to a novel polypeptide, a DNA fragment which encodes the polypeptide, a vector containing the DNA, a transformant transformed with the DNA or the vector and a process for the production of the novel polypeptide. This invention also relates to a novel enzyme inhibition process, a novel drug composition making use of the polypeptide and methods of treating.

BACKGROUND OF THE INVENTION

As it is well known, various proteases, such as trypsin and chymotrypsin, play their roles in the body, and they take important roles in vivo such as digestion, defense mechanism, blood coagulation and fibrinolysis and the like. On the other hand, it has been revealed by previous studies that some diseases and syndromes are caused by abnormal activities of these proteases. For example, autolysis of the pancreas by abnormally activated trypsin is regarded as a cause of the onset of pancreatitis. Certain proteases such as elastase and tissue kallikrein which are leaked from disordered tissues, leucocytes and the like, as well as plasma proteases such as plasmin and plasma kallikrein, are taking part of the development of tissue degradation. In the events of shock, by proteases leaked from damaged cells, blood circulation in important organs is decreased and progressive functional disorders occur in these organs. In addition, it is considered that excess activation of proteases involved in blood coagulation is a direct cause of disseminated intravascular coagulation syndrome (DIC) which is often induced by several kinds of shocks, severe infectious diseases and the like.

In consequence, protease inhibitors which inhibit activities of the aforementioned proteases have been used in the treatment of diseases such as pancreatitis, shock, DIC, organ disorder and the like.

The protease inhibitors so far used as pharmaceuticals are divided into two groups, namely chemically synthesized compounds and natural substances. Typical examples of the former group include nafamostat mesilate and gabexate mesilate while the latter group includes aprotinin and urinary trypsin inhibitor (to be referred to as "UTI" hereinafter). Of these inhibitors, aprotinin is a protein purified from bovine lung and UTI is another protein purified from human urine.

Various types of proteinous protease inhibitors exist in the body, such as $\alpha 1$ antitrypsin and $\alpha 2$ macroglobulin. These proteinous protein inhibitors are considered to have a function to maintain homeostasis by regulating activities of proteases in vivo. Thus, it is expected that these proteinous protein inhibitors, when used as pharmaceuticals, will not only simply inhibit protease activities but also improve a disordered state. For example, it has been reported that the aforementioned aprotinin has an activity to improve liver function (Nakamura, T. et al., Kanzo, vol. 28, pp. 1257-1258, 1987) and that a urinary glycoproteinous protease inhibitor stimulates growth of blood vessel endothelial cells (Mckeehan, W. L., The Journal of Biological Chemistry, vol. 261, pp. 5378-5383, 1986). Because of such possible additional biological activities which cannot be found in chemically synthesized protease inhibitors, usefulness of these proteinous protease inhibitors as pharmaceuticals is evident.

The following describes properties of UTI.

UTI is a proteinous protease inhibitor initially purified from healthy human urine in accordance by the method of Proksch et al. (Proksch, G. J. et al., J. Lab. Clin. Med., vol. 79, pp. 491-499, 1972), with the molecular weight of about 67,000 by gel filtration (Sumi H. et al., J. Physiol. Soc. Japan, vol. 39, pp 59-61, 1977).

Various types of urinary trypsin inhibitors with different molecular weights have been reported. A typical well-studied example among these inhibitors is a proteinous protease inhibitor having a molecular weight of 30,000 which has been purified from human urine by Hochstrasser et al. who also have determined primary structure of the inhibitor (Hochstrasser et al., Hoppe-Seyler's Z. Physiol. Chem., vol. 362, pp. 1351-1355, 1981). According to Hochstrasser et al., this inhibitor is a protein composed of 143 amino acids having two active domains. Based on the secondary structure of these active domains, this inhibitor can be regarded as a member of the Kunitz-type protease inhibitors which also include aprotinin. It is also known that this inhibitor coincides with the light chain of a plasma protease inhibitor, inter-$\alpha$-trypsin inhibitor (to be referred to as "ITI" hereinafter) (Bourgunion, J. et al, Biochemical Biophysical Research Communications, vol. 131, pp. 1146-1153, 1985).

This inhibitor reported by Hochstrasser et al. is different from UTI in terms of their molecular weights, but their N-terminal sequence of 36 amino acids coincides with each other (Sumi, H. et al, Blood & Vessel, vol. 19, pp. 545-557, 1988). It has been suggested that the difference in molecular weights between these two urinary trypsin inhibitors may be due to difference in their sugar moiety contents (Shikimi, T., Pharma Medica, vol. 7, pp. 169-174, 1989).

Next, enzyme inhibition activities of UTI are described.

Based on the studies so far reported, it is evident that UTI shows the inhibition activities against many proteases such as trypsin, chymotrypsin, elastase, plasmin and the like (Ohnishi, H. et al., Folia Pharmacol. Japon, vol. 81, pp. 235-244, 1983). As described in the foregoing, however, there are no reports on its activity to inhibit plasma kallikrein. In addition, when the inventors of the present invention have conducted experiments on the inhibitory activities of UTI, it showed no plasma kallikrein-inhibiting activity. In the case of inhibition of an activated form of blood coagulation factor X (to be referred to as "FXa" hereinafter), it has been reported that a very high concentration of UTI slightly inhibited the activity of FXa (Fukutake, K., Folia Pharmacol, Japan, vol. 90, pp. 163-169, 1987) and that a very high concentration of UTI inhibited the FXa activity (Sakuragawa, N, et al., Saishin-igaku, vol. 42, pp. 820-830, 1987). According to experiments conducted by the present inventors, however, no FXa-inhibiting activity was found in UTI even at an extremely high concentration. Similar to the reports mentioned above, there are no reports on the activity of the 30,000 molecular weight protease inhibitor purified from human urine by Hochstrasser et al. to inhibit FXa or plasma kallikrein.

The C-terminal side domain of this inhibitor has been examined in detail in terms of its enzyme inhibition activities. Even in the case of this domain, there are no reports on its activity to inhibit FXa or plasma kallikrein, though it is known that this domain inhibits trypsin, chymotrypsin and plasmin (Albrecht, G. J. et al., *Hoppe-Seyler's Z. Physiol. Chem.*, vol. 364, pp. 1689–1696, 1983).

Attempts have been made to endow UTI with an additional inhibitory spectrum. For instance, Nishimaki et al. have prepared fragments of UTI by chemically modifying it with cyanogen bromide and cleaving its methionyl bond, and examined enzyme inhibiting activities of the resulting mixture of polypeptide fragments (Japanese Patent Publication No. 3-59079). Nishimaki et al., however, could not endow the fragments obtained by this process with an activity to inhibit FXa or plasma kallikrein.

As described in the foregoing, proteinous protease inhibitors have superior advantages as pharmaceuticals compared to chemically synthesized inhibitors. However, the currently used proteinous protein inhibitors as pharmaceuticals, namely aprotinin and UTI, have the following disadvantages.

In the case of aprotinin, it inhibits certain proteases such as trypsin, plasmin, kallikrein and the like (Yoshida, K. et al., *Nihon Rinsho*, vol. 48, pp. 165–172, 1990). Being bovine originated protein, however, it has a big possibility of causing anaphylactic shock because it shows antigenicity when non-orally administered to human, thus resulting in a serious problem in the case of its use as a pharmaceutical. In addition to this disadvantage, since related diseases due to protease activation are generally accompanied by the stimulation of blood coagulation in many cases, it is desirable that a protease inhibitor to be used for therapeutic purpose should possess the activity to inhibit a certain protease such as FXa which takes a main role in the blood coagulation cascade, in addition to its activities to inhibit other proteases such as trypsin and the like. However, we know of no report concerning the activity of aprotinin to inhibit FXa.

On the contrary, UTI is more preferable than aprotinin as a drug to be non-orally administered to human, because this protein is a human protein and therefore it shows no antigenicity against human. However, since UTI is a proteinous substance which is purified from human urine, it is difficult to obtain enough quantity of human urine when UTI is manufactured in a large scale. It is also difficult to produce this substance in a large quantity by means of genetic engineering techniques, because it has a large molecular weight and also is a glycoprotein. In addition, similar to the case of aprotinin, UTI has neither a FXa-inhibiting activity nor an activity to inhibit plasma kallikrein which is concerned in severe inflammation. In consequence, these proteinous protein inhibitors currently used as pharmaceuticals have many problems to be solved. It is necessary therefore to overcome these problems involved in the prior art by finding a novel substance which can inhibit disease-related proteases, as well as a process for the production of such a substance, thereby rendering possible treatment of diseases in which proteases are acting as key factors.

SUMMARY OF THE INVENTION

This invention contemplates overcoming problems involved in the native proteinous protein inhibitors which have been used as pharmaceuticals.

It is accordingly an object of the present invention to provide a novel polypeptide which has no antigenicity against human and high activities to inhibit many kinds of proteases including FXa and plasma kallikrein. Another object of the present invention is to provide a novel enzyme inhibition process, a novel method of treating and a novel drug composition making use of a polypeptide which has no antigenicity against human and high activities to inhibit many kinds of proteases including FXa and plasma kallikrein. The present invention also provides a DNA fragment containing a nucleotide sequence which encodes the novel polypeptide, a vector that comprises the DNA fragment and a transformant transformed with the DNA fragment or the vector, as well as a process for the production of the novel polypeptide.

This novel polypeptide comprises an amino acid sequence which coincides partially with the amino acid sequence of UTI. The novel polypeptide, as one of its functions, inhibits at least one of the enzymes consisting of trypsin, elastase, plasmin, plasma kallikrein and FXa. The novel polypeptide is suitable for its large scale production because it can be produced by genetic engineering techniques.

The novel enzyme inhibition process is a process to inhibit at least one of the enzymes consisting of trypsin, elastase, plasmin, plasma kallikrein and FXa, and the novel method of treating and the novel drug composition are useful for the treatment of diseases in which at least one of the enzymes such as trypsin, elastase, plasmin, plasma kallikrein and FXa is playing as a causal factor.

The inventors of the present invention have conducted intensive studies, with the aim of overcoming many problems involved in the prior art proteinous protease inhibitors which have been used as pharmaceuticals and of providing a novel enzyme inhibition process, a novel method of treating or a novel enzyme inhibitor. As a result of these efforts, the present inventors have accomplished the present invention based on the finding that a polypeptide containing an amino acid sequence which coincides partially with the amino acid sequence of UTI is possessed of a novel enzyme inhibition activity and that this novel polypeptide can be produced in a large scale.

According to a first aspect of the present invention, there is provided a novel polypeptide. The novel polypeptide of the first aspect of the present invention comprises an amino acid sequence which coincides partially with the amino acid sequence of UTI. This polypeptide having an amino acid sequence which coincides partially with the amino acid sequence of UTI, however, has not been recognized as a functional polypeptide. In consequence, the present invention discloses the polypeptide for the first time as a novel functional polypeptide, as well as its biological activities. The novel polypeptide of the present invention is suitable for a large scale production because it can be produced by genetic engineering techniques.

A second aspect of the present invention also provides a novel polypeptide. This novel polypeptide of the second aspect of the present invention is characterized in that it has a primary structure in which a specific amino acid in the novel polypeptide of the first aspect of the present invention is substituted by another amino acid, and that it has an higher FXa-inhibiting activity compared with the novel polypeptide of the first aspect of the present invention. This novel polypeptide is also suitable for a large scale production because it can be produced by genetic engineering techniques.

According to a third aspect of the present invention, there is provided a novel enzyme inhibition process which comprises using a polypeptide having an amino acid sequence that coincides partially with the amino acid sequence of UTI. The polypeptide to be used in this process also includes the novel polypeptides of the first and second aspect of the present invention. This process of the present invention has rendered to inhibit enzymes which could not be originally inhibited by UTI.

According to a fourth aspect of the present invention, there is provided a novel drug composition which comprises, as an active ingredient, a polypeptide having an amino acid sequence that coincides partially with the amino acid sequence of UTI. The novel polypeptides of the first and second aspect of the present invention are also included as the active ingredient of the drug composition of the present invention. The drug composition of the present invention has a new therapeutic effect which cannot be originally expected from the drug compositions containing UTI as the active ingredient.

A fifth aspect of the present invention provides a DNA fragment which comprises a nucleotide sequence that encodes the novel polypeptide of the first aspect of the present invention.

A sixth aspect of the present invention provides a DNA fragment which comprises a nucleotide sequence that encodes the novel polypeptide of the second aspect of the present invention.

A seventh aspect of the present invention provides a vector which comprises the DNA fragment of the fifth or a sixth aspect of the present invention.

A eighth aspect of the present invention provides a transformant transformed with the DNA fragment of the fifth or the sixth aspect of the present invention.

An ninth aspect of the present invention provides a transformant transformed with the vector of the sixth aspect of the present invention.

A tenth aspect of the present invention provides a process for the production of the novel polypeptide of the first or the second aspect of the present invention in which the DNA fragment of the fifth or the sixth aspect of the present invention and the transformant of the seventh aspect of the present invention are used.

A eleventh aspect of the present invention provides a process for the production of the novel polypeptide of the first or the second aspect of the present invention in which the DNA fragment of the fifth or the sixth aspect of the present invention, the vector of the seventh aspect of the present invention and the transformant of the eighth or the ninth aspect of the present invention are used.

A twelfth aspect of the present invention provides a method of treating in which a polypeptide comprising an amino acid sequence that coincides partially with the amino acid sequence of UTI is used. That is, it provides a method of treating which comprises using the drug composition of the fourth aspect of the present invention. The method of treating of the present invention can be applied to diseases and syndromes which cannot be essentially treated by administration of UTI because of it's protease inhibition spectrum.

Other objects and advantages of the present invention will be made apparent as the description progresses.

BRIEF DESCRIPTION OF THE DRAWINGS

FIG. 1 shows nucleotide sequences of oligonucleotides S33, S34, S35, S18, S19 and S20 (SEQ ID NOS: 63 to 68, respectively).

FIG. 2 shows a process for the construction of plasmid pM468.

FIG. 4A shows a nucleotide sequence (SEQ ID NO: 69) of sense primer, p-s01.

FIG. 4B shows a nucleotide sequence (SEQ ID NO: 71) of antisense primer, p-a01.

FIG. 5 shows a nucleotide sequence of linkers 2 (SEQ ID NO: 73) and 3 (SEQ ID NO: 74).

FIG. 7 shows a nucleotide sequence (SEQ ID NO: 75) of a region of plasmid pM552 from its HindIII recognition site to BamHI recognition site, and a corresponding amino acid sequence.

FIG. 8A shows a nucleotide sequence (SEQ ID NO: 77) of ScaI sense primer.

FIG. 8B shows a nucleotide sequence of (SEQ ID NO: 78) of antisense primer, p-a02.

FIG. 9A shows a nucleotide sequence (SEQ ID NO: 79) of HindIII sense primer.

FIG. 9B shows a nucleotide sequence (SEQ ID NO: 80) of antisense primer, p-a03.

FIG. 9C shows a nucleotide sequence (SEQ ID NO: 81) of BamHI antisense primer.

FIG. 11 shows a nucleotide sequence (SEQ ID NO: 82) of a region of plasmid pM560 from its HindIII recognition site to BamHI recognition site, and a corresponding amino acid sequence (SEQ ID NO: 83).

FIG. 12 shows a nucleotide sequence (SEQ ID NO: 84) of antisense primer, p-a04.

FIG. 13 shows a nucleotide sequence (SEQ ID NO: 85) of a region of plasmid pM551 from its HindIII recognition site to BamHI recognition site, and a corresponding amino acid sequence (SEQ ID NO: 86).

FIG. 14A shows human trypsin-inhibiting activity of polypeptide TN70 of the present invention obtained in Example 1-(5).

FIG. 14B shows human trypsin-inhibiting activity of polypeptide CC51 of the present invention obtained in Example 2-(5).

FIG. 15B shows human neutrophil elastase-inhibiting activity of polypeptide CC51 of the present invention obtained in Example 2-(5).

FIG. 15C shows human neutrophil elastase-inhibiting activity of polypeptide TL66 of the present invention obtained in Example 3-(4).

FIG. 17B shows human plasma kallikrein-inhibiting activity of polypeptide CC51 of the present invention obtained in Example 2-(5).

FIG. 17C shows human plasma kallikrein-inhibiting activity of polypeptide TL66 of the present invention obtained in Example 3-(4).

FIG. 21 shows a nucleotide sequence (SEQ ID NO: 88) of a region of plasmid pM575B from its HindIII recognition site to BamHI recognition site, and a corresponding amino acid sequence (SEQ ID NO: 89).

FIG. 24 shows a nucleotide sequence (SEQ ID NO: 92) of a region of plasmid pM576 from its HindIII recognition site to BamHI recognition site, and a corresponding amino acid sequence (SEQ ID NO: 93).

FIG. 28 shows a nucleotide sequence (SEQ ID NO: 95) of a region of plasmid pM564 from its HindIII recognition site to BamHI recognition site, and a corresponding amino acid sequence (SEQ ID NO: 96).

FIG. 29 shows a nucleotide sequence (SEQ ID NO: 97) of antisense primer, p-a07.

FIG. 30 shows a nucleotide sequence (SEQ ID NO: 98) of sense primer, p-s02.

FIG. 31 shows a nucleotide sequence (SEQ ID NO: 99) of a region of plasmid pM567 from its HindIII recognition site to BamHI recognition site, and a corresponding amino acid sequence (SEQ ID NO: 100).

FIG. 32 shows a nucleotide sequence (SEQ ID NO: 101) of sense primer, p-s03.

FIG. 33 shows a nucleotide sequence (SEQ ID NO: 102) of a region of plasmid pM568 from its HindIII recognition site to BamHI recognition site, and a corresponding amino acid sequence (SEQ ID NO: 103).

FIG. 34 shows a nucleotide sequence (SEQ ID NO: 104) of sense primer, p-s04.

FIG. 35 shows a nucleotide sequence (SEQ ID NO: 105) of a region of plasmid pM569 from its HindIII recognition site to BamHI recognition site, and a corresponding amino acid sequence (SEQ ID NO: 106).

DETAILED DESCRIPTION OF THE INVENTION

Figure 3:
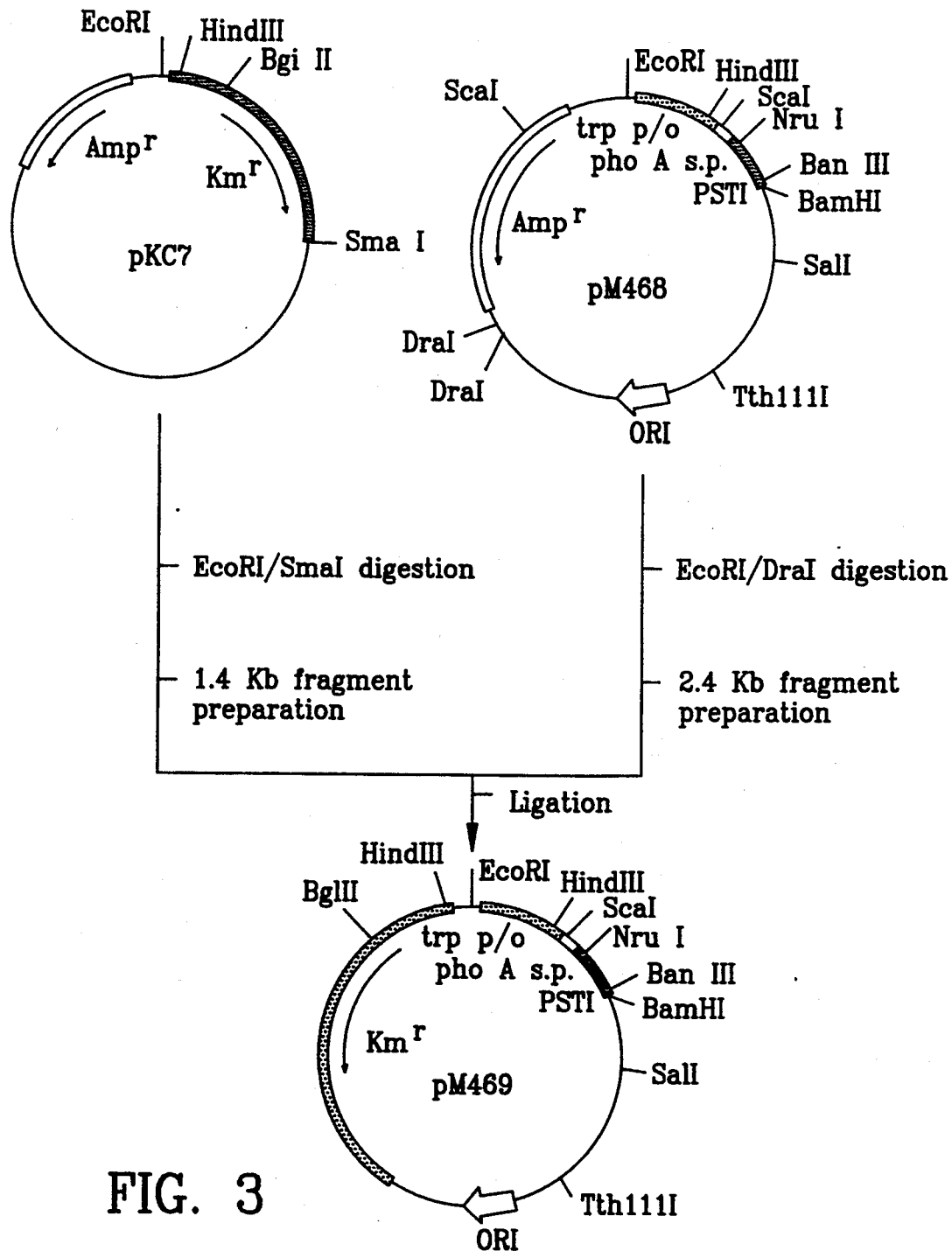
FIG. 3 shows a process for the construction of plasmid pM469.

According to a first aspect of the present invention, there is provided a novel polypeptide which comprises at least an amino acid sequence represented by the following formula 1. The polypeptide of the present invention has, as one of its functions, activities to inhibit trypsin, elastase, plasmin, plasma kallikrein and FXa.

Formula 1 (SEQ ID NO: 1)
Cys Asn Leu Pro Ile Val Arg Gly Pro Cys Arg Ala Phe
Ile Gln Leu Trp Ala Phe Asp Ala Val Lys Gly Lys Cys
Val Leu Phe Pro Tyr Gly Gly Cys Gln Gly Asn Gly Asn
Lys Phe Tyr Ser Glu Lys Glu Cys Arg Glu Tyr Cys The novel polypeptide of the first aspect of the present invention may be any polypeptide which is defined by any amino acid sequence without losing its characteristics as pharmaceuticals, provided that it contains the amino acid sequence of the formula 1 as a part of the amino acid sequence that defines primary structure of the polypeptide. In other words, the novel polypeptide may be either a polypeptide defined by the amino acid sequence of the formula 1 or a polypeptide in which optional one or more amino acids are added to the N-terminus and/or C-terminus of the formula 1 amino acid sequence. For example, it may be a polypeptide which contains at least an amino acid sequence represented by the formula 2. Preferably, the novel polypeptide of the present invention may be a polypeptide defined by the formula 2 amino acid.

Formula 2 (SEQ ID NO: 2)
X1 Asn Leu Pro Ile Val Arg Gly Pro Cys Arg Ala Phe
Ile Gln Leu Trp Ala Phe Asp Ala Val Lys Gly Lys Cys
Val Leu Phe Pro Tyr Gly Gly Cys Gln Gly Asn Gly Asn
Lys Phe Tyr Ser Glu Lys Glu Cys Arg Glu Tyr X2 wherein X1 is at least one amino acid sequence selected from the group consisting of the following formulae (1) to (5) (SEQ ID NOS: 20 to 24, respectively).
(1) The Val Ala Ala Cys
(2) Val Ala Ala Cys
(3) Ala Ala Cys
(4) Ala Cys
(5) Cys
and X2 is at least one amino acid sequence selected from the group consisting of the following formulae (6) (SEQ ID NOS: 25 to 40, respectively) to (21).
(6) Cys Gly Val Pro Gly Asp Gly Asp Glu Glu Leu Leu Arg Phe Ser Asn
(7) Cys Gly Val Pro Gly Asp Gly Asp Glu Glu Leu Leu Arg Phe Ser
(8) Cys Gly Val Pro Gly Asp Gly Asp Glu Glu Leu Leu Arg Phe
(9) Cys Gly Val Pro Gly Asp Gly Asp Glu Glu Leu Leu Arg
(10) Cys Gly Val Pro Gly Asp Gly Asp Glu Glu Leu Leu
(11) Cys Gly Val Pro Gly Asp Gly Asp Glu Glu Leu
(12) Cys Gly Val Pro Gly Asp Gly Asp Glu Glu
(13) Cys Gly Val Pro Gly Asp Gly Asp Glu
(14) Cys Gly Val Pro Gly Asp Gly Asp
(15) Cys Gly Val Pro Gly Asp Gly

(16) Cys Gly Val Pro Gly Asp
(17) Cys Gly Val Pro Gly
(18) Cys Gly Val Pro
(19) Cys Gly Val
(20) Cys Gly
(21) Cys in which a combination of the amino acid sequence (1) of the group X1 with the amino acid sequence (10) of the X2 group is excluded.

As a matter of course, X1 or X2 group in the above formula 2 is any one of the candidate amino acid sequences of the respective group. Any combination of X1 group amino acid sequences with those of X2 group may be used except for the aforementioned combination in which X1 is (1) and X2 is (10). A polypeptide defined by the amino acid sequence of this exceptional combination in which X1 is (1) and X2 is (10) has already been reported as an enzyme-digested fragment of a trypsin inhibitor purified from human urine by Hochstrasser et al. (Hochstrasser, K. et al., *Hoppe-Seyler's Z. Physiol. Chem.*, 360, S. pp. 1285-1296, 1979).

A preferred example of the novel polypeptide according to the first aspect of the present invention is a polypeptide defined by the amino acid sequence of the formula 2 wherein X1 is formula (5) and X2 is formula (21). In other words, such a preferred example of the novel polypeptide is a polypeptide defined by the amino acid sequence of the formula 1 itself. This polypeptide has, as one of its functions, activities to inhibit trypsin, elastase, plasmin, plasma kallikrein and FXa. It can be produced in a large scale by genetic engineering techniques. It has no antigenicity against human, because its primary structure coincides partially with the amino acid sequence of UTI and it has a low molecular weight. In addition, since this polypeptide has a low molecular weight, it can be used as a material for the preparation of fused protein for instance by fusing its N-terminus and/or C-terminus with other polypeptide having a different function.

An another preferred example of the novel polypeptide according to the first aspect of the present invention is a polypeptide defined by the amino acid sequence of the formula 2 wherein X1 is formula (1) and X2 is formula (6). In other words, such a preferred example of the novel polypeptide is a polypeptide defined by the amino acid sequence of the following formula 3.

Formula 3 (SEQ ID NO: 3)
Thr Val Ala Ala Cys Asn Leu Pro Ile Val Arg Gly Pro
Cys Arg Ala Phe Ile Gln Leu Trp Ala Phe Asp Ala Val
Lys Gly Lys Cys Val Leu Phe Pro Tyr Gly Gly Cys Gln
Gly Asn Gly Asn Lys Phe Tyr Ser Glu Lys Glu Cys Arg
Glu Tyr Cys Gly Val Pro Gly Asp Gly Asp Glu Glu Leu
Leu Arg Phe Ser Asn The polypeptide defined by the amino acid sequence of the above formula 3 has an amino acid sequence which coincides partially with the amino acid sequence of UTI, but the C-terminal side sequence of 4 amino acids, does not exist in the UTI amino acid sequence. This amino acid sequence represented by Arg-Phe-Ser-Asn is a sequence which has been revealed by the analysis of a gene encoding the aforementioned trypsin inhibitor purified from human urine by Hochstrasser et al. (Bourgunion,J. et a;., *Biochemical Biophysical Research Communications*, vol.131, pp.1146-1153, 1985). The existence of a natural polypeptide defined by the amino acid sequence of formula 3 having these 4 amino acids at its C-terminus has not been reported. Accordingly, this polypeptide is now disclosed by the present inventors for the first time as a functional polypeptide. This polypeptide has, as one of its functions, activities to inhibit trypsin, elastase, plasmin, plasma kallikrein and FXa. It can be produced in a large scale by genetic engineering techniques.

The novel polypeptide according to the first aspect of the present invention could contain sugar moieties.

The novel polypeptide according to the first aspect of the present invention can be obtained by any methods. For instance, it can be obtained by chemical synthesis using a peptide synthesizer (for example, model 431 A manufactured by Applied Biosystems) or the like. It can be obtained also by restricted cleavage of UTI obtained by purification from urine or ITI obtained by purification from blood, making use of some enzymes and the like. Preferably, however, the polypeptide can be prepared by genetic engineering techniques. More preferably, this polypeptide can be prepared by recombinant DNA techniques using *Escherichia coli* as a host.

A polypeptide can be easily chemically modified, maintaining substantially its inherent original activities. Consequently, the novel polypeptide of the first aspect of the present invention also includes chemically modified products prepared from the polypeptide defined by the amino acid sequence represented by the formula 1, 2 or 3, or the polypeptide which contains at least the amino acid sequence represented by the formula 1, 2 or 3 by means of sugar moieties addition, alkylation, oxidation, reduction, hydrolysis and the like. Also to be included are therapeutically acceptable acid or base salts of the just described inventive polypeptides.

In addition, primary structure of a polypeptide can be partly modified, maintaining substantially its inherent original activities. Consequently, the novel polypeptide of the first aspect of the present invention also includes derivative of a polypeptide defined by any one of the amino acid sequences represented by the formula 1, 2 and 3, or of a polypeptide which contains at least one of the amino acid sequences represented by the formula 1, 2 and 3, wherein such a polypeptide derivative comprises a modified amino acid sequence resulting from substitution, deletion, addition and the like of at least one amino acid at the N-terminus and/or C-terminus and/or inner part. Also to be included are chemically modified products prepared from these polypeptide derivatives by sugar moieties addition, alkylation, oxidation, reduction, hydrolysis and the like, as well as therapeutically acceptable acid or base salts of these polypeptide derivatives.

The inventors of the present invention have presumed that, since Cys molecules could form a S-S bond, these Cys molecules would be concerned in the formation of the three dimensional structure of the novel polypeptide in such a manner that it could exhibit its activity properly.

As shown in the later described Reference Examples 1, 2, 3 and 4, the present inventors have found that Cys contained in the polypeptide of the present invention is an important factor for the expression of the enzyme inhibition activities of the polypeptide.

In addition to the above assumption with regard to the effect of Cys, the present inventors have assumed that polypeptide derivatives resulting from substitution or deletion of other amino acids than Cys in the amino acid sequence represented by the formula 1, 2 or 3 and those resulting from addition of other amino acids than Cys to the amino acid sequence represented by the formula 1, 2 or 3 would exhibit similar activities to the polypeptide of the present invention.

By contraries, the present inventors have found that, as will be described in the following, several of such polypeptide derivatives can exhibit markedly high activities.

According to the present invention, a preferred example of such polypeptide derivatives with higher FXa-inhibiting activity is provided as a novel polypeptide of a second aspect of the invention.

The novel polypeptide of the second aspect of the present invention comprises an amino acid sequence which is derived from the foregoing amino acid sequence of formula 1 by substituting other amino acid for either of its 15th amino acid Gln and its 42nd amino acid Tyr counting from the N-terminal amino acid. That is, the novel polypeptide of the second aspect of the present invention comprises an amino acid sequence represented by the following formula 4.

Formula 4 (SEQ ID NO: 4)
Cys Asn Leu Pro Ile Val Arg Gly Pro Cys Arg
Ala Phe Ile Xaa-1 Leu Trp Ala Phe Asp Ala Val
Lys Gly Lys Cys Val Leu Phe Pro Tyr Gly Gly
Cys Gln Gly Asn Gly Asn Lys Phe Xaa-2 Ser Glu
Lys Glu Cys Arg Glu Tyr Cys wherein Xaa-1 is Gln or Lys and Xaa-2 is Tyr or Glu, provided that Xaa-2 is Glu when Xaa-1 is Gln, and Xaa-2 is Tyr when Xaa-1 is Lys.

Surprisingly, FXa-inhibiting activity of the polypeptide of the first aspect of the present invention becomes markedly higher by such amino acid substitution accomplished by the present inventors. As one of the characteristics, the novel polypeptide of the second aspect of the present invention is possessed of markedly higher FXa-inhibiting activity than that of the novel polypeptide of the first aspect of the present invention.

The novel polypeptide of the second aspect of the present invention may be any polypeptide which is defined by any amino acid sequence without losing its characteristics as pharmaceuticals, provided that it contains the amino acid sequence of the formula 4 as a part of the amino acid sequence that defines primary structure of the polypeptide. In other words, the novel polypeptide may be either a polypeptide defined by the amino acid sequence of the formula 4 or a polypeptide in which optional one or more amino acids are added to the N-terminus and/or C-terminus of the formula 4 amino acid sequence. For example, it may be a polypeptide which contains at least an amino acid sequence represented by the following formula 5 or 6. Preferably, the novel polypeptide of the second aspect of the present invention may be a polypeptide defined by the formula 5 amino acid sequence. Another preferred example of the novel polypeptide of the second aspect of the present invention is a polypeptide defined by the amino acid sequence of formula 6. Especially, since first and second N-terminal amino acids of the amino acid sequence represented by the formula 6 are both Asp, a polypeptide defined by this amino acid sequence can be excreted from host cells efficiently when it is produced in E. coli by recombinant DNA technology.

Formula 5 (SEQ ID NO: 5)
Thr Val Ala Ala Cys Asn Leu Pro Ile Val Arg Gly Pro
Cys Arg Ala Phe Ile Gln Leu Trp Ala Phe Asp Ala Val
Lys Gly Lys Cys Val Leu Phe Pro Tyr Gly Gly Cys Gln
Gly Asn Gly Asn Lys Phe Glu Ser Glu Lys Glu Cys Arg
Glu Tyr Cys Gly Val Pro Gly Asp Gly Asp Glu Glu Leu
Leu Arg Phe Ser Asn Formula 6 (SEQ ID NO: 6)
Asp Asp Ala Ala Cys Asn Leu Pro Ile Val Arg Gly Pro
Cys Arg Ala Phe Ile Lys Leu Trp Ala Phe Asp Ala Val
Lys Gly Lys Cys Val Leu Phe Pro Tyr Gly Gly Cys Gln
Gly Asn Gly Asn Lys Phe Tyr Ser Glu Lys Glu Cys Arg
Glu Tyr Cys Gly Val Pro Gly Asp Gly Asp Glu Glu Leu
Leu Arg Phe Ser Asn The novel polypeptide according to the second aspect of the present invention could contain sugar moieties.

A polypeptide can be chemically modified, maintaining substantially its inherent original activity. Consequently, the novel polypeptide of the second aspect of the present invention also includes chemically modified products prepared from the polypeptide defined by the amino acid sequence represented by the formula 4, 5 or 6, or the polypeptide which contains at least the amino acid sequence represented by the formula 4, 5 or 6 by sugar moiety addition, alkylation, oxidation, reduction, hydrolysis and the like. Also to be included are therapeutically acceptable acid or base salts of the just described inventive polypeptides.

In addition, primary structure of a polypeptide can be partly modified, maintaining substantially its inherent original activity. Consequently, the novel polypeptide of the second aspect of the present invention also includes a derivative of a polypeptide defined by any one of the amino acid sequences represented by the formula 4, 5 and 6, or of a polypeptide which contains at least one of the amino acid sequences represented by the formula 4, 5 and 6, wherein such a polypeptide derivative comprises a modified amino acid sequence resulting from substitution, deletion, addition and the like of at least one amino acid at the N-terminus and/or C-terminus and/or inner part. Also to be included are chemically modified products prepared from these polypeptide derivatives by sugar moiety addition, alkylation, oxidation, reduction, hydrolysis and the like, as well as therapeutically acceptable acid or base salts of these polypeptide derivatives.

The novel polypeptide according to the second aspect of the present invention can be obtained by any methods. For instance, it can be obtained by chemical synthesis using a peptide synthesizer or the like, referring the amino acid sequence represented by the formula 4, 5 or 6. Preferably, however, the polypeptide can be prepared by genetic engineering techniques. More preferably, this polypeptide can be prepared by a recombinant DNA technique using E. coli as a host.

According to a third aspect of the present invention, there is provided a novel enzyme inhibition process. This process comprises using a polypeptide containing an amino acid sequence which coincides partially with the amino acid sequence of UTI.

This novel enzyme inhibition process may be used for the inhibition of enzymes, preferably at least one enzyme selected from the group consisting of trypsin, elastase, plasmin, plasma kallikrein and FXa. The novel enzyme inhibition process is useful for the inhibition of any of these enzymes, but is more useful for the inhibition of at least one of plasma kallikrein and FXa.

According to the enzyme inhibition process of the present invention, in the case of an in vitro system, at least one polypeptide selected from the polypeptides as shown below is reacted with an enzyme or enzymes to be inhibited. In the case of an in vivo system, at least one of the following polypeptides is added to body fluid such as blood containing an enzyme or enzymes to be inhibited.

Polypeptides may be used alone or as a mixture of two or more.

As described above, the polypeptide to be used in the novel enzyme inhibition process of the present invention comprises an amino acid sequence which coincides partially with the amino acid sequence of UTI. Preferably, the polypeptide to be used in the novel enzyme inhibition process of the present invention may contain at least the amino acid sequence represented by the formula 1.

Formula 1 (SEQ ID NO: 1)
Cys Asn Leu Pro Ile Val Arg Gly Pro Cys Arg Ala Phe
Ile Gln Leu Trp Ala Phe Asp Ala Val Lys Gly Lys Cys
Val Leu Phe Pro Tyr Gly Gly Cys Gln Gly Asn Gly Asn
Lys Phe Tyr Ser Glu Lys Glu Cys Arg Glu Tyr Cys The polypeptide to be used in the enzyme inhibition process of the present invention may be any polypeptide which is defined by any amino acid sequence, provided that it contains the amino acid sequence of the formula 1 as a part of the amino acid sequence that defines primary structure of the polypeptide and that the enzyme inhibiting activities inherent to the polypeptide are not lost completely. For example, the polypeptide to be used may be a polypeptide which comprises at least an amino acid sequence represented by the following formula 7. In a preferred example of the novel enzyme inhibition process of the present invention, however, a polypeptide defined by the formula 7 may be used.

Formula 7 (SEQ ID NO: 7)
X1 Asn Leu Pro Ile Val Arg Gly Pro Cys Arg Ala Phe
Ile Gln Leu Trp Ala Phe Asp Ala Val Lys Gly Lys Cys
Val Leu Phe Pro Tyr Gly Gly Cys Gln Gly Asn Gly Asn
Lys Phe Tyr Ser Glu Lys Glu Cys Arg Glu Tyr X2 wherein X1 is an amino acid sequence selected from the following formulae (1) to (5) (SEQ ID NOS. 1 to 20, respectively)
(1) Thr Val Ala Ala Cys
(2) Val Ala Ala Cys
(3) Ala Ala Cys
(4) Ala Cys
(5) Cys
and X2 is an amino acid sequence selected from the following formulae (6) to (21) (SEQ ID NOS: 21 TO 36, respectively).
(6) Cys Gly Val Pro Gly Asp Gly Asp Glu Glu Leu Leu Arg Phe Ser Asn
(7) Cys Gly Val Pro Gly Asp Gly Asp Gly Alu Leu Leu Arg Phe Ser
(8) Cys Gly Val Pro Gly Asp Gly Asp Glu Glu Leu Leu Arg Phe
(9) Cys Gly Val Pro Gly Asp Gly Asp Glu Glu Leu Leu Arg
(10) Cys Gly Val Pro Gly Asp Gly Asp Glu Glu Leu Leu
(11) Cys Gly Val Pro Gly Asp Gly Asp Glu Glu Leu
(12) Cys Gly Val Pro Gly Asp Gly Asp Glu Glu
(13) Cys Gly Val Pro Gly Asp Gly Asp Glu
(14) Cys Gly Val Pro Gly Asp Gly Asp
(15) Cys Gly Val Pro Gly Asp Gly
(16) Cys Gly Val Pro Gly Asp
(17) Cys Gly Val Pro Gly
(18) Cys Gly Val Pro
(19) Cys Gly Val
(20) Cys Gly
(21) Cys As a matter of course, X1 or X2 group in the above formula 7 is any one of the candidate amino acid sequences of the representing group. In a preferred example of the novel enzyme inhibition process of the present invention, however, a polypeptide which is defined by an amino acid sequence based on the above formula 7 in which X1 is (5) and X2 is (21) may be used. Such a polypeptide is the same one as defined by the amino acid sequence of the formula 1 which is also a preferred example of the novel polypeptide of the first aspect of the present invention.

In another preferred example of the novel enzyme inhibition process of the present invention, a polypeptide which is defined by an amino acid sequence based on the above formula 7 in which X1 is (1) and X2 is (6) may be used. Such a polypeptide is the same one as defined by the amino acid sequence of the foregoing formula 3 which is also a preferred example of the novel polypeptide of the first aspect of the present invention.

In more another preferred example of this process of the present invention, a polypeptide which is defined by an amino acid sequence based on the above formula 7 in which X1 is (1) and X2 is (10) may be used. Such a polypeptide is the one defined by an amino acid sequence of the following formula 8.

Formula 8 (SEQ ID NO: 8)
Thr Val Ala Ala Cys Asn Leu Pro Ile Val Arg Gly Pro
Cys Arg Ala Phe Ile Gln Leu Trp Ala Phe Asp Ala Val
Lys Gly Lys Cys Val Leu Phe Pro Tyr Gly Gly Cys Gln
Gly Asn Gly Asn Lys Phe Tyr Ser Glu Lys Glu Cys Arg
Glu Tyr Cys Gly Val Pro Gly Asp Gly Asp Glu Glu Leu
Leu As described in the foregoing, the polypeptide defined by the amino acid sequence of the above formula 8 has already been recognized as an enzyme-digested fragment of a trypsin inhibitor purified from human urine (Hochstrasser, K. et al., *Hoppe-Sayler's Z. Physiol. Chem.*, pp. 1285-1296, 1979). This polypeptide has been reported as a substance having activities to inhibit trypsin, chymotrypsin and plasmin, but with no reports about its activities to inhibit plasma kallikrein and FXa. In consequence, the kallikrein- and FXa-inhibiting activities of this polypeptide have been discovered for the first time by the present inventors.

The polypeptide to be used in the novel enzyme inhibition process of the present invention may be obtained by any methods. For instance, it can be obtained by chemical synthesis using a peptide synthesizer or the like. It can be obtained also by restricted cleavage of UTI obtained by purification from urine or ITI obtained by purification from plasma, making use of enzymes. Preferably, however, the polypeptide can be prepared by genetic engineering techniques. More preferably, this polypeptide can be prepared by a recombinant DNA technology using *E. coli* as a host.

A polypeptide can be chemically modified, maintaining substantially its inherent original activities. Consequently, the polypeptide to be used in the novel enzyme inhibition process of the third aspect of the present invention also includes chemically modified products prepared from the polypeptide defined by the amino acid sequence represented by the foregoing formula 1, 3, 7 or 8 or the polypeptide which contains at least the amino acid sequence represented by the formula 1, 3, 7 or 8 by sugar moiety addition, alkylation, oxidation, reduction, hydrolysis and the like. Also to be included are therapeutically acceptable acid or base salts of the just described inventive polypeptides.

In addition, primary structure of a polypeptide can be partly modified, maintaining substantially its inherent original activities. Consequently, the polypeptide to be used in the novel enzyme inhibition process of the third aspect of the present invention also includes a derivative of a polypeptide defined by any one of the amino acid sequences represented by the formula 1, 3, 7 and 8, or of a polypeptide which contains at least one of the amino acid sequences represented by the formula 1, 3, 7 and 8, wherein such a polypeptide derivative comprises a modified amino acid sequence resulting from substitution, deletion, addition and the like of at least one amino acid at the N-terminus and/or C-terminus and/or inner part. Also to be included are chemically modified products prepared from these polypeptide derivatives by sugar moiety addition, alkylation, oxidation, reduction, hydrolysis and the like, as well as therapeutically acceptable acid or base salts of these polypeptide derivatives.

Among these processes for the inhibition of enzymes making use of such polypeptide derivatives, a preferred example is a process in which the novel polypeptide of the second aspect of the present invention is used because of the function of the polypeptide to inhibit FXa. Another preferred process for the inhibition of enzymes making use of the polypeptide derivative is a one to which a polypeptide defined by the amino acid sequence of the formula 5 is applied. Still another preferred example of the process is a one in which a polypeptide defined by the amino acid sequence represented by the formula 6 is used.

The enzyme inhibition process which comprises using the polypeptide defined by the amino acid sequence of the formula 5 or 6 is useful for the inhibition of at least one enzyme selected from the group consisting of trypsin, elastase, plasmin, plasma kallikrein and FXa, and has higher FXa-inhibiting activity than another process in which a polypeptide defined by the amino acid sequence of the foregoing formula 1, 3, 7 or 8.

The polypeptide to be used in the enzyme inhibition process may be obtained by any methods. For instance, it can be obtained by chemical synthesis using a peptide synthesizer or the like by referring of the amino acid sequence represented by the formula 5 or 6. Preferably, however, the polypeptide can be prepared by genetic engineering techniques. More preferably, this polypeptide can be prepared by a recombinant DNA technology using $E.$ $coli$ as a host.

As a matter of course, such polypeptide derivative-aided enzyme inhibition processes include not only a process in which the polypeptide defined by the amino acid sequence represented by the formula 5 or 6 is used, but also a process which is effected by the use of a polypeptide derivative that comprises a modified amino acid sequence resulting from substitution, deletion, addition and the like of at least one amino acid at the N-terminus and/or C-terminus and/or inner part of the amino acid sequence of the formula 5 or 6. Also useful in the novel enzyme inhibition process of the present invention are chemically modified products of the polypeptide defined by the amino acid sequence of the formula 5 or 6, which are obtained by various techniques such as sugar moiety addition, alkylation, oxidation, reduction, hydrolysis and the like, as well as other materials obtained by making the polypeptide into salts of therapeutically acceptable acids or bases. Also useful are chemically modified products of a polypeptide obtained by various techniques such as sugar moiety addition, alkylation, oxidation, reduction, hydrolysis and the like, and therapeutically acceptable acid or base salts thereof, wherein said polypeptide comprises an amino acid sequence resulting from substitution, deletion, addition and the like of at least one amino acid at the N-terminus and/or C-terminus and/or inner part of the amino acid sequence of the formula 5 or 6.

According to a fourth aspect of the present invention, there is provided a drug composition. The drug composition of the present invention comprises a polypeptide having an amino acid sequence which coincides partially with the amino acid sequence of UTI.

The drug composition of the present invention may be used preferably for the purpose of preventing and/or treating diseases in which at least one enzyme of the group consisting of trypsin, elastase, plasmin, plasma kallikrein and FXa is concerned. More preferably, the drug composition may be used for the purpose of preventing and/or treating diseases in which at least one of the enzymes, plasma kallikrein and FXa, is concerned. In other words, the drug composition of the present invention is used for the purpose of preventing and/or treating at least one disease selected from the group consisting of operative stress, multiple organ failure, shock, pancreatitis, disseminated intravascular coagulation syndrome, ischemic heart disease, nephritis, hepatic cirrhosis, thrombosis after revascularization, edema caused by increased vascular permeability, adult respiratory distress syndrome, rheumatoid arthritis, arthritis and allergy.

Since the drug composition of the present invention has an effect to inhibit blood coagulation as one of its characteristics, it may be used for the prevention and/or treatment of disseminated intravascular coagulation syndrome. It may be used as a blood coagulation inhibitor for the purpose of inhibiting blood coagulation against any diseases. In addition to its effects on these diseases, it is expected that the drug composition of the present invention will affect to a substance or a biological molecule having similar structure to at least one of the enzyme group consisting of trypsin, elastase, plasmin, plasma kallikrein and FXa, thereby modifying and inhibiting functions of the substance or biological molecule.

The polypeptide to be used as an active ingredient of the drug composition of the fourth aspect of the present invention is the same polypeptide to be used in the enzyme inhibition process of the third aspect of the present invention. They have been described already.

Though it is possible to provide the medical field with fully effective drug composition of the present invention even if the drug composition is composed solely of the polypeptide of the first or the second aspect of the present invention (for example, an article of the polypeptide processed through necessary steps such as freeze drying, sterile filtration and the like), the drug composition may further contain therapeutically acceptable auxiliary components.

Such auxiliary components to be included in the drug composition of the present invention are a base, a stabilizer, an antiseptic agent, preservation agent, an emulsifying agent, a suspending agent, a solvent, a solubilizing agent, a lubricant, a corrective agent, a coloring agent, an aromatic agent, a soothing agent, an excipient, a binder, a thickening agent, a buffer and the like. Illustrative examples of these auxiliary components include calcium carbonate, lactose, sucrose, sorbitol, mannitol, starch, amylopectin, cellulose derivatives, gelatin, cacao butter, distilled water for injection use, sodium chloride solution, Ringer solution, glucose solution, human serum albumin (HSA) and the like. The amount of these components may be determined depending on each dosage form within a therapeutically acceptable range.

Dose of the drug composition of the present invention may vary depending on the content of active ingredient and conditions, age, sex, weight and the like of each patient to be treated. Preferably, however, the drug composition of the present invention may be administered in an amount of from 0.1 to 1,000 mg/kg, more preferably from 0.2 to 50 mg/kg, as the amount of the active agent.

The drug composition of the present invention can be administered by various means depending on the conditions of each patient, such as oral administration, intramuscular injection, intraperitoneal administration, intradermal injection, subcutaneous injection, intravenous injection, intraarterial administration, rectal administration and the like, as well as inhalation of the drug composition making it into an aerosol form, of which intravenous injection is particularly preferred.

In addition to its effects on the aforementioned diseases, it is expected that the drug composition of the present invention will affect to a substance or a biological molecule having similar structure to at least one of the enzyme group consisting of trypsin, elastase, plasmin, plasma kallikrein and FXa, thereby inhibiting functions of the substance or biological molecule. And the drug composition of the present invention may be used by immobilizing in and/or on artificial vessel, artificial organ, medical device such as catheter and the like.

According to a fifth aspect of the present invention, there is provided a DNA fragment which comprises a nucleotide sequence that encodes the novel polypeptide of the first aspect of the present invention.

The DNA fragment of the fifth aspect of the present invention comprises a nucleotide sequence which coincides partially with an already reported nucleotide sequence (Kaumeyer, J. F. et al., *Nucleic Acids Res.*, vol. 14, pp. 7839–7850) that encodes the aforementioned protein purified from human urine by Hochstrasser et al. However, this DNA fragment has been disclosed by the present inventors for the first time as a DNA fragment encoding the novel polypeptide of the first aspect of the present invention which is a functional polypeptide unit.

The DNA fragment of the present invention may comprise any nucleotide sequence, provided that, when appropriate host cells are transformed with the DNA fragment of the present invention by transforming with the fragment into the cells by an appropriate method, the novel polypeptide of the first aspect of the present invention is expressed in the thus transformed host cells. Preferably, the DNA fragment may comprise at least a nucleotide sequence represented by the following formula 9 as a part of the DNA nucleotide sequence.

Formula 9 (SEQ ID NO: 9)
```
TGC AAT CTC CCC ATA GTC CGG GGC CCC TGC CGA
GCC TTC ATC CAG CTC TGG GCA TTT GAT GCT GTC
AAG GGG AAG TGC GTC CTC TTC CCC TAC GGG GGC
TGC CAG GGC AAC GGG AAC AAG TTC TAC TCA GAG
AAG GAG TGC AGA GAG TAC TGC
```

When a well known fact that a degeneracy of codon correspond to one amino acid is taken into consideration, the DNA fragment of the fifth aspect of the present invention may comprise a derivative of the nucleotide sequence of the formula 9 in which at least one nucleotide is substituted by other nucleotide.

In addition to the nucleotide sequence represented by the formula 9, the DNA fragment of the fifth aspect of the present invention may comprise a nucleotide sequence resulting from the addition of at least one nucleotide to the 5'-end and/or the 3'-end of the formula 9 nucleotide sequence. Also, in addition to a derivative of the nucleotide sequence represented by the formula 9 in which at least one nucleotide is substituted by other nucleotide, the DNA fragment of the fifth aspect of the present invention may comprise a nucleotide sequence resulting from the addition of at least one nucleotide to the 5'-end and/or the 3'-end of the derivative of the formula 9 nucleotide sequence.

Any nucleotide or polynucleotide may be used as a member to be added, provided that its addition does not cause changes in the amino acid sequence encoded by the nucleotide sequence represented by the formula 9. For example, the DNA fragment of the fifth aspect of the present invention may comprise not only the nucleotide sequence of the formula 9 or a derivative of the formula 9 nucleotide sequence in which at least one nucleotide is substituted by other nucleotide, but also a nucleotide sequence resulting from the addition of ATG as an initiation codon to the 5'end of the inventive nucleotide sequence or its derivative or another nucleotide sequence resulting from the addition of TAA, TAG or TGA to the 3'-end as a termination codon. In addition, the DNA fragment of the present invention may, if necessary, have restriction endonuclease recognition sites on its 5'-end and/or 3'-end. Also, the DNA fragment of the present invention may comprise not only the nucleotide sequence of the formula 9 or a derivative of the formula 9 nucleotide sequence in which at least one nucleotide is substituted by other nucleotide, but also a nucleotide sequence resulting from the addition of another nucleotide sequence encoding different amino acids to the 5'end and/or 3'-end of the inventive nucleotide sequence or its derivative. For example, the DNA fragment of the present invention may be made into a form of fused gene by adding to its 5'-end and/or 3'-end a nucleotide sequence which encodes a different polypeptide useful for the production of the polypeptide of the present invention.

A preferred example of the DNA fragment of the fifth aspect of the present invention in which a different nucleotide sequence is added to the 5'-end and/or 3'-end of the nucleotide sequence of formula 9 is a DNA fragment which comprises a nucleotide sequence represented by the following formula 10. More preferable example may be a DNA fragment which is defined by the formula 10.

Formula 10 (SEQ ID NO: 10)
```
Y1  AAT CTC CCC ATA GTC CGG GGC CCC TGC CGA
GCC TTC ATC CAG CTC TGG GCA TTT GAT GCT GTC
AAG GGG AAG TGC GTC CTC TTC CCC TAC GGG GGC
TGC CAG GGC AAC GGG AAC AAG TTC TAC TCA GAG
AAG GAG TGC AGA GAG TAC Y2
``` wherein Y1 is a nucleotide sequence selected from the following formulae (1) to (6) (SEQ ID NOS: 41 to 46, respectively)
(1) ACT GTG GCG GCC TGC
(2) ACC GTC GCC GCC TGC
(3) GTC GCC GCC TGC
(4) GCC GCC TGC
(5) GCC TGC
(6) TGC
and Y2 is a nucleotide sequence selected from the following formulae (7) to (22) (SEQ ID NOS: 47 to 62, respectively)
(7) TGC GGT GTC CCT GGT GAT GGT GAT GAG GAG CTG CTG CGC TTC TCC AAC
(8) TCG GGT GTC GGT GAT GGT GAT GAG GAG CTG CTG CGC TTC TCC
(9) TGC GGT GTC CCT GGT GAT GGT GAT GAG GAG CTG CTG CGC TTC
(10) TGC GGT GTC CCT GGT GAT GGT GAT GAG GAG CTG CTG CGC
(11) TGC GGT GTC CCT GGT GAT GGT GAT GAG GAG CTG CTG
(12) TGC GGT GTC CCT GGT GAT GGT GAT GAG GAG CTG
(13) TGC GGT GTC CCT GGT GAT GGT GAT GAG GAG
(14) TGC GGT GTC CCT GGT GAT GGT GAT GAG
(15) TGC GGT GTC CCT GGT GAT GGT GAT
(16) TGC GGT GTC CCT GGT GAT GGT
(17) TGC GGT GTC CCT GGT GAT
(18) TGC GGT GTC CCT GGT
(19) TGC GGT GTC CCT
(20) TGC GGT GTC
(21) TGC GGT
(22) TGC In the formula 10, each of Y1 and Y2 may be any nucleotide sequence selected from the candidate sequences, and combination of Y1 with Y2 is not particularly limited.

Preferably, however, the DNA fragment of the present invention may be defined by the nucleotide sequence of formula 10 in which Y1 is (6) and Y2 is (22). In other words, such a preferred DNA fragment is the fragment defined by the aforementioned nucleotide sequence of formula 9.

Another preferable example of the DNA fragment of the present invention is a fragment defined by the nucleotide sequence of formula 10 in which Y1 is (2) and Y2 is (7), that is a nucleotide sequence represented by the following formula 11.

Formula 11 (SEQ ID NO: 11)
```
ACC GTC GCC GCC TGC AAT CTC CCC ATA GTC CGG
GGC CCC TGC CGA GCC TTC ATC CAG CTC TGG GCA
TTT GAT GCT GTC AAG GGG AAG TGC GTC CTC TTC
CCC TAC GGG GGC TGC CAG GGC AAC GGG AAC AAG
TTC TAC TCA GAG AAG GAG TGC AGA GAG TAC TGC
GGT GTC CCT GGT GAT GGT GAT GAG GAG CTG CTG
CGC TTC TCC AAC
```

Still another preferable example of the DNA fragment of the present invention is a fragment defined by the nucleotide sequence of formula 10 in which Y1 is (2) and Y2 is (11), that is a nucleotide sequence represented by the following formula 12.

Formula 12 (SEQ ID NO: 12)
```
ACC GTC GCC GCC TGC AAT CTC CCC ATA GTC CGG
GGC CCC TGC CGA GCC TTC ATC CAG CTC TGG GCA
TTT GAT GCT GTC AAG GGG AAG TGC GTC CTC TTC
CCC TAC GGG GGC TGC CAG GGC AAC GGG AAC AAG
TTC TAC TCA GAG AAG GAG TGC AGA GAG TAC TGC
GGT GTC CCT GGT GAT GGT GAT GAG GAG CTG CTG
```

According to an sixth aspect of the present invention, there is provided a DNA fragment which comprises a nucleotide sequence that encodes the novel polypeptide of the second aspect of the present invention.

The DNA fragment of the present invention may comprise any nucleotide sequence, provided that, when appropriate host cells are transformed with the DNA fragment of the present invention by transforming with the fragment into the cells by an appropriate method, the novel polypeptide of the second aspect of the present invention is expressed in the thus transformed host cells. Preferably, the DNA fragment may comprise at least a nucleotide sequence represented by the following formula 13 as a part of the DNA nucleotide sequence.

Formula 13 (SEQ ID NO: 13)
```
TGC AAT CTC CCC ATA GTC CGG GGC CCC TGC CGA
GCC TTC ATC NNN-1 CTC TGG GCA TTT GAT GCT GTC
AAG GGG AAG TGC GTC CTC TTC CCC TAC GGG GGC
TGC CAG GGC AAC GGG AAC AAG TTC NNN-2 TCA GAG
```

AAG GAG TGC AGA GAG TAC TGC wherein NNN-1 is CAG or AAG and NNN-2 is TAC or GAA, provided that NNN-2 is GAA when NNN-1 is CAG and NNN-2 is TAC when NNN-1 is AAG.

When a well known fact that a degeneracy of codon correspond to one amino acid is taken into consideration, the DNA fragment of the eleventh aspect of the present invention may comprise a derivative of the nucleotide sequence of the formula 13 in which at least one nucleotide is substituted by other nucleotide.

The DNA fragment of the present invention may comprise a nucleotide sequence resulting from the addition of at least one nucleotide to the 5'-end and/or the 3'-end of the formula 13 nucleotide sequence represented by the above formula 13 in which at least one nucleotide is substituted by other nucleotide, the DNA fragment of the present invention may comprise a nucleotide sequence resulting from the addition of at least one nucleotide to the 5'-end and/or the 3'-end of the derivative of the formula 13 nucleotide sequence.

Any nucleotide or polynucleotide sequence may be used as a member to be added, provided that its addition does not cause changes in the amino acid sequence encoded by the nucleotide sequence represented by the formula 13. For example, the DNA fragment of the present invention may comprise not only the nucleotide sequence of the formula 13 or a derivative of the formula 13 nucleotide sequence in which at least one nucleotide is substituted by other nucleotide, but also a nucleotide sequence resulting from the addition of ATG as an initiation codon to the 5'end of the inventive nucleotide sequence or its derivative or another nucleotide sequence resulting from the addition of TAA, TAG or TGA to the 3'-end as a termination codon. In addition, the DNA fragment of the present invention may, if necessary, have restriction endonuclease recognition sites on its 5'-end and/or 3'-end. Also, the DNA fragment of the present invention may comprise not only the nucleotide sequence of the formula 13 or a derivative of the formula 13 nucleotide sequence in which at least one nucleotide is substituted by other nucleotide, but also a nucleotide sequence resulting from the addition of another nucleotide sequence encoding different amino acids to the 5'end and/or 3'-end of the inventive nucleotide sequence or its derivative. For example, the DNA fragment of the present invention may be made into a form of fused gene by adding to its 5'-end and/or 3'-end a nucleotide sequence which encodes a different polypeptide useful for the production of the polypeptide of the present invention.

A preferred example of the DNA fragment of the sixth aspect of the present invention in which a different nucleotide sequence is added to the 5'-end and/or 3'-end of the nucleotide sequence of formula 13 is a DNA fragment which is defined by a nucleotide sequence represented by the following formula 14.

Formula 14 (SEQ ID NO: 14)
```
ACC GTC GCC GCC TGC AAT CTC CCC ATA GTC CGG
GGC CCC TGC CGA GCC TTC ATC CAG CTC TGG GCA
TTT GAT GCT GTC AAG GGG AAG TGC GTC CTC TTC
CCC TAC GGG GGC TGC CAG GGC AAC GGG AAC AAG
TTC GAA TCA GAG AAG GAG TGC AGA GAG TAC TGC
GGT GTC CCT GGT GAT GGT GAT GAG GAG CTG CTG
CGC TTC TCC AAC
```

Another preferred example of the present invention is a DNA fragment which is defined a nucleotide sequence represented by the following formula 15

Formula 15 (SEQ ID NO: 15)
```
GAC GAC GCC GCC TGC AAT CTC CCC ATA GTC CGG
GGC CCC TGC CGA GCC TTC ATC AAG CTC TGG GCA
TTT GAT GCT GTC AAG GGG AAG TGC GTC CTC TTC
CCC TAC GGG GGC TGC CAG GGC AAC GGG AAC AAG
TTC TAC TCA GAG AAG GAG TGC AGA GAG TAC TGC
GGT GTC CCT GGT GAT GGT GAT GAG GAG CTG CTG
CGC TTC TCC AAC
```

As mentioned in the foregoing, when a fact that a degeneracy of codon correspond to one amino acid is taken into consideration, the DNA fragment of the fifth aspect of the present invention may also include a DNA fragment which is defined by a derivative of the nucleotide sequence of the formula 10, 11, 12, 13, 14 or 15, in which at least one nucleotide is substituted by other nucleotide.

In addition to the nucleotide sequence represented by the above formula 10, 11, 12, 13, 14 or 15, the DNA fragment of the fifth or sixth aspect of the present invention may also include a DNA fragment which comprises a nucleotide sequence resulting from the addition of at least one nucleotide to the 5'-end and/or the 3'-end of the nucleotide sequence of formula 10, 11, 12, 13, 14 or 15. Also, in addition to the nucleotide sequence resulting from the addition of at least one nucleotide to the nucleotide sequence of formula 10, 11, 12, 13, 14 or 15, the DNA fragment of the fifth or sixth aspect of the present invention may also include a DNA fragment which comprises a nucleotide sequence resulting from the addition of at least one nucleotide sequence to the 5'-end and/or the 3'-end of the polynucleotide sequence. A nucleotide or a nucleotide sequence to be added is not particularly limited, provided that its addition does not cause changes in the amino acid sequence encoded by the nucleotide sequence represented by the formula 10, 11, 12, 13, 14 or 15. Examples of such bases and polynucleotide to be added include an initiation codon, a termination codon, a restriction endonuclease recognition site, a nucleotide sequence encoding different amino acids or polypeptide, and any other nucleotide and polynucleotide.

The DNA fragment of the present invention may be obtained by any methods. For example, it may be obtained by chemical synthesis by referring the formula 9, 10, 11, 12, 13, 14 or 15, or by making use of recombinant DNA techniques using an appropriate chromosomal DNA library or cDNA library as a starting material.

Chemical synthesis of the DNA fragment of the fifth aspect of the present invention may be effected for example in the following manner. Firstly, a desired DNA fragment having a nucleotide sequence which encodes the novel polypeptide of the first aspect of the present invention is designed and, if necessary, the designed DNA fragment is divided into appropriate size of small fragments. An oligomer which corresponds to the DNA fragment or each of its divided fragments is synthesized using a fully automatic DNA synthesizer (for example, model 380A manufactured by Applied Biosystems). The synthesized DNA oligomer is subjected to annealing. If necessary, 5'-end phosphorization is carried out using T4 polynucleotide kinase prior to the annealing step. Thereafter, each annealed fragment is subjected to ligation with T4 DNA ligase and the like if necessary, and then cloned into an appropriate vector.

When the DNA fragment of the present invention is prepared by means of recombinant DNA techniques, the following procedure may be carried out. Firstly, chemical synthesis is carried out in order to obtain a DNA fragment having a nucleotide sequence which corresponds to entire portion or a part of the amino acid sequence of the novel polypeptide of the first aspect of the present invention. Thereafter, using the synthesized DNA fragment as a probe, hybridization is carried out making use of an appropriate cDNA library or chromosomal DNA library by usual methods to obtain the DNA fragment of the present invention (cf. Wallace, R. B. et al., *Nucleic Acid Res.*, vol. 9, pp. 879–894, 1981, as an example of the hybridization method). Alternatively, chemical synthesis is carried out in order to obtain DNA fragments having nucleotide sequences which correspond to N-terminal and C-terminal amino acid sequences of the amino acid sequence of the novel polypeptide of the first aspect of the present invention. Thereafter, using the synthesized DNA fragments as primers, polymerase chain reaction (to be referred to as "PCR" hereinafter) is carried out making use of an appropriate cDNA library or chromosomal DNA library to obtain the DNA fragment of the present invention (cf. *PCR Protocols, A Guide to Methods and Applications*, edited by Michael, A. I. et al., Academic Press, 1990). A cDNA library or a chromosomal DNA library to be used may be chosen from commercially available ones, or prepared from appropriate tissues or cells according to usual methods (cf. *Molecular Cloning, A Laboratory Manual*, edited by T. Maniatis et al., Cold Spring Harbor Laboratory, 1982).

Similar to the case of the DNA fragment of the fifth aspect of the present invention, the DNA fragment of the sixth aspect of the present invention may be obtained by any methods. For example, it may be obtained by chemical synthesis by referring of the formula 13, 14 or 15, or by means of recombinant DNA technology.

Chemical synthesis of the DNA fragment of the present invention may be effected in the same manner as described in the foregoing with respect to the fifth aspect of the present invention. When the DNA fragment of the sixth aspect of the present invention is prepared by means of recombinant DNA technology, such a purpose may be attained by the modification of nucleotide sequence and amplification of DNA molecules in accordance with usual methods such as site-directed mutagenesis (Kramer, W. et al., *Nucleic Acid Res.*, vol. 12, pp. 9441–9456, 1984; *Methods in Enzymology*, vol. 154, pp. 350–367, 1988), polymerase chain reaction (PCR) and the like, making use of an appropriate chromosomal DNA library, cDNA library or the DNA fragment of the fifth aspect of the present invention.

According to a seventh aspect of the present invention, there is provided a vector which contains the DNA fragment of the fifth or the sixth aspect of the present invention.

The obtaining way of the vector of the seventh aspect of the present invention is not particularly restricted, provided that the resulting vector contains the DNA fragment of the fifth aspect of the present invention. Examples of the vector include various plasmid vectors such as pBR322, pUC18, pUC19 and the like, phage vectors such as λgt10, λgt11 and the like and virus vectors such as pMAM-neo, pKCR and the like, into which the DNA fragment of the fifth aspect of the present invention has been introduced. Preferably a vector of the present invention may have a capacity of its replication in host cells to be used.

Preferably, in addition to the DNA fragment of the fifth or the sixth aspect of the present invention, the vector of the present invention may further contain additional nucleotide sequences such as a promoter, a ribosome binding site and the like which are necessary to express the novel polypeptide of the first aspect of the present invention in host cells. Especially, when the vector of the present invention is a expression vector for secretion, a preferred vector may further contain additional nucleotide sequences which encode a signal peptide and the like.

Such nucleotide sequences encoding a promoter, a ribosome binding site, a signal peptide and the like are not particularly limited, provided that they can work their functions in host cells to be used.

For the purpose of obtaining suitable vector for use as the vector of the present invention, the DNA fragment of the fifth or the sixth aspect of the present invention may be inserted into a plasmid vector, a phage vector, a virus vector or the like which already contains necessary nucleotide sequences for the expression and secretion of the novel polypeptide of the first or the second aspect of the present invention, such as those nucleotide sequences which encode a promoter, a ribosome binding site, a signal peptide and the like. As alternative methods, these nucleotide sequences necessary for the expression and secretion may be synthesized chemically and then inserted into an appropriate site of a plasmid vector, a phage vector, a virus vector or the like together with the DNA fragment of the fifth or the sixth aspect of the present invention. Insertion of a DNA fragment into a vector may be effected by usual methods (cf. *Molecular Cloning, A Laboratory Manual*, edited by T. Maniatis et al., Cold Spring Harbor Laboratory, 1982).

According to the eighth aspect of the present invention, there is provided a transformant transformed with the DNA fragment of the fifth or the sixth aspect of the present invention. A transformant which can produce and secrete the novel polypeptide of the first or the second aspect of the present invention is preferable.

The transformant of the eighth aspect of the present invention may be obtained by transforming the DNA fragment of the fifth or the sixth aspect of the present invention into appropriate host cells in accordance with usual methods such as calcium chloride technique, a method in which a calcium phosphate-DNA complex is used, microinjection technique, electroporation or the like.

Preferably, in addition to a nucleotide sequence encoding the novel polypeptide of the first or the second aspect of the present invention, the DNA fragment of the fifth or the sixth aspect of the present invention to be used for the preparation of the transformant may contain additional nucleotide sequences which encode a promoter, a ribosome binding site and the like that are necessary for the expression of the novel polypeptide of the first or the second aspect of the present invention. Especially, when a transformant having the capability of secretion of the polypeptide of the present invention is prepared, the DNA fragment to be used may preferably contain a nucleotide sequence which encodes a signal peptide in addition to other necessary nucleotide sequences for the expression of the polypeptide.

Host cells to be used for the transformation of the DNA fragment of the fifth or the sixth aspect of the present invention are not strictly limited, provided that they are suitable for use in the expression of the novel polypeptide of the first or the second aspect of the present invention. Such a suitable host cells may be selected from either eukaryotic cells such as HeLa cells, COS cells, CHO cells, yeast cells and the like or prokaryotic cells such as *E. coli* cells, *Bacillus subtilis* cells and the like.

The ninth aspect of the present invention provides a transformant transformed with the vector of the seventh aspect of the present invention. The transformant of the ninth aspect of the present invention is obtained by transforming an appropriate host with the vector of the seventh aspect of the present invention by usual methods such as calcium chloride technique, rubidium chloride technique, Hanahan's method (Hanahan, D., Techniques for Transformation of *E. Coli*; in *DNA Cloning*, vol. 1, Glover, D. M. (ed.), pp. 109-136, IRL Press, 1985) or the like. Transformant can be obtained easily by using the vector of the seventh aspect of the present invention because of the high efficiency of transformation.

In addition to a DNA fragment encoding the novel polypeptide of the first or the second aspect of the present invention, which is one of the preferred examples of the vector of the seventh aspect of the present invention, a vector to be used in this instance may further contain a nucleotide sequence which is necessary for the expression of the novel polypeptide of the first and the second aspect of the present invention. Especially, when a transformant having the capability of secretion of the polypeptide of the present invention is prepared, the vector to be used may preferably contain a nucleotide sequence which encodes a signal peptide in addition to other necessary nucleotide sequences for the expression of the polypeptide.

Host cells to be used for the transformation of the vector of the seventh aspect of the present invention are not strictly limited, provided that they are suitable for use in the expression of the novel polypeptide of the first aspect of the present invention. Such a suitable host cells may be selected from either eukaryotic cells such as HeLa cells, COS cells, CHO cells, yeast cells and the like or prokaryotic cells such as *E. coli* cells, *Bacillus subtilis* cells and the like, of which *E. coli* cells are particularly preferred.

As it is well known, that a host cell and a vector are affected each other, taking this into consideration, it is preferable other, to obtain the inventive transformant by selecting an appropriate example of the vector of the seventh aspect of the present invention (or a promoter nucleotide sequence necessary for expression, a signal peptide-encoding nucleotide sequence and the like to be inserted into the vector of the seventh aspect together with a DNA fragment of the present invention) and an appropriate host, in such a combination that the novel polypeptide of the first or the second aspect of the present invention can be expressed efficiently. For example, when cells of a mammal cell line are used as host cells and a virus vector is used as the vector of the seventh aspect of the present invention, said vector may preferably contain a promoter, a ribosome binding site, a nucleotide sequence necessary for expression, a RNA splicing site, a poly A signal addition site and the like, in addition to the DNA fragment of the fifth or the sixth aspect of the present invention.

Illustrative examples of the combination of expression vector with host cells include: an expression vector containing the early promoter gene of simian virus 40 (SV40) with COS-7 cells; an expression vector derived from plasmid pBR322 with tryptophan promoter and tryptophan SD sequence using *E. coli* HB101 cells; and the like combinations.

As preferred examples of the transformant of the eighth aspect of the present invention, the present inventors have prepared *E. coli* JE5505 transformant transformed with the vector of the sixth aspect invention into which a DNA fragment encoding the novel polypeptide of the first or the second aspect invention has been inserted. These transformants have been deposited by the present inventor in Fermentation Research Institute, Agency of Industrial Science and Technology, as follows.

| Deposite number | Date | Transformant | Example |
|---|---|---|---|
| FERM BP-3561 | Sep. 11, '90 | JE5505(pM552) | 1 |
| FERM BP-3608 | Oct. 17, '91 | JE5505(pM560) | 2 |
| FERM BP-3560 | Sep. 11, '90 | JE5505(pM551) | 3 |
| FERM BP-3613 | July 16, '91 | JE5505(PM575B) | 5 |
| FERM BP-3614 | July 16, '91 | JE5505(pM576) | 6 |

The following describes processes suitable for the production of the novel polypeptide of the first or the second aspect of the present invention making use of recombinant DNA techniques.

The tenth aspect of the present invention provides a process for the production of the novel polypeptide of the first or the second aspect of the present invention which comprises the steps of:
  a) preparing a DNA fragment containing a nucleotide sequence which encodes the novel polypeptide of the first or the second aspect of the present invention,
  b) preparing a transformant by transforming host cells with the DNA fragment obtained in the above step a) and
  c) culturing said transformant to allow it to produce the novel polypeptide of the first or the second aspect of the present invention and recovering said novel polypeptide from the culture suspension.

In the process of the tenth aspect of the present invention, the term "a DNA fragment containing a nucleotide sequence which encodes the novel polypeptide of the first or the second aspect of the present invention" means a DNA fragment of the fifth or the sixth aspect of the present invention. Preferably, this DNA fragment may further contain a nucleotide sequence which is necessary for the expression of the novel polypeptide of the first or the second aspect of the present invention, in addition to a nucleotide sequence that encodes said novel polypeptide. If necessary, said DNA fragment may also contain a nucleotide sequence which encodes a signal peptide.

Firstly, appropriate host cells are transformed with a DNA fragment of the fifth or the sixth aspect of the present invention to obtain a transformant. In this instance, a transformant thus obtained belongs to the transformant of the eighth aspect of the present invention, and it can be therefore obtained by the process described in the foregoing.

The obtained transformant is cultured to allow it to produce the polypeptide of interest which is then recovered from the culture suspension. A transformant of the eighth aspect of the present invention, namely a host transformed with a DNA fragment of the fifth or the sixth aspect of the present invention, may be cultured by usual methods for the culturing of microorganisms or mammal cells, in accordance with the procedure disclosed for instance in *Seibutsu Kagaku Kogaku* (or Biochemical Engineering; S. Aiba et al., 1976, Tokyo University Press) or in *Soshiki Baiyo* (or Tissue Culture; J. Nakai et al., 1976, Asakura Shoten).

Next, the produced novel polypeptide of the first or the second aspect of the present invention by using the transformant is recovered from the culture suspension of said transformant. In this instance, the produced novel polypeptide of the first or the second aspect of the present invention may be isolated preferably from cultured cells of the transformant when the product is not secreted extracellularly, or from culture supernatant when secreted in the medium. Purification and recovery of the novel polypeptide of the first or the second aspect of the present invention from a culture suspension containing said polypeptide may be carried out by referring various usual methods for the purification of protein which have been disclosed in many reports and books such as *Seikagaku Jikken Koza* (or Biochemical Experiments; vol. I, Protein Chemistry, 1976, edited by The Japanese Biochemical Society, Tokyo Kagaku Dojin).

Examples of protein purification techniques include salting-out, ultrafiltration, isoelectric precipitation, gel filtration, ion exchange chromatography, various affinity chromatographic techniques such as hydrophobic chromatography, antibody chromatography and the like, chromatofocusing, absorption chromatography and reverse phase chromatography. Consequently, recovery and purification of the novel polypeptide of the first or the second aspect of the present invention may be carried out by selecting suitable ones from these techniques and, if necessary, making use of a HPLC system and the like, in combination between the techniques.

According to a eleventh aspect of the present invention, there is provided a process for the production of the novel polypeptide of the first or the second aspect of the present invention which comprises the steps of:

a) preparing a DNA fragment containing a nucleotide sequence which encodes the novel polypeptide of the first or the second aspect of the present invention, b) constructing a vector containing the DNA fragment obtained in the above step a)

c) preparing a transformant by transforming host cells with said vector and d) culturing said transformant to allow it to produce the novel polypeptide of the first or the second aspect of the present invention and recovering said polypeptide from the culture suspension.

In the process of the eleventh aspect of the present invention, the term "a DNA fragment containing a nucleotide sequence which encodes the novel polypeptide of the first or the second aspect of the present invention" means a DNA fragment of the fifth or the sixth aspect of the present invention.

Firstly, a DNA fragment of the fifth or the sixth aspect of the present invention is inserted into a vector to obtain a new vector containing said DNA fragment, that is, a vector of the seventh aspect of the present invention. Preferably, the constructed vector of the seventh aspect of the present invention may contain another nucleotide sequence which is necessary for the expression of the novel polypeptide of the first or the second aspect of the present invention, in addition to the DNA fragment of the fifth or sixth aspect. If necessary, said vector may also contain a nucleotide sequence which encodes a signal peptide. Process for the construction of such a vector has already been described in the foregoing in relation to the seventh aspect of the present invention.

Next, appropriate host cells are transformed with the constructed vector to obtain a transformant. In this instance, a transformant obtained here belongs to the transformant of the ninth aspect of the present invention, and it can be therefore obtained by the process described in the foregoing.

The obtained transformant is cultured to allow it to produce the polypeptide of interest which is then recovered from the culture suspension. Processes for the subsequent recovery and purification are the same as those described in the foregoing in relation to the tenth aspect of the present invention.

Thus, processes for the production of the novel polypeptide have been described in the tenth and eleventh aspects of the present invention. In performing these processes, the DNA fragment of the fifth or the sixth aspect of the present invention may be used by, as described in the foregoing, adding one or more desired nucleotides to the 5'-end and/or the 3'-end of the sequence which encodes the novel polypeptide of the first aspect of the present invention, without changing the amino acid sequence encoded by said nucleotide sequence.

In this instance, such a nucleotide sequence with nucleotide(s) may also contain a nucleotide sequence which encodes other polypeptide ($\beta$-galactosidase for example) or a part thereof. In such a case, the DNA fragment of the present invention becomes a fused gene with other DNA fragment which encodes different polypeptide, and a transformant transformed with such a fused gene will produce a fused polypeptide of the inventive polypeptide and other polypeptide ($\beta$-galactosidase for example). In this case, it is possible to obtain the novel polypeptide of the first or the second aspect of the present invention by recovering said fused polypeptide and then treating it with appropriate chemical compounds, enzymes and the like to cleave and remove the additional polypeptide portion.

According to a twelfth aspect of the present invention, there is provided a process for the prevention and/or treatment of diseases and syndromes which comprises using the drug composition of the fourth aspect of the present invention. The drug composition to be used in the process of the twelfth aspect of the present invention comprises, as its active ingredient, a polypeptide defined by the amino acid sequence represented by the formula 1, 2, 3, 4, 5, 6 or 8, or a polypeptide which contains at least the amino acid sequence represented by the formula 1, 2, 3, 4, 5, 6 or 8.

As its active ingredient, the drug composition of the present invention may contain the polypeptide which is defined by a derivative of the amino acid sequence represented by the formula 1, 2, 3, 4, 5, 6 or 8 resulting from, as described in the foregoing in relation to the fourth aspect of the present invention, substitution, deletion, addition or the like of at least one amino acid at the N-terminus and/or the C-terminus and/or an inner part of said amino acid sequence.

Also as its active ingredient, the drug composition of the present invention may contain the polypeptide which contains at least a derivative of the amino acid sequence represented by the formula 1, 2, 3, 4, 5, 6 or 8 resulting from substitution, deletion, addition or the like of at least one amino acid at the N-terminus and/or the C-terminus and/or an inner part of said amino acid sequence. Also as its active ingredient, the drug composition of the present invention may contain a chemically modified product of any of the above polypeptide or its derivatives, which is obtained by various methods such as sugar moiety addition, alkylation, oxidation, reduction, hydrolysis and the like, or a therapeutically acceptable acid or base salt thereof.

Though the process of the twelfth aspect of the present invention for the prevention and/or treatment of diseases and syndromes is characterized by the use of the inventive drug composition, said drug composition may contain the aforementioned polypeptide as its single active ingredient or may additionally contain therapeutically acceptable auxiliary components together with said polypeptide. In addition, said process may be either a process in which the drug composition to be used contains a chemically modified product of the aforementioned polypeptide or a salt thereof as its single active ingredient or a process in which the drug composition to be used contains additionally therapeutically acceptable auxiliary components together with a chemically modified product of the aforementioned polypeptide or a salt thereof.

Diseases and syndromes to be prevented and/or treated by the process of the twelfth aspect of the present invention include those in which at least one of the enzymes consisting of trypsin, elastase, plasmin, plasma kallikrein and FXa is taking an important role. In other words, said process of the present invention is used for the purpose of preventing and/or treating at least one disease selected from the group consisting of operative stress, multiple organ failure, shock, pancreatitis, disseminated intravascular coagulation syndrome, ischemic heart disease, nephritis, hepatic cirrhosis, thrombosis after revascularization, edema caused by increased vascular permeability, adult respiratory distress syndrome, rheumatoid arthritis, arthritis and allergy. The process of the twelfth aspect of the prevent invention is not limited to the prevention and/or treatment of specific diseases and syndromes, and therefore is also useful for the prevention and/or treatment of blood coagulation. In addition, said process is also useful for the prevention and/or treatment of other diseases and syndromes in which a substance or a biological molecule having similar structure to at least one of the enzymes consisting of trypsin, elastase, plasmin, plasma kallikrein and FXa is taking an important role.

EXAMPLES

Examples of the present invention are, of course, intended to be illustrative rather than limiting. Abbreviations used herein are based on idiomatical expressions. Experiments were carried out in the light of the following reports and books.

1. *Labo Manual Genetic Engineering*; M. Muramatsu, 1989, Maruzen
2. *Gene Manipulation Techniques*; Y. Takagi, 1980, Kodansha
3. *Gene Manipulation Manual*; Y. Takagi, 1980, Kodansha
4. *Molecular Cloning, A Laboratory Manual*; T. Maniatis et al., 1982, Cold Spring Harbor Laboratory
5. *Methods in Enzymology*; vol. 65, L. Grossman, 1980, Academic Press
6. *Methods in Enzymology*; vol 68, R. Wu, 1979, Academic Press
7. PCR Protocols, *A Guide to Methods and Applications*; Michadel, A. I. et al., 1990, Academic Press
8. *Molecular Cloning, A Laboratory Manual* (second edition); T. Maniatis et al., 1989, Cold Spring Harbor Laboratory

Example 1

Production of the inventive novel polypeptide making use of the inventive novel DNA fragment-Part 1

(1) Construction of plasmid pM469

An expression vector, plasmid pM469, to be used in this example was constructed from plasmid pM463 in the following manner as shown in FIG. 2 and FIG. 3. Plasmid pM463 used herein as the starting material is a derivative of plasmid pBR322, which has been constructed as a plasmid having a function to undergo replication in *E. coli*, containing ampicillin resistance gene and tryptophan promoter gene and containing DNA fragments which encode alkaline phosphatase signal peptide and human pancreatic trypsin inhibitor (to be referred to as "PSTI" hereinafter) (Kanamori, T. et al., Gene, vol.66, pp.295-300, 1988).

Firstly, plasmid pM463 was double-digested with restriction endonucleases HindIII and NruI, the resulting DNA fragments were applied to 0.7% agarose gel electrophoresis and then a DNA fragment of about 3.4 kb in the gel was absorbed to diethylaminoethyl cellulose paper (to be referred to as "DEAE cellulose paper" hereinafter) to separate it from other fragments. Thereafter, the DEAE cellulose paper was washed with a high concentration salt solution (2M NaCl/10 mM Tris-HCl buffer (pH 7.5)/1 mM EDTA) to recover the DNA fragment of about 3.4 kb.

Separately from this, an oligonucleotide fragment was designed which consisted of SD sequence, a nucleotide sequence encoding *E. coli* alkaline phosphatase signal peptide and a nucleotide sequence encoding a part of N-terminal amino acid sequence of PSTI. The thus designed fragment was divided into 6 small fragments (SEQ ID NOS: 63 to 68) and each of them was synthesized using a chemical synthesizer (381A, Applied Biosystems, Inc.), with the results shown in FIG. 1. Of these 6 fragments thus synthesized, S34, S35, S18 and S19 (SEQ ID NOS: 64 to 67, respectively) were subjected to 5'-end phosphorylation with T4 polynucleotide kinase in the presence of ATP. Subsequently, each combination of oligonucleotides S33 with S34, S35 with S18 and S19 with S20 were subjected to annealing, followed by their ligation making use of a T4 DNA ligase (Takara Shuzo Co., Ltd.). The thus ligated sample was then applied to 8% polyacrylamide gel electrophoresis to obtain a DNA fragment (linker 1) of about 100 bp.

Next, the aforementioned DNA fragment of about 3.4 kb and the thus obtained DNA fragment of about 100 bp were ligated, and E. coli HB101 was transformed with the thus ligated product to isolate an ampicillin-resistant colony of interest. Plasmid DNA was constructed from the thus obtained transformant and named pM468 (cf. FIG. 2).

The plasmid pM468 was double-digested with EcoRI and DraI, and a DNA fragment of about 2.4 kb was prepared using DEAE cellulose paper in the same manner as described above. Separately from this, plasmid pKC7 containing kanamycin resistance gene (km$^r$) (Ngarajarao, R. et al., Gene, vol. 7, pp. 79–82, 1979) was double-digested with restriction endonucleases EcoRI and SmaI to prepare a DNA fragment of about 1.4 kb containing kanamycin resistance gene.

Next, the aforementioned DNA fragment of about 2.4 kb and the thus obtained DNA fragment of about 1.4 kb were ligated, and E. coli HB101 was transformed with the thus ligated product to isolate a kanamycin-resistant colony of interest. Plasmid DNA was prepared from the thus obtained transformant, named pM469 and used in the following experiments as an expression vector (cf. FIG. 3).

(2) Cloning of novel DNA fragment of the invention

A DNA fragment encoding a polypeptide of the present invention (to be referred to as "TN70" hereinafter as a matter of convenience) which is defined by the aforementioned amino acid sequence of formula 3 was prepared by PCR using a commercial human cDNA library.

Firstly, 5 μl phage solution of a λgt11 cDNA library (Clontech Laboratories, Inc.) which has been prepared from healthy human liver mRNA was diluted with 200 μl of distilled water and treated at 90° C. for 10 minutes to use as a template of PCR.

Next, a sense primer, p-s01 (SEQ ID NO: 69) (FIG. 4A), was synthesized chemically using the aforementioned chemical synthesizer. This p-s01 is a oligonucleotide fragment in which a restriction endonuclease EaeI recognition sequence has been introduced into its 5'-end side, in addition to a nucleotide sequence deduced from the N-terminal amino acid sequence (SEQ ID NO: 70), Thr-Val-Ala-Ala-Cys-Asn-Leu-Pro, of the inventive polypeptide TN70. In this instance, nucleotide sequences corresponding to Thr and Ala were selected based on the highest human amino acid codon usage frequency (Wada, K. et al., Nucleic Acid Res., vol. 18, pp. 2367–2411, 1990). In the case of Val, a nucleotide sequence of the second highest codon usage was used in order to avoid formation of an EaeI cutting site, and Leu with the first and second highest usage.

As an antisense primer, p-a01 (SEQ ID NO: 71) (FIG. 4B) was synthesized chemically. The p-a01 is a oligonucleotide fragment in which a restriction endonuclease BamHI recognition sequence has been introduced into its 5'-end side, in addition to a nucleotide sequence complementary to a nucleotide sequence which encodes the C-terminal amino acid sequence (SEQ ID NO: 72), Arg-Phe-Ser-Asn, of the inventive polypeptide, with a stop codon so that the C-terminus becomes Asn.

After purifying the thus obtained p-s01 and p-a01 using OPC column (Applied Biosystems, Inc.), PCR was carried out in the following manner. Firstly, p-s01 and p-a01 were added to 100 μl of a solution containing the aforementioned template DNA for PCR use, and 30 cycles of PCR was carried out using a Gene Amp ™ DNA amplification reagent kit with AmpliTaq ™ (Takara Shuzo Co., Ltd.). In this instance, each PCR cycle was carried out at 94° C. for 1 minute, at 55° C. for 2 minutes and at 72° C. for 3 minutes in that order. When the thus amplified product by means of PCR was applied to 1.5% agarose gel electrophoresis, a single band corresponding to the objective size of 220 bp was observed.

(3) Construction of expression vector

Figure 6:
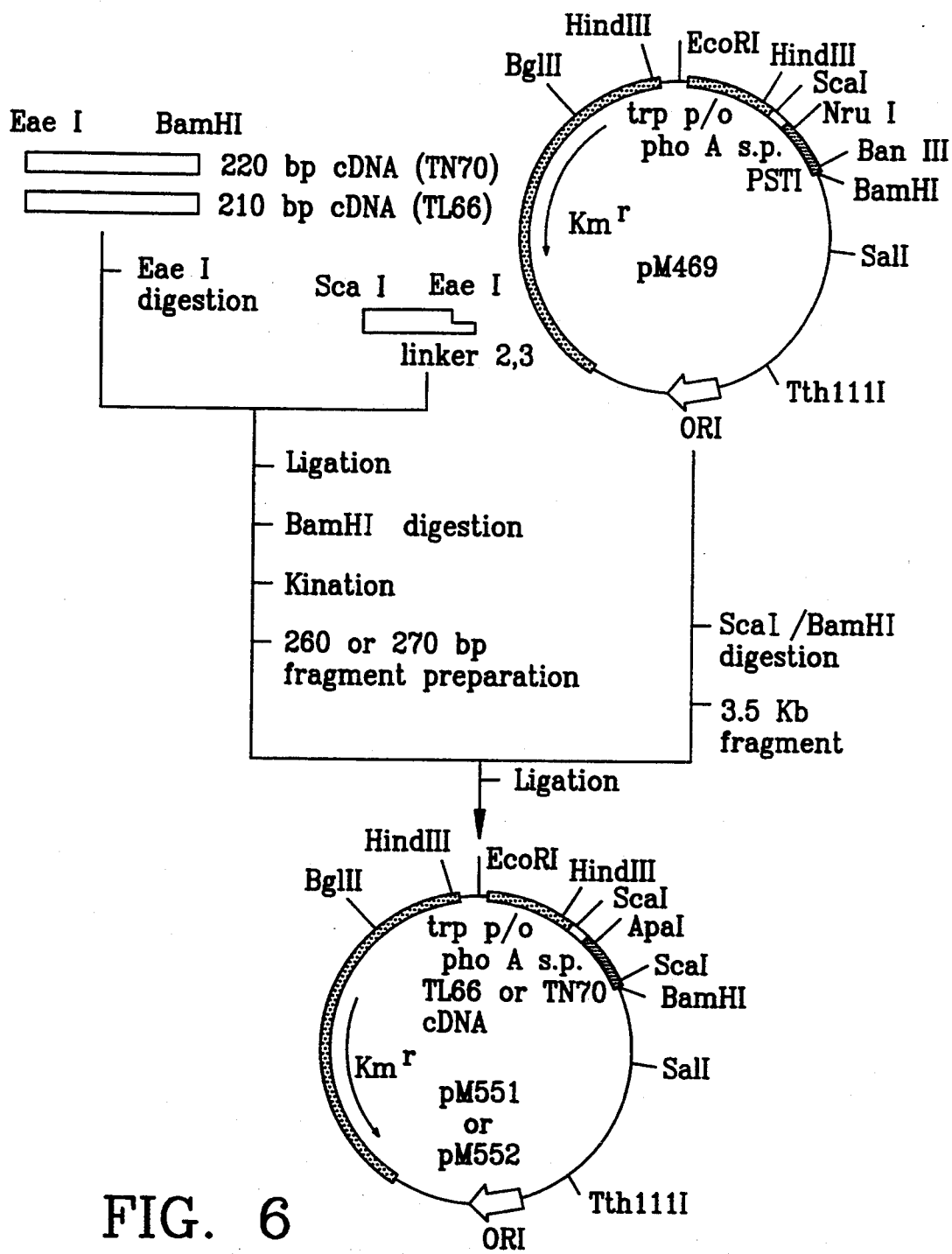
FIG. 6 shows a process for the construction of plasmids pM551 and pM552.

Using the amplified product thus obtained in the above step (2), an expression vector containing a DNA fragment of the present invention which encodes the inventive polypeptide TN70 was constructed in the following protocol as shown in FIG. 6 and FIG. 7.

Firstly, linkers 2 and 3 (SEQ ID NOS: 73 and 74) containing a portion (C-terminal side) of E. coli alkaline phosphatase signal peptide were chemically synthesized using the aforementioned chemical synthesizer (FIG. 5). Thereafter, the 5'-end of linker 3 was phosphorylated with T4 polynucleotide kinase (Takara Shuzo Co., Ltd.) in the presence of ATP, and the thus phosphorylated linker 3 was annealed with linker 2 to obtain a ligation linker (FIG. 5).

Separately from this, the amplified product obtained in the above step (2) was digested with EaeI and purified by means of phenol treatment and ethanol precipitation. The thus purified product was ligated with the just described ligation linker using T4 DNA ligase (Takara Shuzo Co., Ltd.). The ligated product was then digested with BamHI, and the 5'-end of the resulting DNA fragment of about 270 bp was phosphorylated using T4 polynucleotide kinase and ATP. The thus phosphorylated fragment was applied to 1.5% low melting agarose gel electrophoresis, and a portion of the gel containing the aimed DNA fragment of about 270 bp was cut out. The thus sliced portion of agarose gel was melted at 65° C., and the DNA fragment of interest was extracted and purified by phenol treatment and ethanol precipitation to use it as passenger DNA.

Next, plasmid pM469 was double-digested with ScaI and BamHI and the resulting DNA fragments were subjected to 0.7% low melting agarose gel electrophoresis, followed by separation, extraction and purification of a DNA fragment of about 3.5 kb. The thus purified DNA fragment was ligated with the aforementioned passenger DNA of about 270 bp using the aforementioned T4 DNA ligase to obtain expression plasmid pM552 (cf. FIG. 6).

The thus obtained plasmid pM552 was double-digested with HindIII and BamHI, and a DNA fragment of about 310 bp was extracted and purified. The purified DNA fragment was ligated with each of phage vectors M13mp18 and M13mp19 (both from Takara Shuzo Co., Ltd.) which have been double-digested with HindIII and BamHI in advance. Thereafter, E. coli JM109 was transfected with the resulting ligation mixture to obtain M13 phage culture from which single stranded DNA (SSDNA) was extracted and purified and subjected to sequencing using a DNA sequencer (DNA Sequencer 370A, Applied Biosystems, Inc.).

Thus confirmed nucleotide sequence of a region of plasmid pM552 from its HindIII recognition site to BamHI recognition site containing the DNA fragment of the present invention and its corresponding amino acid sequence are shown in FIG. 7 (cf. Sequence Nos 75 and 76 in the Sequence Listing).

(4) Preparation and cultivation of transformant

A transformant, *E. coli* JE5505 (pM552), was prepared by transforming *E. coli* JE5505 with the expression plasmid pM552 obtained above, in accordance with Hanahan's method (Hanahan, D., Techniques for Transformation of *E. coli*; in *DNA Cloning*, vol. 1, Glover, D. M. (ed.), pp. 109–136, IRL Press, 1985).

Each transformant isolated by the above method was cultured overnight in 5 ml of L-broth containing 50 μg/ml of kanamycin. The resulting culture broth was inoculated in 50 volumes of M9CA medium containing 50 μg/ml of kanamycin and cultured at 37° C. for about 1 hour. After adding 3-β-indole acrylic acid (Wako Pure Chemical Industries, Ltd.) to a final concentration of 10 μg/ml, the culturing was continued for additional 16 hours for expression of gene encoding the aimed peptides. Thereafter, culture supernatant was obtained from the resulting culture broth using a centrifuge (CR20B3, Hitachi Koki Co., Ltd.).

Each culture supernatant thus prepared was diluted with 0.1% BSA/0.2M triethanolamine-HCl buffer (pH 7.8) to each predetermined concentration, and the diluted samples were used for the measurement of trypsin-inhibiting activity in accordance with the procedure described in Example 4-(1). In this instance, culture supernatant of a transformant, *E. coli* JE5505 (pM553), was used as a control which has been obtained by transforming *E. coli* JE5505 with a plasmid pM553 prepared by eliminating the aforementioned 270 bp passenger DNA from the plasmid pM552.

Compared to the control, markedly high trypsin-inhibiting activity was found in the culture supernatant of *E. coli* JE5505 (pM552). The transformant *E. coli* JE5505 (pM552) has been deposited by the present inventors on Sep. 11, 1990, in Fermentation Research Institute, Agency of Industrial Science and Technology, and has been assigned the designation as FERM BP-3561.

(5) Purification of inventive novel polypeptide from culture supernatant of *E. coli* JE5505 (pM552)

(a) Ammonium sulfate fractionation

Ammonium sulfate was added to 5 liters of culture supernatant of *E. coli* JE5505 (pM552) to a level of 80% saturation. During ammonium sulfate fractionation, pH of the solution was checked and adjusted to 5.5 to 6.0 with 0.4M $Na_2HPO_4$. The mixture was stirred until ammonium sulfate was completely dissolved and then the solution was allowed to stand overnight at 4° C.

The sample was filtrated through a 5-μm filter (Mili-Pak 80, Millipore Inc.) and the resulting precipitation was washed with 80% saturated ammonium sulfate solution, and the residual material on the filter was recovered by distilled water. The solution thus obtained was concentrated to 3 ml using an ultrafiltration membrane (molecular weight cutoff of 1,000; Diaflow membrane YM-1, Grace Company).

(b) Gel filtration chromatography

The concentrated sample obtained in the above step (a) was applied to Superdex 75 column (HiLoad TM 16/60 Superdex TM 75, Pharmacia Biosystems Group) which has been equilibrated with PBS⁻ and then eluted by the same buffer at a flow rate of 1 ml/min and fractionated by 3 ml.

A portion of each fraction was checked for its trypsin-inhibiting activity in accordance with the procedure discribed in Example 4-(1). Thereafter, active fractions were pooled and dialyzed overnight at 4° C. against 20 mM Tris-HCl buffer (pH 8.5) using a dialysis membrane (molecular weight cutoff of 1,000; Spectrum Medical Industries, Inc.).

(c) Anion exchange chromatography

The dialyzed sample obtained in the above step (b) was applied to Mono Q column (5 mmφ×50 mm, Pharmacia Biosystems Group) which has been equilibrated with 20 mM Tris-HCl (pH 8.5). Using an FPLC system (Pharmacia Biosystems Group), elution was carried out at a flow rate of 1 ml/min with a linear density gradient of 0 to 0.4M NaCl/20 mM Tris-HCl (pH 8.5)/40 min. Protein concentration in the eluent was monitored at 280 nm and each protein peak was fractionated. A portion of each fraction was checked for its trypsin-inhibiting activity and active fractions were pooled. The pooled sample was used in the following reverse phase chromatography.

(d) Reverse phase chromatography

The active fraction obtained in the above step (c) was applied to Vydac C18 column (4.6 mmφ×25.0 cm, Separations Group) which has been equilibrated with 0.04% trifluoroacetic acid solution. Using Waters 625 LC system (Waters of division of Millipore Inc.), elution was carried out at a flow rate of 1.0 ml/min with a linear density gradient of 0 to 70% acetonitrile/0.04% trifluoroacetic aid/30 min. Protein concentration in the eluent was monitored at 280 nm and each protein peak was fractionated. A portion of each fraction was checked for its trypsin-inhibiting activity and an active fraction was dried under a reduced pressure using a centrifugation concentrator (Speed Vac Concentrator, Savant Instruments Inc.). The obtained purified sample was subjected to the following SDS-polyacrylamide gel electrophoresis (6), amino acid sequence analysis (7) and activity measurements in Examples 4 and 7.

(6) SDS-polyacrylamide gel electrophoresis

The purified sample obtained above was subjected to SDS-polyacrylamide gel electrophoresis (to be referred to as "SDS-PAGE" hereinafter) in the following Laemmli's method (Laemmli, U.K., Nature, vol. 227, pp. 680–685, 1970).

The sample was dissolved in distilled water and then the same volume of Seprasol II (Daiichi Pure Chemicals Co., Ltd.) was added. The resulting mixture was treated at 100° C. for 5 minutes. The sample was applied to a 15% gel (5 cm×9 cm, 1 mm in thickness) and electrophoresed at 15 mA for 50 minutes and then at 30 mA for 35 minutes. In this instance, a commercial molecular weight marker kit was used (Electrophoresis calibration kit for polypeptide, Pharmacia Biosystems Group).

After the electrophoresis, staining was carried out with a commercial silver staining kit (2D-Silver Staining Reagent Kit, Daiichi Pure Chemicals Co., Ltd.). The purified sample showed a single band by SDS-PAGE.

(7) Determination of amino acid sequence

Amino acid sequence of the purified sample obtained in the above procedure (5) was determined in the following manner.

The purified sample was dissolved in 50% acetic acid solution and its amino acid sequence was determined using Model 477A Protein Sequencing System 120A PTH Analyzer (Applied Biosystems Inc.). Identification of the amino acid sequence was determined by detecting PTH-amino acid at an absorbance of 270 nm, based on the retention time of standard PTH-amino acids (Applied Biosystems Inc.) which have been isolated in the same procedure.

As the results, it was confirmed that the purified sample of the foregoing procedure (5) is the TN70 of interest (cf. Sequence No. 76 in the Sequence Listing).

Example 2

Production of the inventive novel polypeptide making use of the inventive novel DNA fragment—Part 2

(1) Construction of plasmid pM563

An expression vector, plasmid pM563, to be used in the following step (2) as a template for PCR was prepared from the plasmid pM552 obtained in Example 1-(3). Plasmid pM563 contains a DNA fragment which encodes a moiety of the amino acid sequence represented by the foregoing formula 3, from its N-terminal amino acid to 55th amino acid.

Firstly, plasmid pM552 was double-digested with restriction endonucleases HindIII and BamHI and the resulting DNA fragments were applied to 1% low melting agarose gel electrophoresis. A portion of the gel containing the aimed DNA fragment of about 310 bp was cut out. The thus sliced portion of agarose gel was melted at 65° C., and the DNA fragment of interest was extracted and purified by phenol treatment and ethanol precipitation. The aforementioned phage vector M13mp18 was double-digested with HindIII and BamHI and then ligated with the just obtained DNA fragment of about 310 bp using the aforementioned T4 DNA ligase. Thereafter, E. coli JM109 was transfected with the resulting ligation mixture to obtain M13 phage culture from which ssDNA was extracted and purified.

Next, PCR was carried out using the thus obtained ssDNA as a template in the following manner. Firstly, ScaI sense primer (SEQ ID NO: 77) (FIG. 8A) was synthesized using the aforementioned chemical synthesizer, purified using the aforementioned OPC column and then subjected to phosphorylation using T4 polynucleotide kinase and ATP to phosphorylate its 5'-end. As an antisense primer, p-a02 (SEQ ID NO: 78) (FIG. 8B) was synthesized using the aforementioned chemical synthesizer and purified using the aforementioned OPC column. The thus synthesized ScaI sense primer and p-a02 were added to 100 μl of a solution for PCR containing the aforementioned ssDNA, and 30 cycles of PCR was carried out using an amplification reagent kit for PCR use (AmpliTaq ™, Takara Shuzo Co., Ltd.). In this instance, each PCR cycle was carried out at 94° C. for 1 minute, at 55° C. for 2 minutes and at 72° C. for 3 minutes in that order. The thus amplified product was digested with BamHI and then purified by means of phenol treatment and ethanol precipitation. Separately from this, plasmid pM469 was double-digested with ScaI and BamHI in the same protocol as in Example 1-(3) to obtain a DNA fragment of about 3.5 kb. By ligating this DNA fragment with the above amplified product, plasmid pM563 was obtained.

(2) Cloning of novel DNA fragment of the invention

A DNA fragment encoding a polypeptide of the present invention (to be referred to as "CC51" hereinafter as a matter of convenience) which is defined by the aforementioned amino acid sequence of formula 1 (SEQ ID NO: 1) was cloned using plasmid pM563 obtained in the above step (1) as a template for PCR use in the light of the method of Landt et al. (Landt, O. et al., Gene, vol. 96, pp. 125–128, 1990).

Firstly, as a sense primer for use in primary PCR, HindIII sense primer (SEQ ID NO: 79) (FIG. 9A) was synthesized using the aforementioned chemical synthesizer and purified using the aforementioned OPC column. As an antisense primer, p-a03 (SEQ ID NO: 80) (FIG. 9A) was synthesized and purified in the same manner. PCR was carried out using the thus synthesized HindIII sense primer (SEQ ID NO: 79) and p-a03 (SEQ ID NO: 80) in the same manner as in the above step (1). When the thus amplified product by means of PCR was applied to 1.5% agarose gel electrophoresis, a single band corresponding to the objective size of 110 bp was observed. The thus amplified product was purified by means of phenol treatment and ethanol precipitation and then dissolved in TE buffer.

Next, secondary PCR was carried out in the same manner as the primary PCR, using the amplified product as a sense primer and plasmid pM563 as a template. In this instance, BamHI antisense primer (SEQ ID NO: 79) (FIG. 9C) was synthesized and purified to be used as an antisense primer. When a portion of the amplified product by the secondary PCR was applied to 1.5% agarose gel electrophoresis, a single band corresponding to the objective size of 290 bp was observed.

(3) Construction of expression vector

Figure 10:
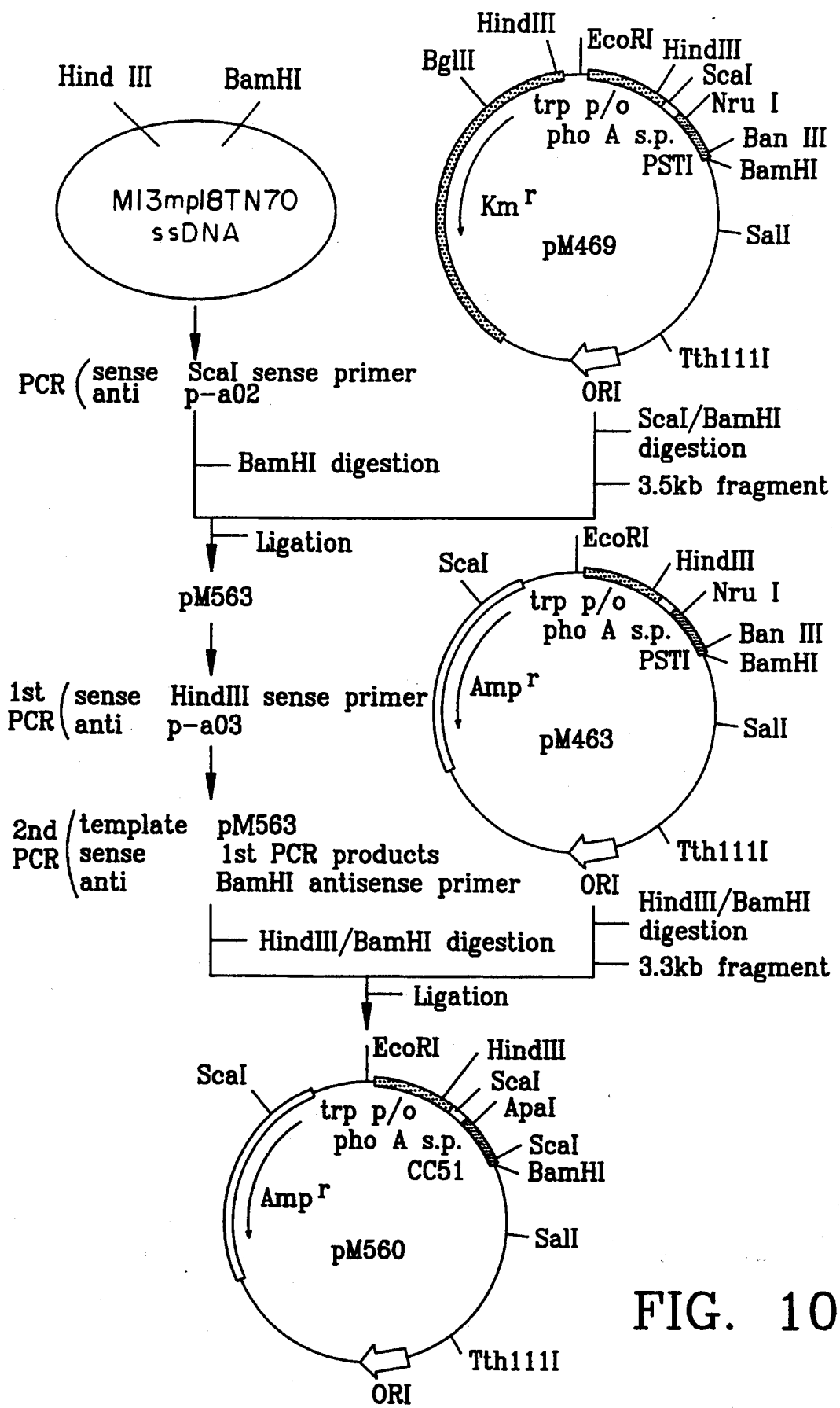
FIG. 10 shows a process for the construction of plasmid pM560.

Using the amplified product thus obtained by the secondary PCR in the above step (2), an expression vector containing a DNA fragment of the present invention which encodes the inventive polypeptide CC51 was constructed in the following protocol as shown in FIG. 10.

Firstly, plasmid pM463 (Kanamori, T. et al., Gene, vol. 66, pp. 295–300, 1988) used in Example 1-(1) was double-digested with HindIII and BamHI and the resulting DNA fragments were subjected to 0.7% low melting agarose gel electrophoresis to obtain a DNA fragment of about 3.3 kb.

Next, the amplified product of about 290 bp obtained in the above step (2) was purified by means of phenol treatment and ethanol precipitation and then double-digested with HindIII and BamHI. The thus obtained DNA fragment was ligated with the just described DNA fragment of about 3.3 kb using the aforementioned T4 DNA ligase to construct an expression plasmid pM560 (cf. FIG. 10).

After double-digesting plasmid pM560 with HindIII and BamHI, a DNA fragment of about 250 bp was extracted and purified and then ligated with each of the aforementioned phage vectors M13mp18 and M13mp19 which have been double-digested with HindIII and BamHI in advance. Thereafter, E. coli JM109 was transfected with the resulting ligation mixture to obtain M13 phage culture from which ssDNA was extracted and purified and subjected to sequencing using the aforementioned DNA sequencer.

Thus confirmed nucleotide sequence of a region of plasmid pM560 from its HindIII recognition site to BamHI recognition site containing the polypeptide of the present invention and its corresponding amino acid sequence are shown in FIG. 11 (cf. Sequence Nos: 82 and 83 in the Sequence Listing).

(4) Preparation and cultivation of transformant

A transformant, E. coli JE5505 (pM560), was prepared by transforming E. coli JE5505 with the plasmid pM560 obtained in the above step (3) in accordance with the Hanahan's method. The thus obtained transformant, *E. coli* JE5505 (pM560), was cultured in the same protocol as in Example 1-(4) expect that 50 μg/ml of Kanamycin was replaced by 50 μg/ml of Ampicillin to obtain a culture supernatant.

The culture supernatant thus prepared was diluted with 0.1% BSA/0.2M triethanolamine-HCl buffer (pH 7.8) to each predetermined concentration, and the diluted samples were used for the measurement of trypsin-inhibiting activity in accordance with the procedure described in Example 4-(1). In this instance, culture supernatant of a transformant, *E. coli* JE5505 (pM463C), was used as a control which has been obtained by transforming *E. coli* JE5505 with a plasmid pM463C prepared by eliminating the inventive polypeptide-encoding DNA fragment from the plasmid pM560.

Compared to the control, markedly high trypsin-inhibiting activity was found in the culture supernatant of *E. coli* JE5505 (pM560). The transformant *E. coli* JE5505 (pM560) has been deposited by the present inventors on Oct. 17, 1991, in Fermentation Research Institute, Agency of Industrial Science and Technology, and has been assigned the designation as FERM BP-3608.

(5) Purification of inventive novel polypeptide from culture supernatant of *E. coli* JE5505 (pM560)

The polypeptide of the present invention was recovered and purified from a culture supernatant of *E. coli* JE5505 (pM560) obtained in the above step (4) in the following manner.

(a) Acid treatment

The culture supernatant obtained in the above step (4) was adjusted to pH 4 with 6N HCl and then allowed to stand for 2 hours. The sample was filtrated through a 0.5-μm filter membrane (Ultipor GF Plus, Millipore Inc.) and the filtrate was applied to SP-Zetaprep cartridge 100 (Quno) at a rate of 10 ml/min. After washing with MacIlvane buffer (pH 4.0), elution was carried out at a flow rate of 14 ml/min with a pH gradient of 4.0 to 9.0 using 200 ml of the MacIlvane buffer (pH 4.0 ) and 200 ml of 50 mM $Na_2HPO_4$ (pH 9.0). Protein concentration in the eluent was monitored at 280 nm, and the eluent was fractionated by 14 ml. A portion of each fraction was checked for its trypsin-inhibiting activity and active fractions were pooled and concentrated using an ultrafiltration membrane (molecular weight cutoff of 1,000; Diaflow membrane YM-1, Grace Company). The concentrated sample was subjected to the following gel filtration chromatography.

(b) Gel filtration chromatography

The concentrated sample was applied to Superdex 75 column (HiLoad TM 16/60 Superdex TM 75, Pharmacia Biosystems Group) which has been equilibrated with 0.2M ammonium acetate solution. Using an FPLC system (Pharmacia Biosystems Group) elution was carried out by 0.2M ammonium acetate solution at a flow rate of 1 ml/min and fractionated by 3 ml. A portion of each fraction was checked for its trypsin-inhibiting activity and active fractions were pooled. Thereafter, the pooled sample was frozen in liquid nitrogen and then lyophilized using a freeze dryer (Bio Freeze BF-2, B.M. Equipments Co., Ltd.).

(c) Cation exchange chromatography

The lyophilized sample obtained in the above step (b) was dissolved in an appropriate volume of 20 mM acetate buffer (pH 4.0) and applied to Mono S HR5/5 column (Pharmacia Biosystems Group) which has been equilibrated with 20 mM sodium acetate buffer (pH 4.0). Using an FPLC system (Pharmacia Biosystems Group), elution was carried out at a flow rate of 1 ml/min with a linear density gradient of 0 to 1M NaCl/20 mM sodium acetate buffer (pH 4.0)/60 min. Protein concentration in the eluent was monitored at 280 nm and each protein peak was fractionated. A portion of each fraction was checked for its trypsin-inhibiting activity and active fractions were used in the following reverse phase chromatography.

(d) Reverse phase chromatography

The active fraction obtained in the above step (c) was applied to Vydac C18 column (4.6 mmφ×25.0 cm, Separations Group) which has been equilibrated with 0.04% trifluoroacetic acid solution. Using Waters 625 LC system (Waters of division of Millipore Inc.), elution was carried out at a flow rate of 1.0 ml/min with a linear density gradient of 0 to 100% acetonitrile/0.04% trifluoroacetic acid/30 min. Protein concentration in the eluent was monitored at 280 nm and each protein peak was fractionated. A portion of each fraction was checked for its trypsin-inhibiting activity. The active fraction was dried under a reduced pressure using a centrifugation concentrator (Speed Vac Concentrator, Savant Instruments Inc.). The obtained purified sample was subjected to the following SDS-PAGE (6), amino acid sequence analysis (7) and activity measurement in Example 4.

(6) SDS-PAGE

The purified sample obtained in the above procedure (5) was subjected to SDS-PAGE in the same manner as described in Example 1-(6).

After the electrophoresis, staining was carried out with the commercial silver staining kit. The purified sample showed a single band by SDS-PAGE.

(7) Determination of amino acid sequence

The purified sample obtained in the above procedure (5) was dissolved in 50% acetic acid solution and its amino acid sequence was determined according to the procedure of Example 1-(7).

As the results, it was confirmed that the purified sample of the foregoing procedure (5) is the inventive polypeptide CC51 of interest (cf. Sequence No: 82 of the Sequence Listing).

Example 3

Production of polypeptide making use of the inventive novel DNA fragment (1) Cloning of novel DNA fragment of the invention A DNA fragment encoding a polypeptide (to be referred to as "TL66" hereinafter as a matter of convenience) which is defined by the aforementioned amino acid sequence of formula 8 was prepared in the same protocol as described in Example 1-(2).

A λgt11 cDNA library prepared from healthy human liver mRNA was used as a template for use in PCR which was carried out 30 cycles using a Gene Amp TM DNA amplification reagent kit with AmpliTaq TM (Takara Shuzo Co., Ltd.). Each PCR cycle was carried out at 94° C. for 1 minute, at 55° C. for 2 minutes and at 72° C. for 3 minutes in that order. In this instance, p-s01 (SEQ ID NO: 69) (FIG. 4A) prepared in Example 1-(2) was used as a sense primer and p-a04 (SEQ ID NO: 84) (FIG. 12) was used as an antisense primer by synthesizing it using the aforementioned chemical synthesizer and purifying the product using the aforementioned OPC column.

When a portion of the amplified product by means of PCR was applied to 1.5% agarose gel electrophoresis, a single band corresponding to the objective size of 210 bp was observed.

(2) Construction of expression vector

Using the amplified product thus obtained in the above procedure (1), an expression vector containing a DNA fragment of the present invention which encodes the polypeptide TL66 was constructed according to the procedure of Example 1-(3).

Firstly, the amplified product of about 210 bp obtained in the above procedure (1) was digested with EaeI and purified by means of phenol treatment and ethanol precipitation. The thus purified product was ligated with the attachment linker prepared in Example 1-(3) using T4 DNA ligase (Takara Shuzo Co., Ltd.). The ligation mixture was then digested with BamHI, and the 5'-end of the resulting DNA fragment of about 260 bp was phosphorylated using T4 polynucleotide kinase and ATP. The thus phosphorylated fragment was applied to 1.5% low melting agarose gel electrophoresis, and an aimed DNA fragment of about 260 bp was extracted from the gel and purified to use it as passenger DNA. By incorporating the thus prepared passenger DNA into plasmid pM469 according to the process of Example 1-(3), an expression plasmid pM551 was obtained (cf. FIG. 6).

Plasmid pM551 was double-digested with HindIII and BamHi, and a DNA fragment of about 300 bp was extracted and purified. The purified DNA fragment was ligated with each of phage vectors M13mp18 and M13mp19 (both from Takara Shuzo Co., Ltd.) which have been double-digested with HindIII and BamHI in advance. Thereafter, E. coli JM109 was transfected with the resulting ligation mixture to obtain M13 phage culture from which ssDNA was extracted and purified and subjected to sequencing using the aforementioned DNA sequencer.

Thus confirmed nucleotide sequence of a region of plasmid pM551 from its HindIII recognition site to BamHI recognition site containing the DNA fragment of the present invention and its encoded amino acid sequence are shown in FIG. 13 (cf. Sequence Nos: 85 and 86 in the Table of Sequence).

(3) Preparation and cultivation of transformant

A transformant, E. coli JE5505 (pM551), was prepared by transforming E. coli JE5505 with the plasmid pM551 obtained in the above procedure (2), in accordance with the Hanahan's method. The transformant thus obtained was cultured in the same manner as described in Example 1-(4) to recover its cultured supernatant by centrifugation.

The culture supernatant thus prepared was diluted with 0.1% BSA/0.2M triethanolamine-HCl buffer (pH 7.8) to each predetermined concentration, and the diluted samples were used for the measurement of trypsin-inhibiting activity in accordance with the procedure described in Example 4-(1). In this instance, culture filtrate of a transformant, E. coli JE5505 (pM553), was used as a control in the same protocol as described in Example 1-(4).

Compared to the control, markedly high trypsin-inhibiting activity was found in the culture supernatant of E. coli JE5505 (pM551). The transformant E. coli JE5505 (pM551) has been deposited by the present inventors on Sep. 11, 1990, in Fermentation Research Institute, Agency of Industrial Science and Technology, and has been assigned the designation as FERM BP-3560.

(4) Purification of polypeptide from culture supernatant of E. coli JE5505 (pM551)

A purified sample of the polypeptide was prepared from a culture supernatant of E. coli JE5505 (pM551) obtained in the above step (3) by ammonium sulfate fractionation, gel filtration chromatography, anion exchange chromatography and reverse phase chromatography in the same manner as in Example 1-(5).

The obtained purified sample was subjected to the following SDS-PAGE (5), amino acid sequence analysis (6) and activity measurements in Examples 4 and 7.

(5) SDS-PAGE

The purified sample obtained in the above procedure (4) was subjected to SDS-polyacrylamide gel electrophoresis in the same manner as described in Example 1-(6).

After the electrophoresis, staining was carried out with the commercial silver staining kit.

The purified sample showed a single band by SDS-PAGE.

(6) Determination of amino acid sequence

The purified sample obtained in the above procedure (4) was dissolved in 50% acetic acid solution and its amino acid sequence was determined according to the procedure of Example 1-(7).

As the results, it was confirmed that the purified sample of the foregoing procedure (4) is the polypeptide TL66 of interest (cf. Sequence No. 86 of the Sequence Listing).

Example 4

Measurement of enzyme-inhibiting activities-1

Enzyme-inhibiting activities of purified samples of polypeptides TN70, CC51 and TL66 obtained in Example 1-(5), Example 2-(5) and Example 3-(4), respectively, were measured in the following way. In this instance, UTI purified from human urine (Mochida Pharmaceutical Co., Ltd.; Ohnish H. et al., Folia Pharmacol. Japon., 85, pp. 1–6, 1985) was used as a positive control in each assay system.

In each assay system, concentration of test samples was expressed as U/ml of bovine trypsin-inhibiting concentration based on UTI.

(1) Human trypsin-inhibiting activity

The purified sample obtained in Example 1-(5) was dissolved in 100 μl of distilled water. Concentration of this solution was determined based on its bovine trypsin-inhibiting activity using the aforementioned UTI as a standard. The solution was then diluted to various concentration levels with 0.1% BSA/0.2M triethanolamine-HCl buffer (pH 7.8) for the activity measurement. The aforementioned UTI was also diluted in the same manner.

Using the aforementioned synthetic compound S-2444 as a substrate, human trypsin-inhibiting activities of the diluted test samples and the positive control were measured in accordance with the method of Kassell (Kassell B., Methods in Enzymol., vol 19, pp. 84–852, 1970) as follows.

Human trypsin (Calbiochem) was dissolved in 0.001M HCl to a concentration of 1,000 SU/ml and the solution was further diluted with 0.1% BSA/0.2M triethanolamine-HCl buffer (pH 7.8) to prepare 1.25 SU/ml of trypsin solution. 2 mM solution of S-2444 was prepared by dissolving it in distilled water.

Next, 100 μl of the test sample or positive control was mixed with 100 μl of the trypsin solution. After incubation at 37° C. for 10 minutes, 50 μl of the S-2444 solution was added to the mixture to start the reaction. The reaction was carried out at 37° C. for 20 minutes and then stopped by adding 50 μl of 50% acetic acid solution to the reaction mixture. Thereafter, absorbance at 405 nm was measured using a spectrophotometer.

In this instance, in order to eliminate absorbance of various solutions in the reaction mixture, a blank solution was prepared by mixing 100 μl of the trypsin solution with 50 μl of 50% acetic acid and then with 100 μl of each test sample or the positive control and with 50 μl of the S-2444 solution.

As shown in FIG. 14A, human trypsin-inhibiting activity was found in the polypeptide TN70 of the present invention obtained in Example 1-(5) similar to the case of the positive control.

In this figure, human trypsin remaining activity was expressed by percentage based on the absorbance of a control reaction mixture in which 100 μl of 0.1% BSA/0.2M triethanolamine-HCl buffer (pH 7.8) was used instead of the test sample or the positive control.

In the same manner, the purified sample of CC51 obtained in Example 2-(5) was checked for its human trypsin-inhibiting activity. As shown in FIG. 14B, human trypsin-inhibiting activity was found in the polypeptide CC51 of the present invention obtained in Example 2-(5) similar to the case of the positive control.

Figure 14C:
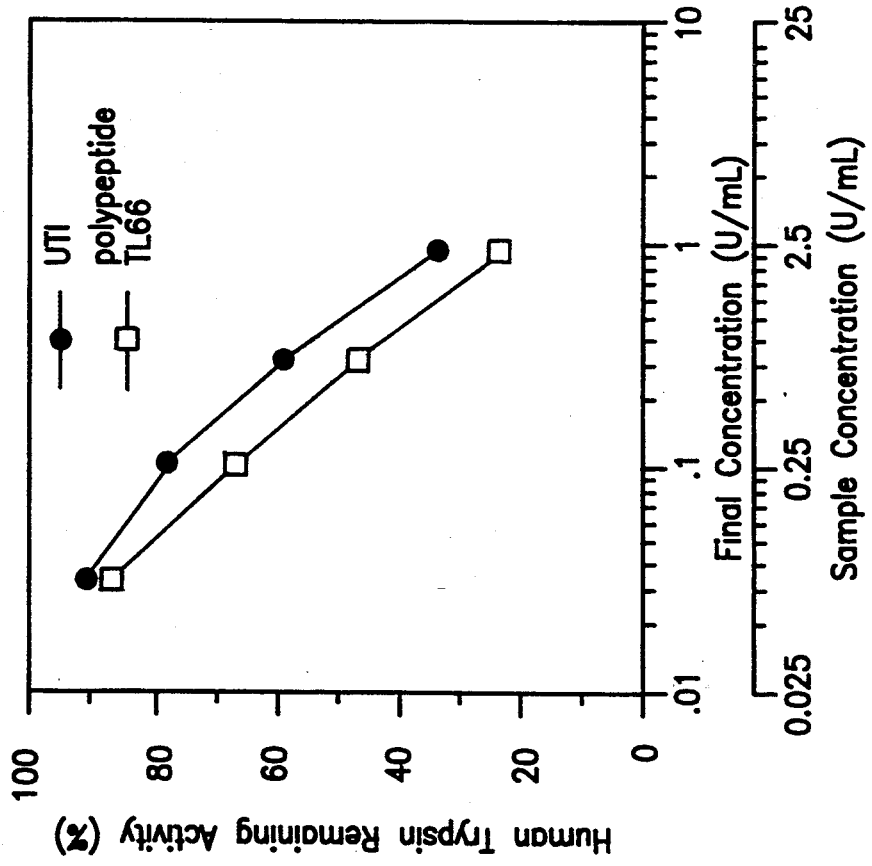
FIG. 14C shows human trypsin-inhibiting activity of polypeptide TL66 of the present invention obtained in Example 3-(4).

Also, the purified sample of TL66 obtained in Example 3-(4) was checked for its human trypsin-inhibiting activity in the same manner. As shown in FIG. 14C, human trypsin-inhibiting activity was found in the polypeptide TL66 obtained in Example 3-(4) similar to the case of the positive control.

(2) Human elastase-inhibiting activity

The purified sample obtained in Example 1-(5) was dissolved in 100 μl of distilled water. Concentration of this solution was determined based on its bovine trypsin-inhibiting activity using the UTI as a standard. The solution was then diluted to various concentration levels with 0.1% BSA/27 mM CaCl$_2$/133 mM Tris-HCl buffer (pH 7.5) for use in the activity measurement. The aforementioned UTI was also diluted in the same manner. Human elastase-inhibiting activities in the test samples and the positive control were measured in accordance with the method of Ogawa et al. (Ogawa,M. et al., *Res. Commun. Chem. Pathol. Pharmacol.*, vol. 55, pp. 271–274, 1987) using a synthetic compound STANA (Peptide Institute Inc.) as a substrate.

Human nuetrophil elastase (Type V, CALBIOCHEM) was dissolved in 27 mM CaCl$_2$/133 mM Tris-HCl buffer (pH 7.5) to a concentration of 100 μg/ml and the solution was further diluted with 0.1% BSA/27 mM CaCl$_2$/133 mM Tris-HCl buffer (pH 7.5) to prepare 4 μg/ml of elastase solution. 100 mM solution of STANA was prepared by dissolving it in N-methyl-2-pyrrolidone and the solution was further diluted with 0.1% BSA/27 mM CaCl$_2$/133 mM Tris-HCl buffer (pH 7.5) to prepare 20 mM of STANA solution.

Next, 50 μl of the test sample or positive control was mixed with 50 μl of the elastase solution and 50 μl of 0.1% BSA/27 mM CaCl$_2$/133 mM Tris-HCl buffer (pH 7.5). After incubation at 37° C. for 10 minutes, 50 μl of the STANA solution was added to the mixture to start the reaction. The reaction was carried out at 37° C. for 20 minutes and then stopped by adding 50 μl of 50% acetic acid solution to the reaction mixture. Thereafter, absorbance at 405 nm was measured using a spectrophotometer.

In this instance, in order to eliminate absorbance of various solutions in the reaction mixture, a blank solution was prepared by mixing 50 μl of the elastase solution with 50 μl of 50% acetic acid and then with 50 μl of each test sample or the positive control, 50 μl of 0.1% BSA/27 mM CaCl$_2$133 mM Tris-HCl buffer (pH 7.5) and with 50 μl of the STANA solution.

Figure 15A:
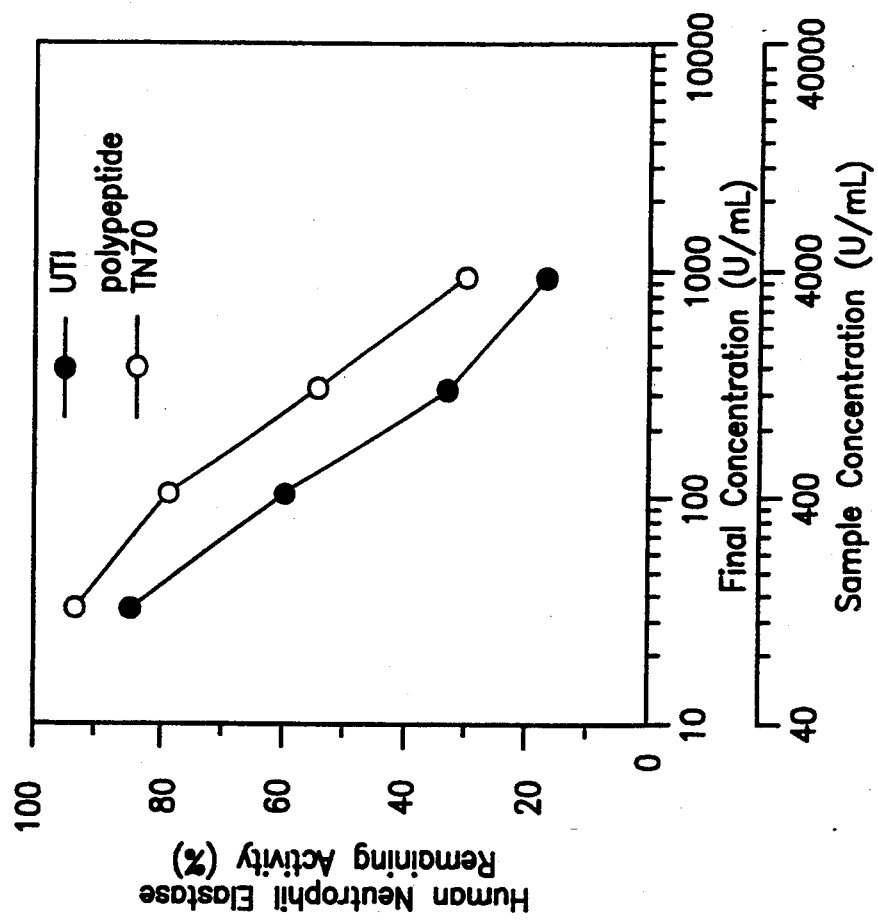
FIG. 15A shows human neutrophil elastase-inhibiting activity of polypeptide TN70 of the present invention obtained in Example 1-(5).

The results are shown in FIG. 15A. In this figure, human elastase remaining activity was expressed by percentage based on the absorbance of a control reaction mixture in which 50 μl of 0.1% BSA/27 mM CaCl$_2$/133 mM Tris-HCl buffer (pH 7.5) was used instead of the test sample or the positive control. As is evident from the figure, human elastase-inhibiting activity was found in the polypeptide TN70 of the present invention obtained in Example 1-(5) similar to the case of the positive control.

In the same manner, the purified sample of CC51 obtained in Example 2-(5) was checked for its human elastase-inhibiting activity. As shown in FIG. 15B, human elastase-inhibiting activity was found in the polypeptide CC51 of the present invention obtained in Example 2-(5) similar to the case of the positive control.

Also, the purified sample of TL66 obtained in Example 3-(4) was checked for its human elastase-inhibiting activity in the same manner. As shown in FIG. 15C, human elastase-inhibiting activity was found in the polypeptide TL66 obtained in Example 3-(4) similar to the case of the positive control.

(3) Plasmin-inhibiting activity

The purified sample obtained in Example 1-(5) was dissolved in 100 μl of distilled water. Concentration of this solution was determined based on its bovine trypsin-inhibiting activity using the aforementioned UTI as a standard. The solution was then diluted to various concentration levels with 0.11M NaCl/50 mM Tris-HCl buffer (pH 7.4) for use in the activity measurement. The UTI was also diluted in the same manner. Using a synthetic compound S-2251 (Daiichi Pure Chemicals Co., Ltd.) as a substrate, human plasmin-inhibiting activities of the diluted test samples and the positive control were measured in accordance with the method of Friberger et al. (Friberger,P. et al., *Haemostasis*, vol. 7, pp. 138–145, 1978).

Human plasma plasmin (Sigma Chemical Co.) was dissolved in physiological saline to a concentration of 1 U/ml and the solution was further diluted with 50% glycerol/2 mM HCl solution to prepare 0.1 U/ml of plasmin solution. 3.5 mM solution of S-2251 was prepared by dissolving it in distilled water.

Next, 50 μl of the test sample or positive control was mixed with 50 μl of the plasmin solution and 100 μl of 0.11M Na Cl/50 mM Tris-HCl buffer (pH 7.4). After incubation at 37° C. for 10 minutes, 50 μl of the S-2251 solution was added to the mixture to start the reaction. The reaction was carried out at 37° C. for 2 minutes and then stopped by adding 25 μl of 50% acetic acid solution to the reaction mixture. Thereafter, absorbance at 405 nm was measured using a spectrophotometer.

In this instance, in order to eliminate absorbance of various solutions in the reaction mixture, a blank solution was prepared by mixing 50 μl of the plasmin solution with 25 μl of 50% acetic acid and then with 50 μl of each test sample or the positive control, 100 μl of 0.11M NaCl/50 mM Tris-HCl buffer (pH 7.4) and with 50 μl of the S-2251 solution.

Figure 16B:
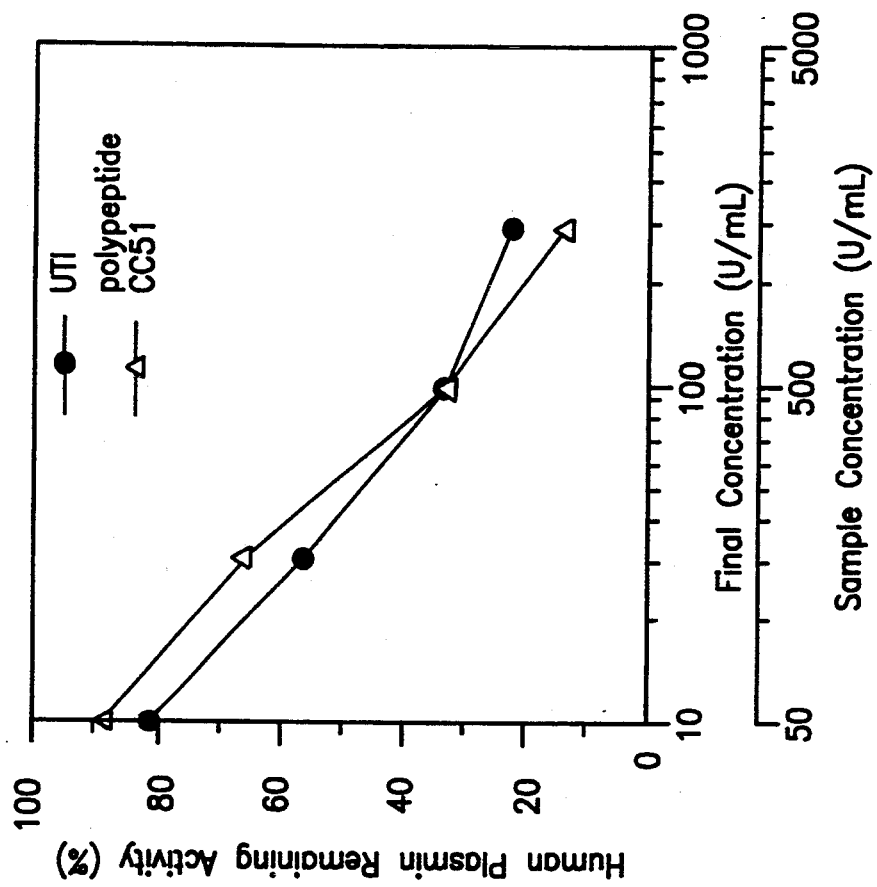
FIG. 16B shows human plasmin-inhibiting activity of polypeptide CC51 of the present invention obtained in Example 2-(5).
Figure 16A:
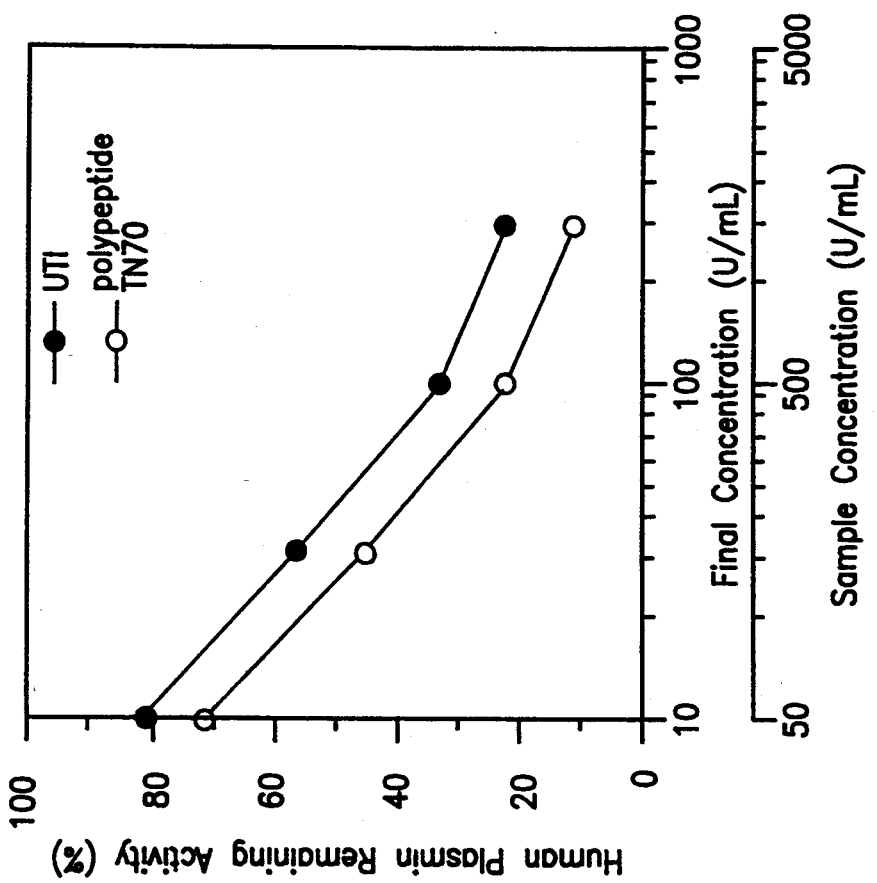
FIG. 16A shows human plasmin-inhibiting activity of polypeptide TN70 of the present invention obtained in Example 1-(5).

The results are shown in FIG. 16A. In this figure, human plasmin remaining activity was expressed by percentage based on the absorbance of a control reaction mixture in which 50 μl of 0.11M NaCl/50 mM Tris-HCl buffer (pH 7.4) was used instead of the test sample or the positive control. As is evident from the figure, human plasmin-inhibiting activity was found in the polypeptide TN70 of the present invention obtained in Example 1-(5) similar to the case of the positive control.

In the same manner, the purified sample of CC51 obtained in Example 2-(5) was checked for its human plasmin-inhibiting activity. As shown in FIG. 16B, human plasmin-inhibiting activity was found in the polypeptide CC51 of the present invention obtained in Example 2-(5) similar to the case of the positive control.

Figure 16C:
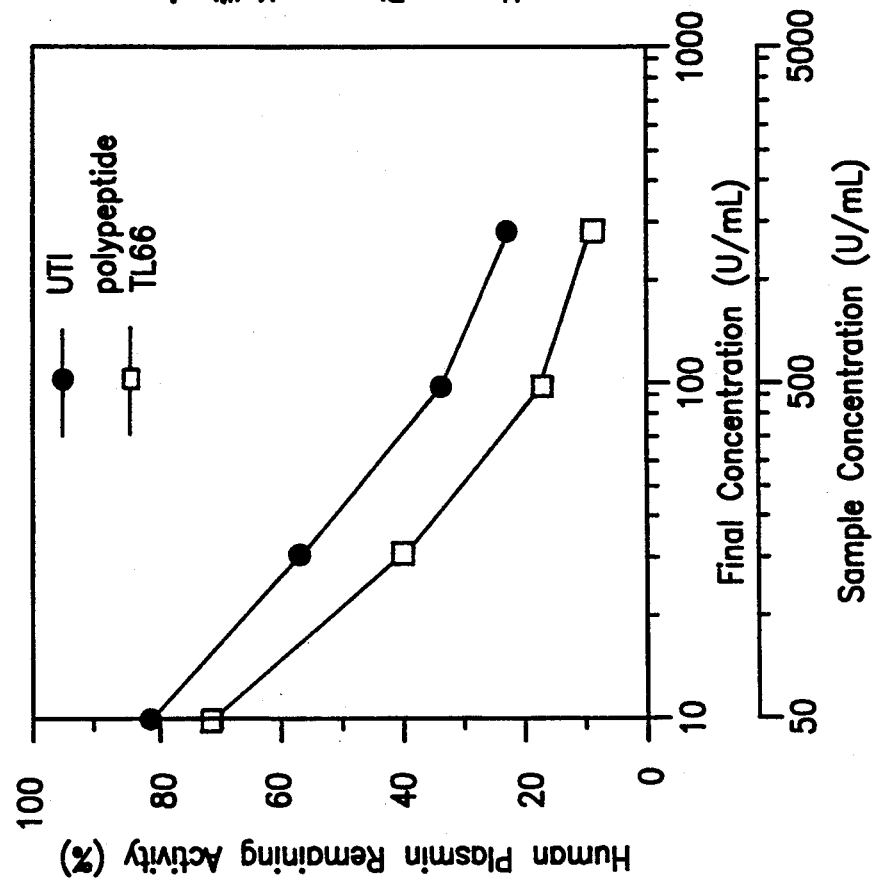
FIG. 16C shows human plasmin-inhibiting activity of polypeptide TL66 of the present invention obtained in Example 3-(4).

Also, the purified sample of TL66 obtained in Example 3-(4) was checked for its human plasmin-inhibiting activity in the same manner. As shown in FIG. 16C, human plasmin-inhibiting activity was found in the polypeptide TL66 obtained in Example 3-(4) similar to the case of the positive control.

(4) Human plasma kallikrein-inhibiting activity

The purified sample obtained in Example 1-(5) was dissolved in 100 μl of distilled water. Concentration of this solution was determined based on its bovine trypsin-inhibiting activity using the aforementioned UTI as a standard. The solution was then diluted to various concentration levels with 0.1% BSA/150 mM NaCl/50 mM Tris-HCl buffer (pH 8.3) for use in the activity measurement. The UTI was also diluted in the same manner. Using a synthetic compound S-2302 (Daiichi Pure Chemicals Co., Ltd.) as a substrate, human plasma kallikrein-inhibiting activities of the diluted test samples and the positive control were measured in accordance with the method of Ohno et al. (Ohno, H. et al., *Thromb. Res.*, vol. 19, pp. 579–588, 1980) as follows.

0.26 U/ml solution of human plasma kallikrein (Sigma Chemical Co.) was diluted with 0.1% BSA/150 mM NaCl/50 mM Tris-HCl buffer (pH 8.3) to prepare 0.08 U/ml of plasma kallikrein solution. 4 mM solution of S-2302 was prepared by dissolving it in distilled water and the solution was further diluted with 0.1% BSA/150 mM NaCl/50 mM Tris-HCl buffer (pH 8.3) to prepare 2 mM solution of S-2302.

Next, 25 μl of the test sample or positive control was mixed with 75 μl of 0.1% BSA/150 mM NaCl/50 mM Tris-HCl buffer (pH 8.3) and 50 μl of the plasma kallikrein solution. After incubation at 37° C. for 10 minutes, 50 μl of the S-2302 solution was added to the mixture to start the reaction. The reaction was carried out at 37° C. for 8 minutes and then stopped by adding 25 μl of 50% acetic acid solution to the reaction mixture. Thereafter, absorbance at 405 nm was measured using a spectrophotometer.

In this instance, in order to eliminate absorbance of various solutions in the reaction mixture a blank solution was prepared by mixing 50 μl of the plasma kallikrein solution with 25 μl of 50% acetic acid and then with 25 μl of each test sample or the positive control, 75 μl of 0.1% BSA/150 mM 50 mM Tris-HCl buffer (pH 8.3) and with 50 μl of the S-2302 solution.

Figure 17A:
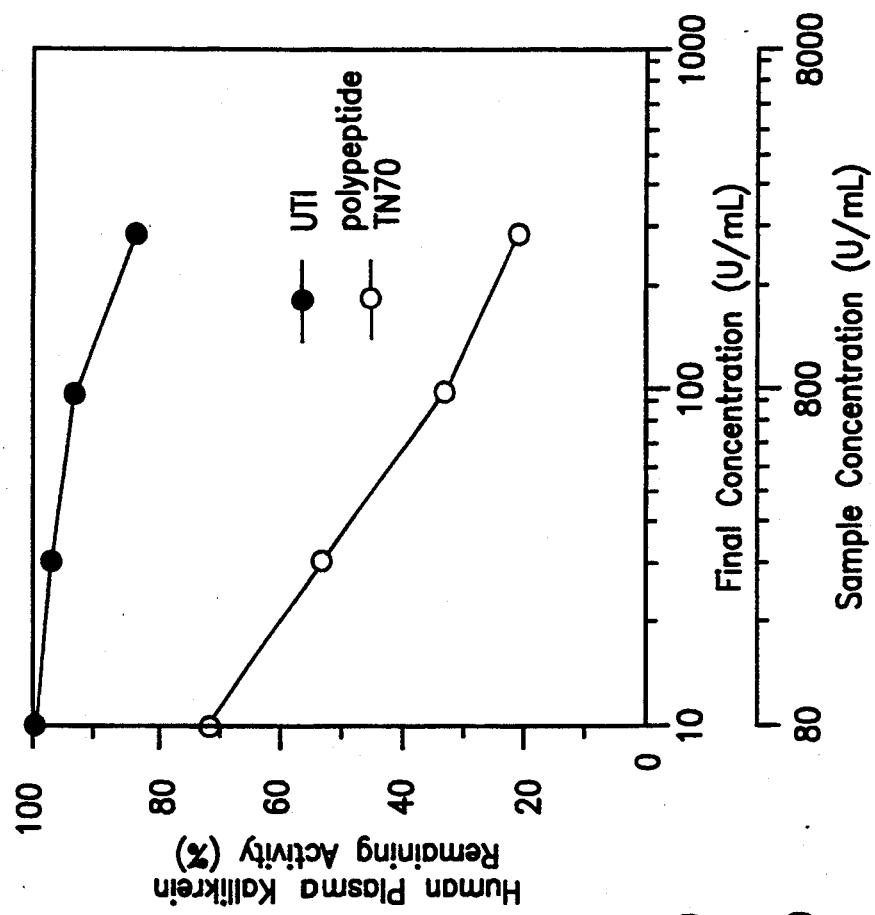
FIG. 17A shows human plasma kallikrein-inhibiting activity of polypeptide TN70 of the present invention obtained in Example 1-(5).

The results are shown in FIG. 17A. In this figure, human plasma kallikrein remaining activity was expressed by percentage based on the absorbance of a control reaction mixture in which 25 μl of 0.1% BSA/150 mM NaCl/50 mM Tris-HCl buffer (pH 8.3) was used instead of the test sample or the positive control. As is evident from the figure, human plasma kallikrein-inhibiting activity was found in the polypeptide TN70 of the present invention obtained in Example 1-(5), while such an activity was not found in the positive control.

In the same manner, the purified sample of CC51 obtained in Example 2-(5) was checked for its human plasma kallikrein-inhibiting activity. As shown in FIG. 17B, human plasma kallikrein-inhibiting activity was found in the polypeptide CC51 of the present invention obtained in Example 2-(5), while such an activity was not found in the positive control.

Also, the purified sample of TL66 obtained in Example 3-(4) was checked for its human plasma kallikrein-inhibiting activity in the same manner. As shown in FIG. 17C, human plasma kallikrein-inhibiting activity was found in the polypeptide TL66 obtained in Example 3-(4), while such an activity was not found in the positive control.

(5) Human FXa-inhibiting activity

The purified sample obtained in Example 1-(5) was dissolved in 100 μl of distilled water. Concentration of this solution was determined based on its bovine trypsin-inhibiting activity using the aforementioned UTI as a standard. The solution was then diluted to various concentration levels with 0.1% BSA/150 mM NaCl/5 mM $CaCl_2$/50 mM Tris-HCl buffer (pH 8.3) for use in the activity measurement. The UTI was also diluted in the same manner. Using a synthetic compound S-2222 (Daiichi Pure Chemicals Co., Ltd.) as a substrate, human FXa-inhibiting activities of the diluted test samples and the positive control were measured in accordance with the method of Ohno et al. (Ohno, H. et al., *Thromb. Res.*, vol. 19, pp. 579–588, 1980) as follows.

Human FXa (American Diagnostica Inc.) was dissolved in distilled water to a concentration of 10 PEU/ml and the solution was further diluted with 0.1% BSA/150 mM NaCl/5 mM $CaCl_2$/50 mM Tris-HCl buffer (pH 8.3) to prepare 0.1 PEU/ml of FXa solution. 4 mM solution of S-2222 was prepared by dissolving it in distilled water and the solution was further diluted with 0.1% BSA/150 mM NaCl/5 mM $CaCl_2$/50 mM Tris-HCl buffer (pH 8.3) to obtain 2 mM solution of S-2222.

Next, 25 μl of the test sample or positive control was mixed with 100 μl of 0.1% BSA/150 mM NaCl/5 mM $CaCl_2$/50 mM Tris-HCl buffer (pH 8.3) and 25 μl of the FXa solution. After incubation at 37° C. for 10 minutes, 100 μl of the S-2222 solution was added to the mixture to start the reaction. The reaction was carried out at 37° C. for 30 minutes and then stopped by adding 50 μl of 50% acetic acid solution to the reaction mixture. Thereafter, absorbance at 405 nm was measured using a spectrophotometer.

In this instance, in order to eliminate absorbance of various solutions in the reaction mixture, a blank solution was prepared by mixing 25 μl of the FXa solution with 50 μl of 50% acetic acid and then with 25 μl of each test sample or the positive control, 100 μl of 0.1% BSA/150 mM NaCl/5 mM $CaCl_2$/50 mM Tris-HCl buffer (pH 8.3) and with 100 μl of the S-2222 solution.

Figure 18B:
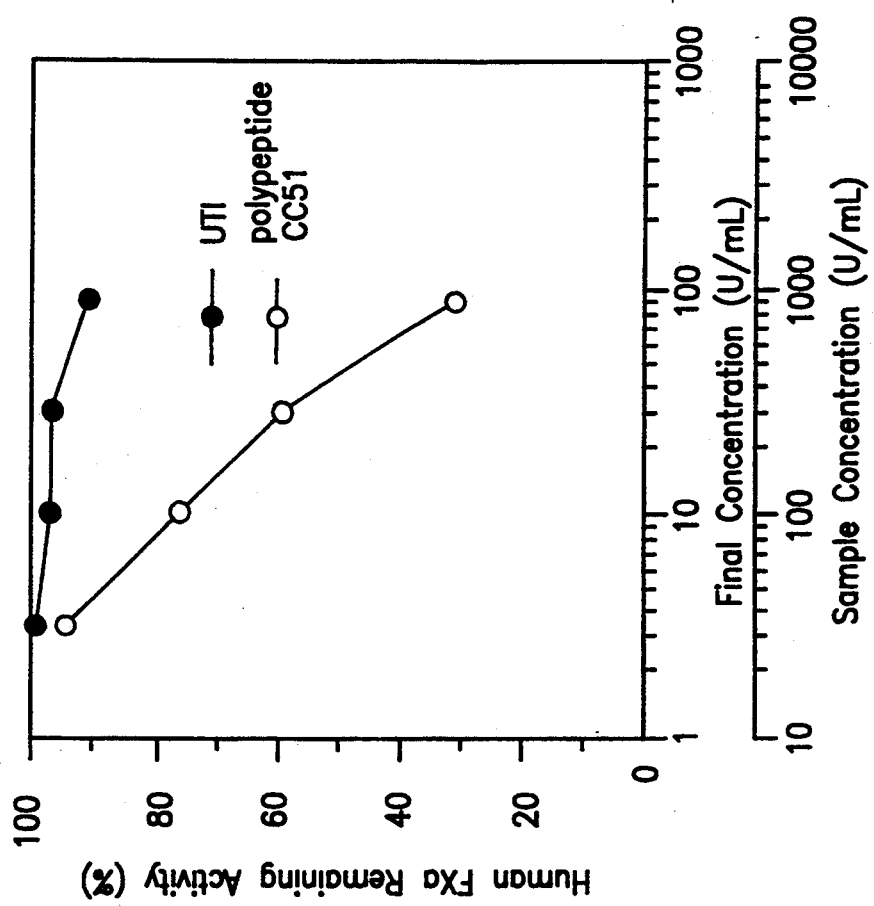
FIG. 18B shows human FXa-inhibiting activity of polypeptide CC51 of the present invention obtained in Example 2-(5).
Figure 18A:
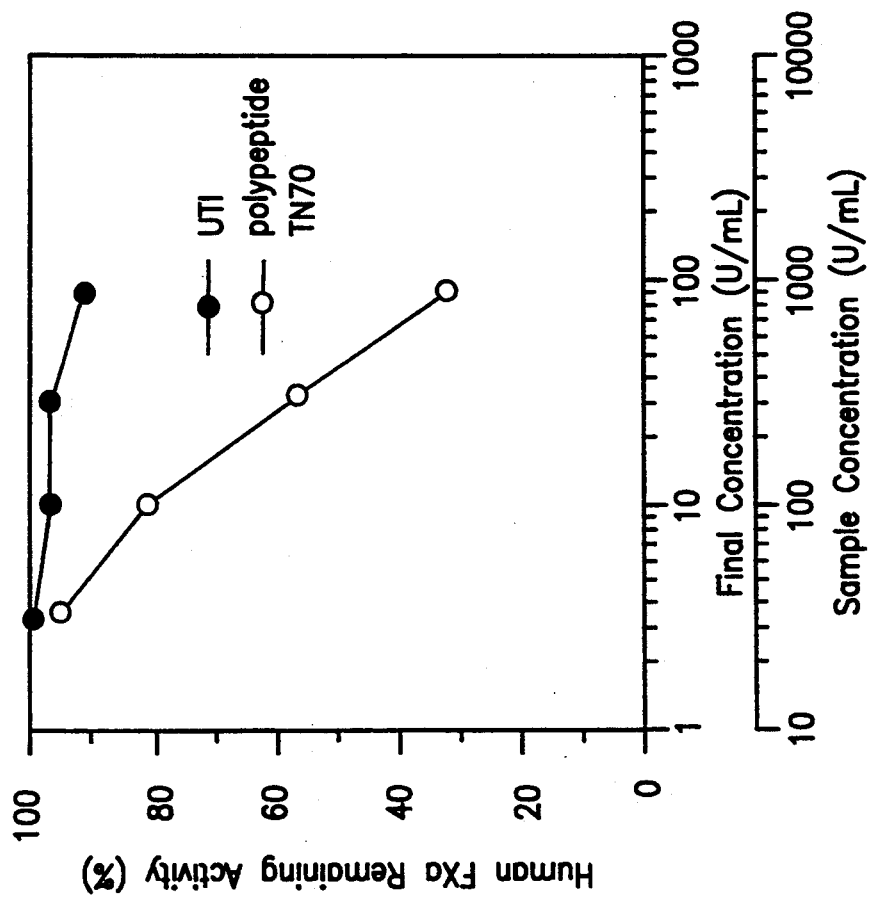
FIG. 18A shows human FXa-inhibiting activity of polypeptide TN70 of the present invention obtained in Example 1-(5).

The results are shown in FIG. 18A. In this figure, human FXa remaining activity was expressed by percentage based on the absorbance of a control reaction mixture in which 25 μl of 0.1% BSA/150 mM NaCl/5 mM $CaCl_2$/50 mM Tris-HCl buffer (pH 8.3) was used instead of the test sample or the positive control. As is evident from FIG. 18A, human FXa-inhibiting activity was found in the polypeptide TN70 of the present invention obtained in Example 1-(5), while such an activity was not found in the positive control.

In the same manner, the purified sample of CC51 obtained in Example 2-(5) was checked for its human FXa-inhibiting activity. As shown in FIG. 18B, human FXa-inhibiting activity was found in the polypeptide CC51 of the present invention obtained in Example 2-(5), while such an activity was not found in the positive control.

Figures 18C, 19:
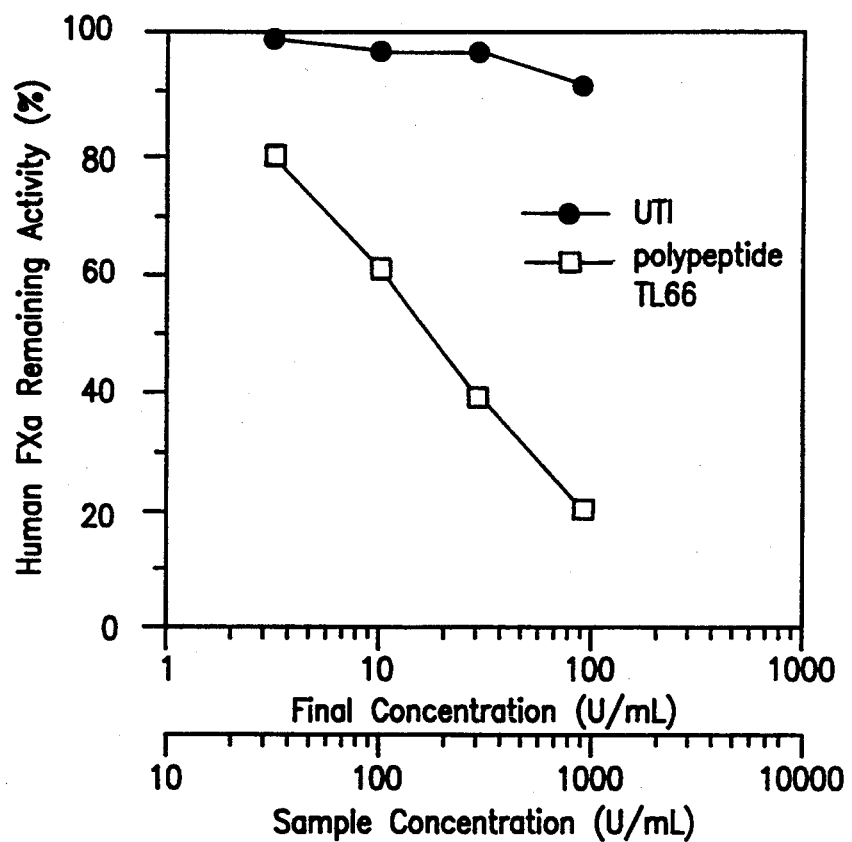
FIG. 18C shows human FXa-inhibiting activity of polypeptide TL66 of the present invention obtained in Example 3-(4).
FIG. 19 shows a nucleotide sequence (SEQ ID NO: 87) of oligomer Y46E.

Also, the purified sample of TL66 obtained in Example 3-(4) was checked for its human FXa-inhibiting activity in the same manner. As shown in FIG. 18C, human FXa-inhibiting activity was found in the polypeptide TL66 obtained in Example 3-(4), while such an activity was not found in the positive control.

(6) Measurement of Activated Partial Thromboplastin Time

The COAGTEC (TE-600, ERMA OPTICAL WORKS LTD), a measurement instrument, was used and the following operation was conducted at 37° C. to measure the effect of polypeptide of the present invention on activated partial thromboplastin time (hereinafter abbreviated as aPTT).

First, purified samples obtained in Example 1 (5), Example 2 (5) and Example 3 (4) were dissolved in 100 μl of distilled water. Concentration of each solution was determined based on bovine trypsin-inhibiting activity using UTI as a standard. Each solution was then diluted to various concentration levels for activity measurement.

Afterward, 50 μl of the ORTHO Plasma Coagulation Control Level 1 (Ortho Diagnostic Systems Co., Ltd.) was put into glass tubes. 50 μl of the sample or 50 μl of distilled water as control was added. Furthermore, 100 μl of the Activated THROMBOFAX Reagent-Optimized (Ortho Diagnostic Systems Co., Ltd.) was added and then each glass tube was set in the apparatus. 100 μl of 0.02M $CaCl_2$ was then added to each glass tube for the measurement, and aPTT for each test samples and the control was obtained.

The results of the measurement were shown in Table 1. The aPTT values of the samples are descried in percentage when taking the aPTT value of control as 100%.

As obvious from Table 1, it has been verified that the polypeptide TN70 of the present invention obtained in Example 1(5), the polypeptide CC51 of the present invention obtained in Example 2(5) and the polypeptide TL66 obtained in Example 3(4) have an effect to extend aPTT and anticoagulant activity.

TABLE 1

| | Final Concentration (U/ml) | aPTT (%) |
|---|---|---|
| Control | — | 100 |
| Purified sample obtained in Example 1(5) | 33 | 155 |
| | 167 | 230 |
| Purified sample obtained in Example 2(5) | 33 | 172 |
| | 167 | 256 |
| Purified sample obtained in Example 3(4) | 33 | 157 |
| | 167 | 239 |

Example 5

Production of inventive novel polypeptide making use of inventive novel DNA fragment—Part 3

(1) Cloning of novel DNA fragment of the invention

Cloning of a DNA fragment encoding a polypeptide of the present invention (to be referred to as "Y46E" hereinafter as a matter of convenience) which is defined by the aforementioned amino acid sequence of formula 5 was carried out by means of site-directed mutagenesis in the light of the method of Kunkel et al. (Kunkel, T. A. et al., *Methods in Enzymology*, vol.154, p.367, 1987) using plasmid pM552 obtained in Example 1-(3).

Firstly, site-directed mutagenesis was carried out using the M13 phage obtained in Example 2-(1), making use of a Mutan TM -K kit (Takara Shuzo Co., Ltd.) and according to the manufacturer's instructions. An *E. coli* strain BW313 (HfrKL16PO/45 [lysA(61–62)], dut1, ung1, thi-1, relA1) attached to the kit as an indicator was infected with the M13 phage to obtain phage plaques. A single plaque was inoculated into 2×YT medium using the BW313 as an indicator and cultured at 37° C. for 6 hours. Thereafter, ssDNA was extracted and purified from the resulting phage culture broth. Separately from this, an oligomer Y46E (SEQ ID NO: 87) (FIG. 19) for mutation introduction use was synthesized using the aforementioned chemical synthesizer and purified using the aforementioned OPC column, and the 5'-end of the purified oligomer was phosphorylated using T4 polynucleotide kinase and ATP. The thus phosphorylated oligomer was subjected to annealing with the just obtained ssDNA by incubating them at 65° C. for 15 minutes and then at 37° C. for 15 minutes. The resulting reaction mixture was then incubated at 25° C. for 2 hours in the presence of *E. coli* DNA ligase and T4 DNA polymerase attached to the Mutan TM -K kit to synthesize a complementary chain. After terminating the reaction with EDTA, the resulting reaction mixture was transfected into *E. coli* BMH 71–18 mutS (Δ(lac-proAB), thi, supE, mutS215::Tn10(tet$^r$)/F' traD36, proAB lacIqZΔM15) attached to the kit, and phage plaques were obtained using JM109 as indicator. Phage particles were recovered from the thus obtained plaques and cultured using JM109 as an indicator to obtain phage solutions from which ssDNA samples were extracted and purified. Thereafter, nucleotide sequence of each ssDNA sample was determined using the aforementioned DNA sequencer to select an ssDNA into which desired mutation has been introduced.

Next, PCR was carried out in accordance with the procedure described in Example 2-(1) using the thus obtained ssDNA as a template. In this instance, ScaI sense primer (SEQ ID NO: 77) (FIG. 8A) prepared in Example 2-(1) was used as the sense primer, and pa01 (SEQ ID NO: 67) (FIG. 4B) prepared in Example 1-(2) as the antisense primer.

(2) Construction of expression vector

Figure 20:
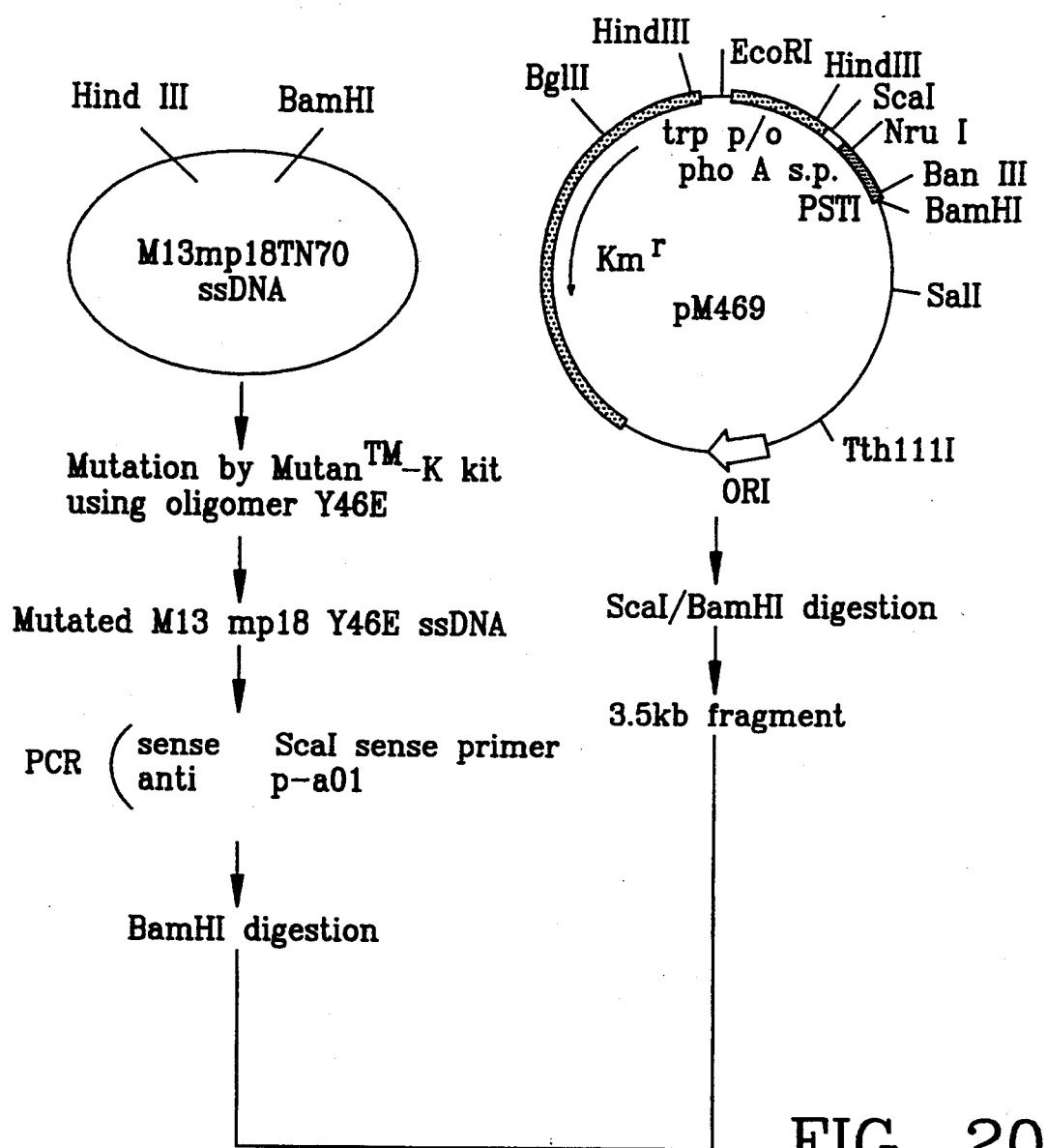
FIG. 20 shows a process for the construction of plasmid pM575B.

Using the amplified product thus obtained in the above procedure (1), an expression vector containing a DNA fragment of the present invention which encodes the inventive polypeptide Y46E was constructed as shown in FIG. 20. Firstly, plasmid pM469 was double-digested with ScaI and BamHI to obtain a DNA fragment of about 3.5 kb. Next, the amplified product obtained in the above procedure (1) was digested with BamHI and then ligated with the just obtained DNA fragment of about 3.5 kb to obtain an expression plasmid pM575B (cf. FIG. 20).

The thus obtained plasmid pM575B was double-digested with HindIII and BamHI, and a DNA fragment of about 310 bp was extracted and purified. The purified DNA fragment was ligated with each of the aforementioned phage vectors M13mp18 and M13mp19 which have been double-digested with HindIII and BamHI in advance. Thereafter, *E. coli* JM109 was transfected with the resulting ligation mixture to obtain M13 phage culture from which ssDNA was extracted and purified and subjected to sequencing using the aforementioned DNA sequencer. Thus confirmed nucleotide sequence of a region of plasmid pM575B from its HindIII recognition site to BamHI recognition site containing the DNA fragment of interest and its encoded amino acid sequence are shown in FIG. 21 (Sequence Nos. 88 and 89 in the Table of Sequence).

(3) Preparation and cultivation of transformant

A transformant, *E. coli* JE5505 (pM575B), was prepared by transforming *E. coli* JE5505 with the expression plasmid pM575B obtained in the above procedure (2) in accordance with the Hanahan's method. The transformant was cultured in the same protocol as described in Example 1-(4) and culture supernatant was prepared from the resulting culture broth by centrifugation.

Culture supernatant thus prepared was diluted with 0.1% BSA/0.2M triethanolamine-HCl buffer (pH 7.8) to each predetermined concentration, and the diluted samples were used for the measurement of trypsin-inhibiting activity in accordance with the procedure described in Example 4-(1). In this instance, culture supernatant of a transformant, *E. coli* JE5505 (pM553), was used as a control which has been obtained in Example 1-(4).

As the results, markedly high trypsin-inhibiting activity was found in the culture supernatant of *E. coli* JE5505 (pM575B) in comparison with the control. The transformant *E. coli* JE5505 (pM575B) has been deposited by the present inventors on Jul. 16, 1991, in Fermentation Research Institute, Agency of Industrial Science and Technology, and has been assigned the designation as FERM BP-3613.

(4) Purification of inventive polypeptide from culture supernatant of *E. coli* JE5505 (pM575B)

The polypeptide of the present invention was recovered and purified from culture supernatant of the transformant *E. coli* JE5505 (pM575B) obtained in the above procedure (3).

(a) Ammonium sulfate fractionation

Ammonium sulfate was added to one liter of the culture supernatant to a level of 80% saturation. The mixture was stirred until ammonium sulfate was completely dissolved and then the resulting solution was allowed to stand overnight at 4° C. The sample was subjected to centrifugation at 12,000×g, for 30 minutes at 4° C., and the thus obtained pellet was dissolved in 25 ml of distilled water. After removing insoluble materials by centrifugation, the resulting supernatant was concentrated to 1 ml using an ultrafiltration membrane (molecular weight cutoff of 1,000; Diaflow membrane YM-1, Grace Company). Thereafter, the concentrated sample was centrifuged at 5860×g for 10 minutes at 4° C. to recover supernatant fluid.

(b) Gel filtration chromatography

The concentrated sample obtained in the above step (a) was applied to Sephadex G-50 column (1 cm$\phi$×115 cm, Pharmacia) which has been equilibrated with PBS⁻ and then eluted at a flow rate of 0.2 ml/min and at 4° C. Each 2 ml solution was fractionated.

A portion of each fraction was checked for its trypsin-inhibiting activity in accordance with the procedure described in Example 4-(1). Thereafter, active fractions were pooled and dialyzed overnight at 4° C. against 20 mM Tris-HCl buffer (pH 8.0) using a dialysis membrane (molecular weight cutoff of 1,000; Spectrum Medical Industries, Inc.).

(c) Anion exchange chromatography

The dialyzed sample obtained in the above step (b) was applied to Mono Q column (5 mm$\phi$×50 mm, Pharmacia) which has been equilibrated with 20 mM Tris-HCl (pH 8.0). Using an FPLC system (Pharmacia), elution was carried out at a flow rate of 1 ml/min with a linear density gradient of 0 to 0.4M NaCl/20 mM Tris-HCl (pH 8.0)/48 min. Protein concentration in the eluent was monitored at 280 nm and each protein peak was fractionated. A portion of each fraction was checked for its trypsin-inhibiting activity in accordance with the procedure described in Example 4-(1) and active fraction was used in the following reverse phase chromatography.

(d) Reverse phase chromatography

The active fraction obtained in the above step (c) was applied to Vydac C18 column (4.6 mm$\phi$×25.0 cm, Separations Group) which has been equilibrated with 0.04% trifluoroacetic acid solution. Using the aforementioned Waters 625 LC system, elution was carried out at a flow rate of 1 ml/min with a linear density gradient of 0 to 100% acetonitrile/0.04% trifluoroacetic acid/30 min. Protein concentration in the eluent was monitored at 280 nm and each protein peak was fractionated. A portion of each fraction was checked for its trypsin-inhibiting activity in accordance with the procedure described in Example 4-(1) and active fractions were pooled. The pooled sample was dried under a reduced pressure using a centrifugation vacuum concentrator (Tomy Seiko Co., Ltd.). The purified sample was subjected to the following SDS-PAGE (5), amino acid sequence analysis (6) and activity measurement in Example 7.

(5) SDS-PAGE

The purified sample obtained in the above procedure (4) was subjected to SDS-PAGE in accordance with the procedure described in Example 1-(6). After the electrophoresis, staining was carried out with the aforementioned commercial silver staining kit.

The purified sample showed a single band by SDS-PAGE.

(6) Determination of amino acid sequence

The purified sample obtained in the above procedure (4) was dissolved in 50% acetic acid solution and its amino acid sequence was determined in accordance with the procedure described in Example 1-(7). As the results, it was confirmed that the purified sample of the foregoing procedure (4) is the aimed polypeptide Y46E of the present invention (cf. Sequence No. 89 of the Sequence Listing).

Example 6

Production of inventive novel polypeptide making use of inventive novel DNA fragment—Part 4

(1) Construction of plasmid pM558

A plasmid pM558 to be used in procedure (2) of this example as a template of PCR was prepared from plasmid pM552 obtained in Example 1-(3) in the same protocol as in Example 5-(1). The plasmid pM558 contains a nucleotide sequence which encodes a modified amino acid sequence of the foregoing formula 3 resulting from the replacement of its first and second N-terminus amino acids Thr and Val by Asp and Asp, respectively.

Figure 22A:
FIG. 22A shows a nucleotide sequence (SEQ ID NO: 90) of oligomer TV12DD.

Firstly, an oligomer TV12DD (FIG. 22A) for mutation introduction use was synthesized using the aforementioned chemical synthesizer and purified using the aforementioned OPC column. Next, ssDNA was prepared using M13 phage obtained in Example 2-(1) from E. coli JM109, in the same manner as in Example 5-(1) making use of the aforementioned Mutan TM -K kit, and the desired mutation was introduced into the ssDNA using oligomer TV12DD. Thereafter, PCR was carried out in accordance with the procedure described in Example 5-(1) using the thus mutation-introduced ssDNA as a template. In this instance, ScaI sense primer (SEQ ID NO: 77) (FIG. 8A) prepared in Example 2-(1) was used as the sense primer and an M13 primer RV (Takara Shuzo Co., Ltd.) was used as the antisense primer.

The thus obtained PCR product was digested with BamHI and introduced into plasmid pM469 in the same manner as in Example 1-(3) to obtain plasmid pM558.

(2) Cloning of DNA fragment

Cloning of a DNA fragment encoding a polypeptide of the present invention (to be referred to as "Q19K" hereinafter as a matter of convenience) which is defined by the aforementioned amino acid sequence of formula 6 was carried out by means of site-directed mutagenesis in the light of the method of Landt et al., using the plasmid pM558 obtained in the above procedure (1) as a template for PCR use.

Figure 22B:
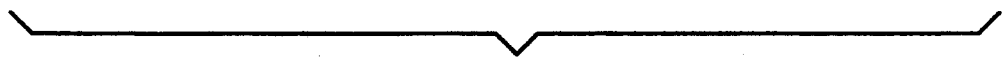
FIG. 22B shows a nucleotide sequence (SEQ ID NO: 91) of antisense primer, p-a05.

Firstly, p-a05 (SEQ ID NO: 91) (FIG. 22B) to be used as an antisense primer in PCR was synthesized using the aforementioned chemical synthesizer and purified using the aforementioned OPC column. PCR was carried out in accordance with the procedure described in Example 1-(2), using plasmid pM558 as the template, HindIII sense primer (FIG. 9A) prepared in Example 2-(2) as the sense primer and the just synthesized p-a05 as the antisense primer. A portion of the amplified product by PCR was applied to 1.5% agarose gel electrophoresis to confirm formation of a DNA fragment having a size of about 160 bp. The amplified product containing the DNA fragment of interest was then extracted and purified from the gel by means of phenol treatment and ethanol precipitation.

The thus purified DNA fragment was dissolved in TE buffer, and secondary PCR was carried out in the same protocol as the above primary PCR using the thus dissolved DNA fragment as the sense primer and the plasmid pM558 as the template. In this instance, BamHI antisense primer (SEQ ID NO: 81) (FIG. 9C) prepared in Example 2-(2) was used as the antisense primer.

A portion of the amplified product by the secondary PCR was applied to 1.5% agarose gel electrophoresis to confirm formation of a DNA fragment having a size of about 350 bp.

(3) Construction of expression vector

Figure 23:
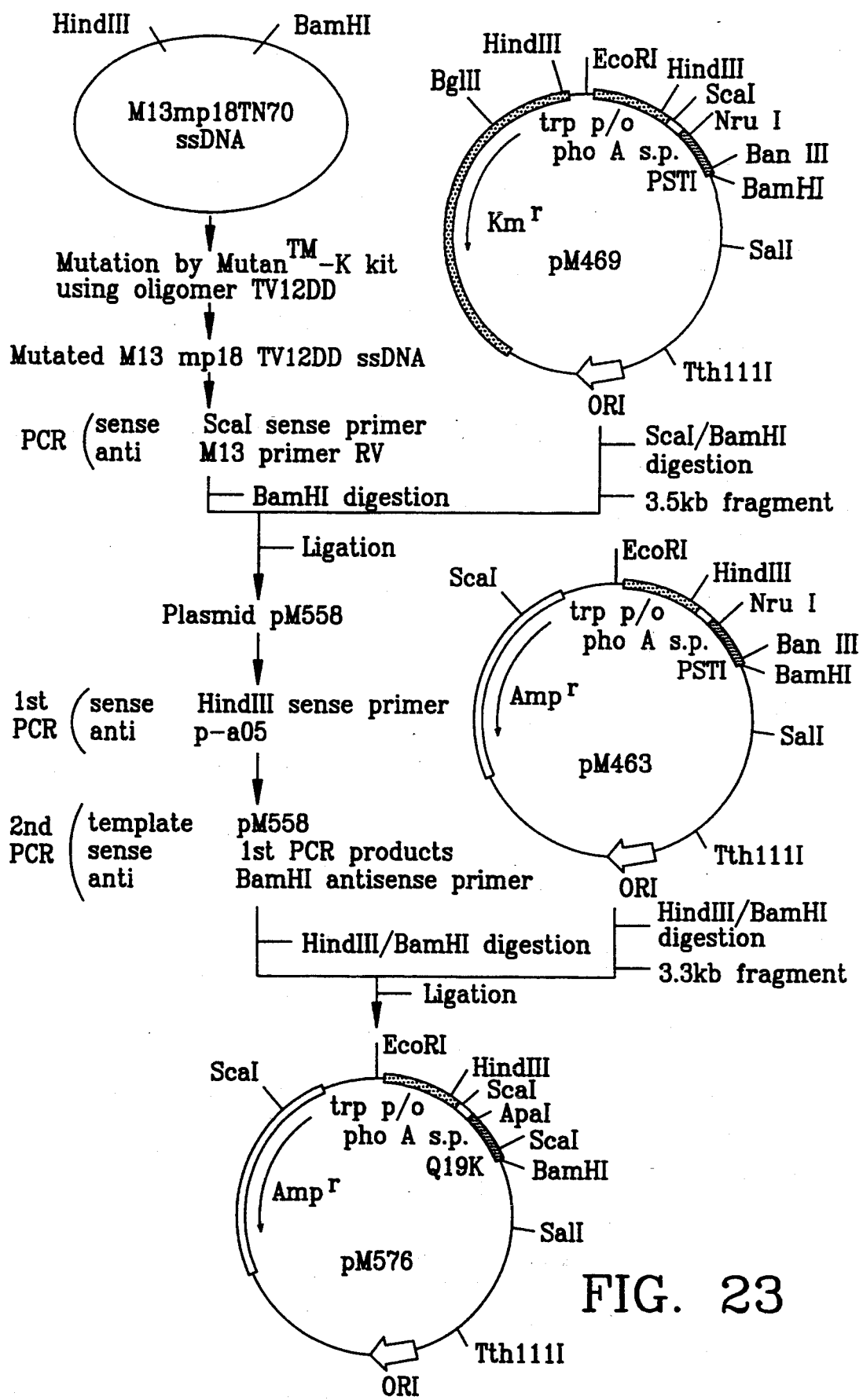
FIG. 23 shows a process for the construction of plasmid pM576.

An expression vector containing a DNA fragment of the present invention which encodes the inventive polypeptide Q19K was constructed by incorporating the amplified product obtained in the above procedure (2) into plasmid pM463 in accordance with the process described in Example 2-(3) (cf. FIG. 23). The thus obtained expression vector, plasmid pM576, was double-digested with HindIII and BamHI, and a DNA fragment of about 310 bp was extracted and purified. The thus purified DNA fragment of interest was ligated with each of the aforementioned phage vectors M13mp18 and M13mp19 which have been double-digested with HindIII and BamHI in advance. Thereafter, E. coli JM109 was transfected with the resulting ligation mixture to obtain M 13 phage culture from which ssDNA was extracted and purified and subjected to sequencing using the aforementioned DNA sequencer. Thus confirmed nucleotide sequence of a region of plasmid pM576 from its HindIII recognition site to BamHI recognition site containing the novel DNA fragment of the present invention and its encoded amino acid sequence are shown in FIG. 24 (cf. Sequence Nos: 92 and 93 in the Sequence Listing).

(4) Preparation and cultivation of transformant

By transforming E. coli JE5505 with the expression plasmid pM576 obtained in the above procedure (3) in accordance with the Hanahan's method, a transformant, E. coli JE5505 (pM576), was isolated which was subsequently cultured in the same protocol as in Example 2-(4) to recover its culture supernatant.

The culture supernatant thus prepared was diluted with 0.1% BSA/0.2M triethanolamine-HCl buffer (pH 7.8) to each predetermined concentration, and the diluted samples were used for the measurement of trypsin-inhibiting activity in accordance with the procedure described in Example 4-(1). In this instance, culture supernatant of a transformant E. coli JE5505 (pM463C) obtained in Example 2-(4) was used as a control. As the results, markedly high trypsin-inhibiting activity was found in the culture supernatant of E. coli JE5505 (pM576) in comparison with the control.

The transformant E. coli JE5505 (pM576) has been deposited by the present inventors on Jul. 16, 1991, in Fermentation Research Institute, Agency of Industrial Science and Technology, and has been assigned the designation as FERM BP-3614.

(5) Purification of inventive novel polypeptide from culture supernatant of E. coli JE5505 (pM576)

The polypeptide of the present invention was purified from four liters of culture supernatant obtained in the above procedure (4) by means of ammonium sulfate fractionation, gel filtration, anion exchange chromatography in (20mM Tris-HCL buffer, PH8.5) and reverse phase chromatography in accordance with the procedure described in Example 5-(4). The obtained purified sample was used for the following SDS-PAGE (6), amino acid sequence analysis (7) and activity measurement in Example 7.

(6) SDS-PAGE

The purified sample obtained in the above procedure (5) was subjected, to SDS-PAGE in accordance with the procedure described in Example 1-(6).

After the electrophoresis, staining was carried out with the aforementioned commercial silver staining kit.

The purified protein showed a single band by SDS-PAGE.

(7) Determination of amino acid sequence

The purified sample obtained in the above procedure (5) was dissolved in 50% acetic acid solution and its amino acid sequence was determined in accordance with the procedure described in Example 1-(7).

As the results, it was confirmed that the purified sample of the foregoing procedure (5) is the aimed polypeptide Q19K of the present invention (cf. Sequence No: 93 of Table of Sequence).

Example 7

Measurement of enzyme-inhibiting activities-2

The following experiments were carried out in order to compare human trypsin-inhibiting activities and human FXa-inhibiting activities of the polypeptides Y46E and Q19K of the present invention obtained in Examples 5-(4) and 6-(5), respectively, with those of the polypeptides TN70 obtained in Example 1-(5) and TL66 obtained in Example 3-(4). The concentrations of Y46E and Q19K was expressed as U/ml of bovine trypsin-inhibiting activity based on UTI in accordance with the procedure described in Example 4.

(1) Trypsin-inhibiting activity

Each of the purified products obtained in Examples 5-(4), 1-(5) and 3-(4) was dissolved in 100 μl of distilled water. Using UTI as standard, bovine trypsin inhibiting activity of each sample was measured. Thereafter, each solution was diluted to various concentration levels with 0.1% BSA/0.2M triethanolamine-HCl buffer (pH 7.8), and the diluted samples were checked for their human trypsin-inhibiting activities in accordance with the procedure described in Example 4-(1).

As the results, human trypsin-inhibiting activity of the polypeptide Y46E of the present invention obtained in Example 5-(4) was found be almost the same as those of the polypeptides TN70 obtained in Example 1-(5) and TL66 obtained in Example 3-(4).

In the same way, trypsin-inhibiting activity of the purified product obtained in Example 6-(5) was compared to those of the purified products obtained in Examples 1-(5) and 3-(4). As the results, human trypsin-inhibiting activity of the polypeptide Q19K of the present invention obtained in Example 6-(4) was found be almost the same as those of the polypeptides TN70 obtained in Example 1-(5) and TL66 obtained in Example 3-(4).

(2) FXa-inhibiting activity

Each of the purified products obtained in Examples 5-(4) and 1-(5) was dissolved in 100 μl of distilled water. Using UTI as standard, bovine trypsin inhibiting activity of each sample was measured. Thereafter, each solution was diluted to various concentration levels with 0.1% BSA/150 mM NaCl/5 mM $CaCl_2$/50 mM Tris-HCl buffer (pH 8.3), and the diluted samples were checked for their FXa-inhibiting activities in accordance with the procedure described in Example 4-(5).

Figure 25:
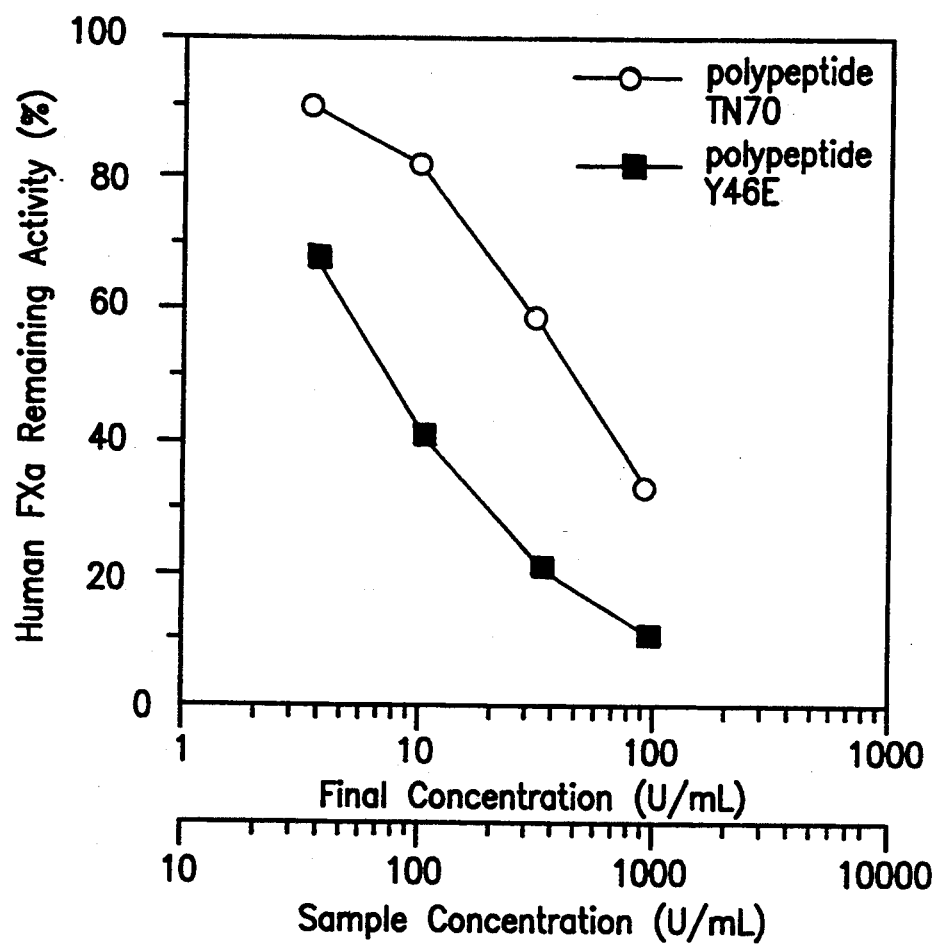
FIG. 25 shows human FXa-inhibiting activity of polypeptide Y46E of the present invention obtained in Example 5-(4).

The results are shown in FIG. 25. In this figure, human FXa remaining activity was expressed by percentage based on the absorbance of a control reaction mixture in which 25 μl of 0.1% BSA/150 mM NaCl/5 mM $CaCl_2$/50 mM Tris-HCl buffer (pH 8.3) was used instead of the test sample.

As is evident from the figure, the polypeptide Y46E of the present invention obtained in Example 5-(4) showed about 7 times higher human FXa-inhibiting activity than that of the polypeptides TN70 obtained in Example 1-(5).

Figures 26, 27:
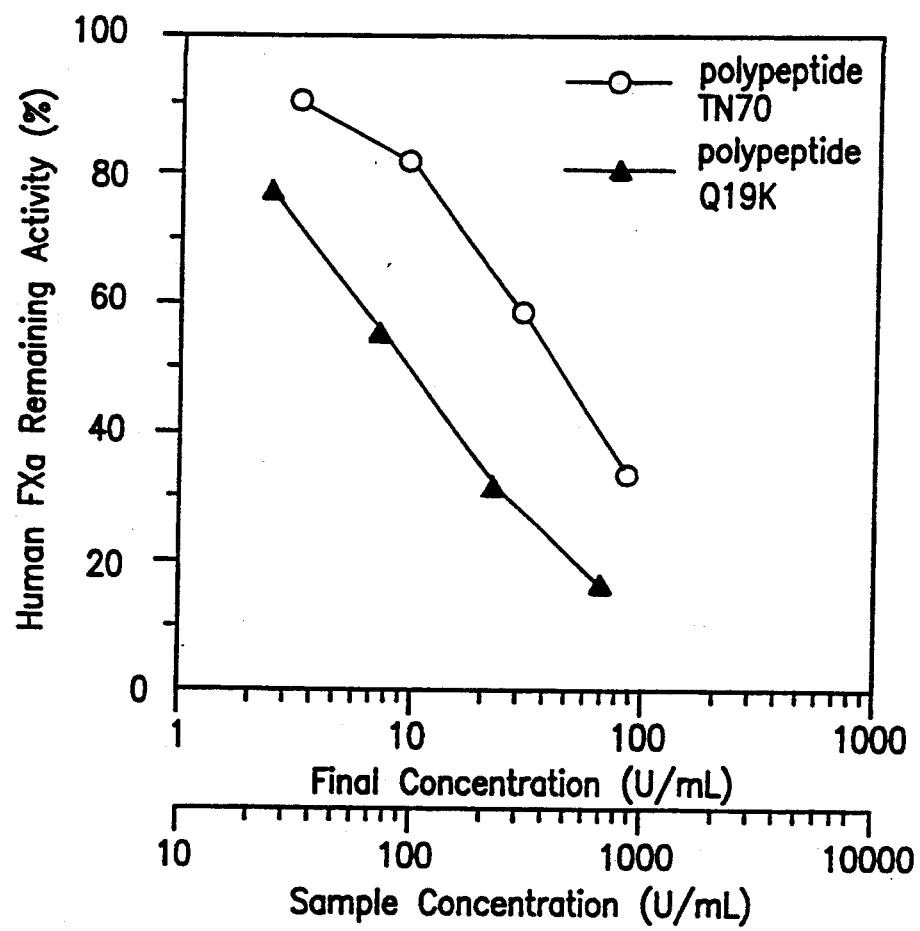
FIG. 26 shows human FXa-inhibiting activity of polypeptide Q19K of the present invention obtained in Example 6-(5).
FIG. 27 shows a nucleotide sequence (SEQ ID NO: 94) of antisense primer, p-a06.

In the same way, FXa-inhibiting activity of the purified product obtained in Example 6-(5) was compared to that of the purified product obtained in Example 1-(5). As shown in FIG. 26, the polypeptide Q19K of the present invention obtained in Example 6-(4) showed about 5 times higher human FXa-inhibiting activity than that of the polypeptides TN70 obtained in Example 1-(5).

Example 8

Safety

Acute toxicity tests were carried out using one-week-prebreeding Wistar rats, each test group including 10 males or females. Samples were prepared in the following manner.

*E. coli* JE5505 (pM552) was cultured in the same manner as described in Example 1-(4) and a purified vacuum-dried sample was prepared from the resulting culture supernatant in accordance with the procedure described in Example 1-(5).

*E. coli* JE5505 (pM560) was cultured in the same manner as described in Example 2-(4) and a purified vacuum-dried sample was prepared from the resulting culture supernatant in accordance with the procedure described in Example 2-(5).

E. coli JE5505 (pM551) was cultured in the same manner as described in Example 1-(4) and a purified vacuum-dried sample was prepared from the resulting culture supernatant in accordance with the procedure described in Example 1-(5).

*E. coli* JE5505 (pM575B) was cultured in the same manner as described in Example 1-(4) and a purified vacuum-dried sample was prepared from the resulting culture supernatant in accordance with the procedure described in Example 5-(4).

*E. coli* JE5505 (pM576) was cultured in the same manner as described in Example 2-(4) and a purified vacuum-dried sample was prepared from the resulting culture supernatant in accordance with the procedure described in Example 5-(4).

Each of the thus prepared five purified samples was dissolved in physiological saline and the resulting solution was applied to a Pyrosart unit (molecular weight cutoff of 20,000, Sartorius) in order to remove LPS. Each of the resulting samples was administered to rats of each test group by intravenous injection with a dose of 300 mg/kg/day, and appearance of symptoms and changes in their body weights were observed for one week. Physiological saline was administered to the control group.

None of the samples showed a baneful effect in terms of a difference in the body weight between the test and control groups during the observation period. Also, neither a significant side effect nor death was found.

Example 9

Preparation of pharmaceutical preparations

Pharmaceutical preparations were prepared in the following manner.

*E. coli* JE5505 (pM552) was cultured in the same manner as described in Example 1-(4) and the product of interest was purified from the resulting culture supernatant in accordance with the procedure described in Example 1-(5). The purified product was then applied to the aforementioned Pyrosart unit (molecular weight cutoff of 20,000) in order to remove LPS, and the resulting sample was dried under a reduced pressure.

*E. coli* JE5505 (pM560) was cultured in the same manner as described in Example 2-(4) and the product of interest was purified from the resulting culture supernatant in accordance with the procedure described in Example 2-(5). After removing LPS, the purified product was dried under a reduced pressure.

*E. coli* JE5505 (pM551) was cultured in the same manner as described in Example 1-(4) and the product of interest was purified from the resulting culture supernatant in accordance with the procedure described in Example 1-(5). After removing LPS, the purified product was dried under a reduced pressure.

*E. coli* JE5505 (pM575B) was cultured in the same manner as described in Example 1-(4) and the product of interest was purified from the resulting culture supernatant in accordance with the procedure described in Example 5-(4). After removing LPS, the purified product was dried under a reduced pressure.

*E. coli* JE5505 (pM576) was cultured in the same manner as described in Example 2-(4) and the product of interest was purified from the resulting culture supernatant in accordance with the procedure described in Example 5-(4). After removing LPS, the purified product was dried under a reduced pressure.

Each of the thus purified and vacuum-dried five samples was dissolved in pyrogen-free 1/15M phosphate buffer (pH 7.4) containing 0.1% (w/v) gelatin. To the resulting solution of each sample (final concentration, 5 mg/ml) were added sodium chloride to a final concentration of 75 mM and then mannitol to a final concentration of 2% (w/v). The prepared sample solution was sterilized by filtration through an aseptic 0.22-μm membrane filter (Disposable Sterile Filter System, CORNING Inc.) and dispensed in 5 ml aliquots into glass tubes. Thereafter, the thus dispensed samples were frozen and then lyophilized using a freeze dryer to obtain lyophilized pharmaceutical preparations.

Reference Example 1

A polypeptide defined by an amino acid sequence of the following formula 16 was prepared and its enzyme inhibition activities were measured. The amino acid sequence represented by the formula 16 corresponds to the aforementioned amino acid sequence of formula 3 except that amino acids from the 55th Cys to the 70th Asn, counted from its N-terminus are deleted.

Formula 16 (SEQ ID NO: 16)
Thr Val Ala Ala Cys Asn Leu Pro Ile Val Arg Gly Pro
Cys Arg Ala Phe Ile Gln Leu Trp Ala Phe Asp Ala Val
Lys Gly Lys Cys Val Leu Phe Pro Tyr Gly Gly Cys Gln
Gly Asn Gly Asn Lys Phe Tyr Ser Glu Lys Glu Cys Arg
Glu Tyr (1) DNA cloning and expression vector construction Cloning of a DNA fragment encoding the amino acid sequence of the above formula 16 was carried out by site-directed mutagenesis according to the procedure of Example 2-(2) using plasmid pM552 obtained in Example 1-(3) as a material.

An ssDNA fragment was prepared from M13 phage obtained in Example 2-(1), and PCR was carried out according to the procedure of Example 2-(1) using the thus prepared ssDNA fragment as a template. In this instance, HindIII sense primer (FIG. 9A) prepared in Example 2-(2) was used. As an antisense primer, p-a06 (SEQ ID NO: 94) (FIG. 27) was synthesized using the aforementioned chemical synthesizer and purified making use of the aforementioned OPC column. The thus amplified product was double-digested with HindIII and BamHI and then extracted with phenol and purified by ethanol precipitation. In similar protocol of Example 2-(3), the purified product was inserted into plasmid pM463 to construct plasmid pM564. A DNA sequence of a region of the thus obtained plasmid pM564 from its HindIII recognition site to BamHI site containing the DNA fragment of interest, which has been confirmed using the aforementioned DNA sequencer, is shown in FIG. 28 together with its encoded amino acid sequence (SEQ ID NOS: 95 and 96).

(2) Preparation and cultivation of transformant

An *E. coli* strain JE5505 was transformed with the expression plasmid pM564 prepared in the above procedure (1) in accordance with the method of Hanahan to obtain *E. coli* JE5505 (pM564). The thus obtained *E. coli* JE5505 (pM564) was cultured in the same protocol as in Example 2-(4), and the resulting culture supernatant was prepared by centrifugation. The culture supernatant was diluted to each level of predetermined concentration with 0.1% BSA/0.2M triethanolamine-HCl buffer (pH 7.8), and the diluted sample was assayed for its trypsin-inhibiting activity according to the procedure of Example 4-(1). Separately from this, the culture supernatant was diluted to various concentrations with 0.1% BSA/150 mM NaCl/5 mM CaCl$_2$/50 mM tris-HCl buffer (pH 8.3), and each of the diluted samples was assayed for its FXa-inhibiting activity according to the procedure of Example 4-(5). Similar to the case of Example 2-(4), a culture supernatant of *E. coli* JE5505 (pM463C) was used as a control.

As the results, trypsin- or FXa-inhibiting activity was not found in these culture supernatant.

Reference Example 2

A polypeptide defined by an amino acid sequence of the following formula 17 was prepared and its enzyme inhibition activities were measured. The amino acid sequence represented by the formula 17 corresponds to the aforementioned amino acid sequence of formula 3 except that amino acids from the 1st (Thr) to the 5th (Cys) and the 57th Val and following amino acids, counted from its N-terminus, are deleted.

Formula 17 (SEQ ID NO: 17)
Asn Leu Pro Ile Val Arg Gly Pro Cys Arg Ala Phe Ile
Gln Leu Trp Ala Phe Asp Ala Val Lys Gly Lys Cys Val
Leu Phe Pro Tyr Gly Gly Cys Gln Gly Asn Gly Asn Lys
Phe Tyr Ser Glu Lys Glu Cys Arg Glu Tyr Cys Gly (1) Preparation of plasmid pM562

Plasmid pM562 to be used as a template of PCR in the next step (2) was prepared according to the procedure of Example 2-(1) using plasmid pM552 obtained in Example 1-(2). The plasmid pM562 contains a DNA fragment which encodes a portion of the amino acid sequence of the aforementioned formula 3 from its N-terminus amino acid to the 56th amino acid.

Firstly, an ssDNA fragment was prepared from M13 phage obtained in Example 2-(1), and PCR was carried out according to the procedure of Example 2-(1) using the thus prepared ssDNA fragment as a template. In this instance, ScaI sense primer (FIG. 8A) prepared in Example 2-(1) was used. As an antisense primer, p-a07 (SEQ ID NO: 97) (FIG. 29) was synthesized chemically and purified. The thus amplified product was incorporated into plasmid pM469 in the same protocol as in Example 5-(2) to obtain plasmid pM562.

(2) Cloning of DNA

A DNA fragment encoding the amino acid sequence of the above formula 17 was obtained by site-directed mutagenesis according to the procedure of Example 2-(2) using plasmid pM562 obtained in the above step (1) as a template for PCR use.

Firstly, a sense primer p-s02 (SEQ ID NO: 98) (FIG. 30) was chemically synthesized and purified for use in a primary PCR. The primary PCR was carried out in accordance with the procedure of Example 2-(2) using the sense primer p-s02 thus obtained, a BamHI antisense primer (SEQ ID NO: 81) (FIG. 9C) obtained in Example 2-(2) and the plasmid pM562 obtained in the above step (1) as a template. After completion of the primary PCR, a portion of the reaction mixture was applied to 1.5% agarose gel electrophoresis to confirm formation of the amplified product of interest having a size of about 220 bp. Thereafter, the product was extracted, purified and then dissolved in TE buffer.

Next, a secondary PCR was carried out using the thus amplified product as an antisense primer and the plasmid pM562 as a template similar to the case of the primary PCR. In this instance, a HindIII sense primer (SEQ ID NO: 79) (FIG. 9A) obtained in Example 2-(2) was used.

(3) Construction of expression plasmid

After completion of the secondary PCR, a portion of the reaction mixture was applied to 1.5% agarose gel electrophoresis to confirm formation of the amplified product of interest having a size of about 290 bp.

The thus amplified product was double-digested with HindIII and BamHI and then extracted with phenol and purified by ethanol precipitation. In similar protocol of Example 2-(3), the purified product was inserted into plasmid pM463 to construct plasmid pM567. A DNA sequence of a region of the thus obtained plasmid pM567 from its HindIII recognition site to BamHI site containing the DNA fragment of interest, which has been confirmed using the aforementioned DNA sequencer, is shown in FIG. 31 together with its corresponding amino acid sequence (SEQ ID NOS: 99 and 100).

(4) Preparation and cultivation of transformant

An *E. coli* strain JE5505 was transformed with the plasmid pM567 prepared in the above procedure (1) in accordance with the method of Hanahan to obtain *E. coli* JE5505 (pM567). The thus obtained *E. coli* JE5505 (pM567) was cultured in the same protocol as in Example 2-(4), and the resulting culture supernatant was prepared by centrifugation. The culture supernatant was diluted to each level of predetermined concentration with 0.1% BSA/0.2M triethanolamine-HCl buffer (pH 7.8), and the diluted sample was assayed for its trypsin-inhibiting activity according to the procedure of Example 4-(1). Separately from this, the culture supernatant was diluted to various concentrations with 0.1% BSA/150 mM NaCl/5 mM CaCl$_2$/50 mM tris-HCl buffer (pH 8.3), and each of the diluted samples was assayed for its FXa-inhibiting activity according to the procedure of Example 4-(5). Similar to the case of Example 2-(4), a culture supernatant of *E. coli* JE5505 (pM463C) was used as a control.

As the results, trypsin- or FXa-inhibiting activity was not found in these culture supernatant.

Reference Example 3

A polypeptide defined by an amino acid sequence of the following formula 18 was prepared and its enzyme inhibition activities were measured. The amino acid sequence represented by the formula 18 corresponds to the aforementioned amino acid sequence of formula 3 except that the 38th Cys from its N-terminus is substituted by Ser.

Formula 18 (SEQ ID NO: 18)
Thr Val Ala Ala Cys Asn Leu Pro Ile Val Arg Gly Pro
Cys Arg Ala Phe Ile Gln Leu Trp Ala Phe Asp Ala Val
Lys Gly Lys Cys Val Leu Phe Pro Tyr Gly Gly Ser Gln
Gly Asn Gly Asn Lys Phe Tyr Ser Glu Lys Glu Cys Arg
Glu Tyr Cys Gly Val Pro Gly Asp Gly Asp Glu Glu Leu
Leu Arg Phe Ser Asn (1) DNA cloning and expression vector construction Cloning of a DNA fragment encoding the amino acid sequence of the above formula 18 was carried out by site-directed mutagenesis according to the procedure of Example 2-(2) using plasmid pM552 obtained in Example 1-(3) as a template.

Figure 32:
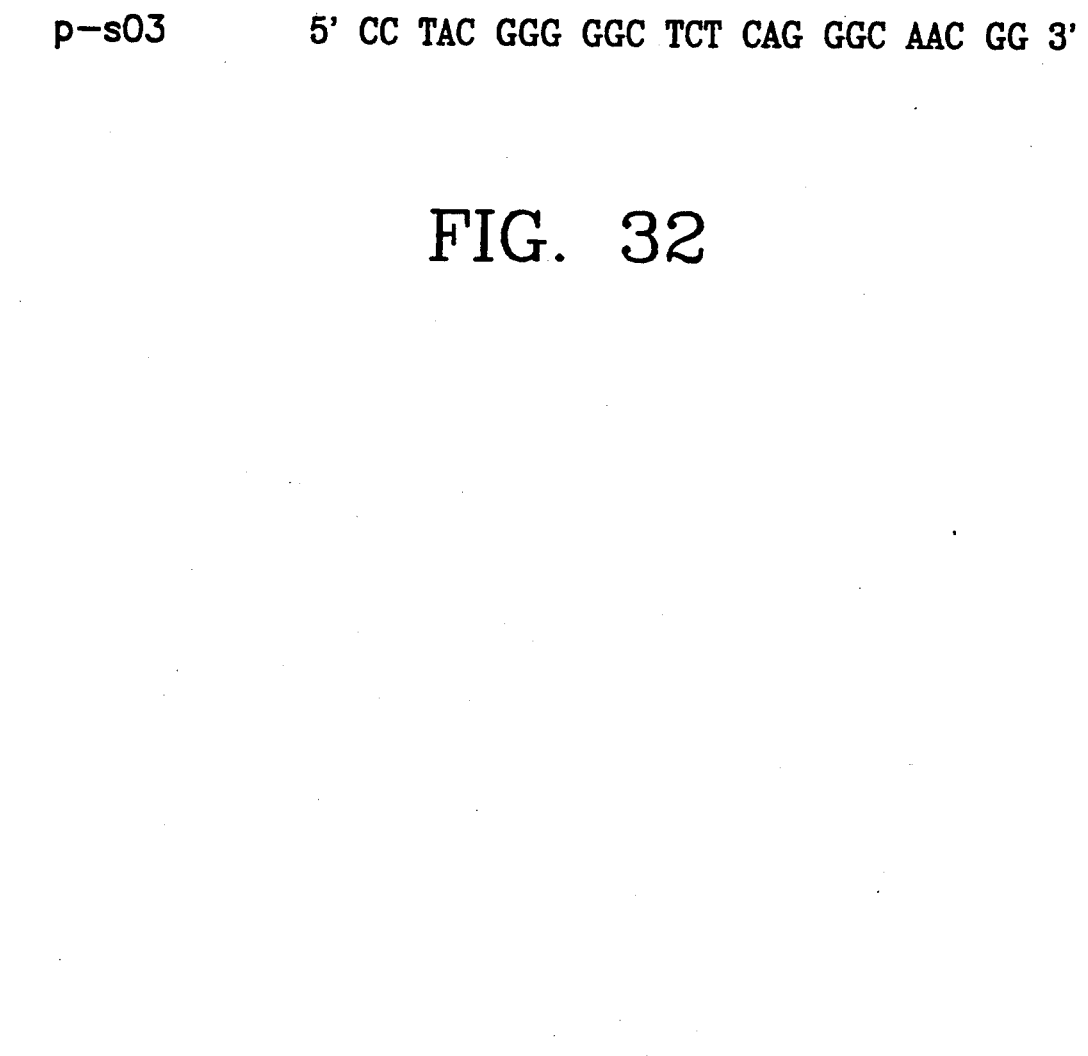

Firstly, a sense primer p-s03 (SEQ ID NO: 101) (FIG. 32) was prepared for use in a primary PCR. The primary PCR was carried out in accordance with the procedure of Example 2-(2) using the sense primer p-s03 thus obtained, a BamHI antisense primer (SEQ ID NO: 81) (FIG. 9C) obtained in Example 2-(2) and the plasmid pM552 as a template. After completion of the primary PCR, the thus amplified product containing about 140 bp fragment was extracted, purified and then dissolved in TE buffer.

Next, a secondary PCR was carried out using the thus amplified product as an antisense primer and the plasmid pM552 as a template similar to the case of the primary PCR. In this instance, a HindIII sense primer (SEQ ID NO: 79) (FIG. 9A) obtained in Example 2-(2) was used. The amplified product was double-digested with HindIII and BamHI and then extracted with phenol and purified by ethanol precipitation. In similar manner to the procedure of Example 2-(3), the thus purified amplified product was inserted into plasmid pM463 to construct plasmid pM568. A DNA sequence of a region of the thus obtained plasmid pM568 from its HindIII recognition site to BamHI site containing the DNA fragment of interest, which has been confirmed using the aforementioned DNA sequencer, is shown in FIG. 33 together with its encoded amino acid sequence (SEQ ID NOS: 102 and 103).

(2) Preparation and cultivation of transformant

An *E. coli* strain JE5505 was transformed with the expression plasmid pM568 prepared in the above procedure (1) in accordance with the method of Hanahan to obtain *E. coli* JE5505 (pM568). The thus obtained *E. coli* JE5505 (pM568) was cultured in the same protocol of Example 2-(4), and the resulting culture supernatant was prepared by centrifugation. The culture supernatant was diluted to each level of predetermined concentration with 0.1% BSA/0.2M triethanolamine-HCl buffer (pH 7.8), and the diluted sample was assayed for its trypsin-inhibiting activity according to the procedure of Example 4-(1). Separately from this, the culture supernatant was diluted to various concentrations with 0.1% BSA/150 mM NaCl/5 mM CaCl$_2$/50 mM tris-HCl buffer (pH 8.3), and each of the diluted samples was assayed for its FXa-inhibiting activity according to the procedure of Example 4-(5). Similar to the case of Example 2-(4), a culture supernatant of *E. coli* JE5505 (pM463C) was used as a control.

As the results, trypsin- or FXa-inhibiting activity was not found in these culture supernatant.

Reference Example 4

A polypeptide defined by an amino acid sequence of the following formula 19 was prepared and its enzyme inhibition activities were measured. The amino acid sequence represented by the formula 19 corresponds to the aforementioned amino acid sequence of formula 3 except that the 51st Cys from its N-terminus is substituted by Ser.

Thr Val Ala Ala Cys Asn Leu Pro Ile Val Arg Gly Pro
Cys Arg Ala Phe Ile Gln Leu Trp Ala Phe Asp Ala Val
Lys Gly Lys Cys Val Leu Phe Pro Tyr Gly Gly Cys Gln
Gly Asn Gly Asn Lys Phe Tyr Ser Glu Lys Glu Ser Arg

-continued

Glu Tyr Cys Gly Val Pro Gly Asp Gly Asp Glu Glu Leu
Leu Arg Phe Ser Asn (1) DNA cloning Cloning of a DNA fragment encoding the amino acid sequence of the above formula 19 was carried out by site-directed mutagenesis according to the procedure of Example 2-(2) using plasmid pM552 obtained in Example 1-(3) as a template.

Figure 34:
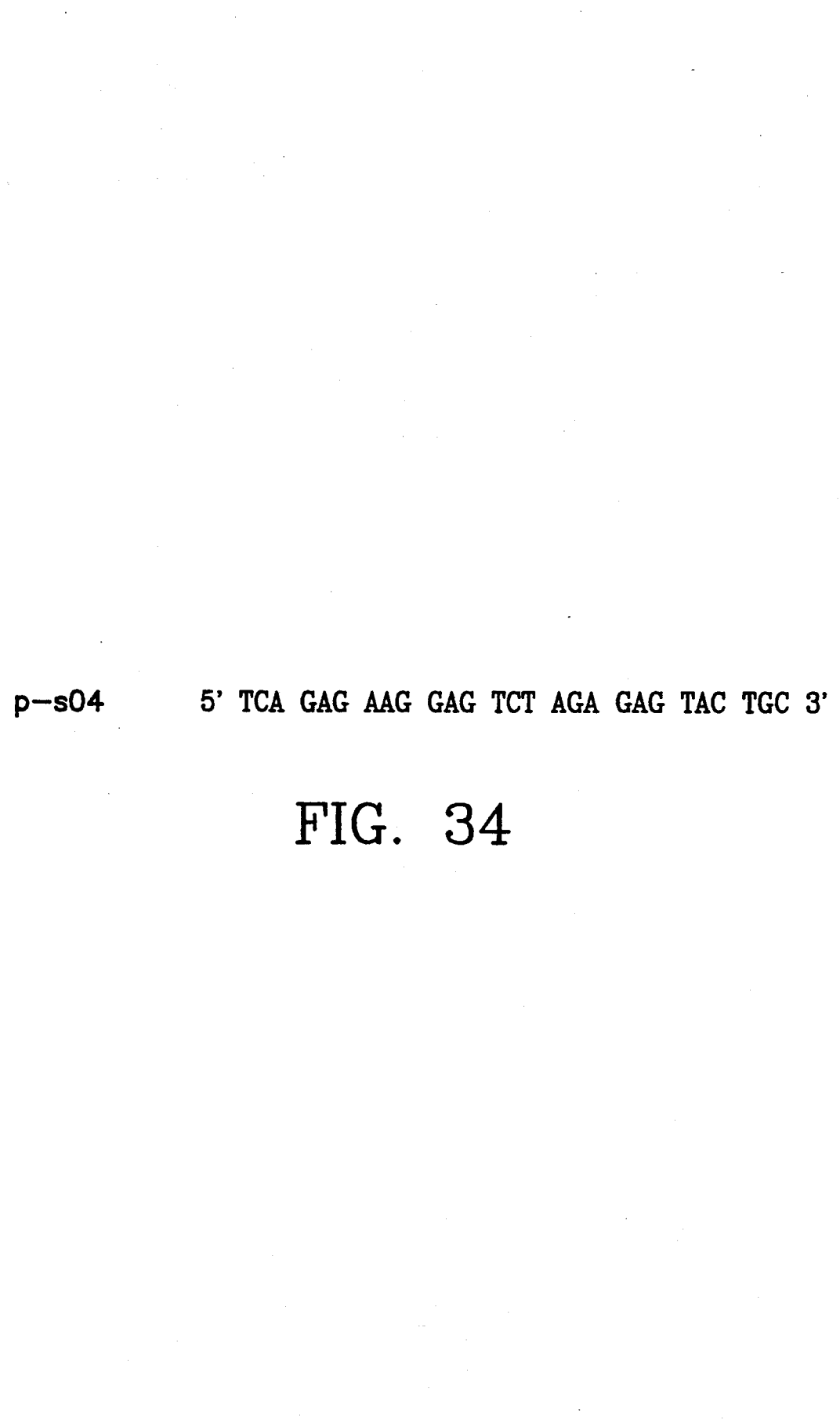

Firstly, a sense primer p-s04 (SEQ ID NO: 104) (FIG. 34) was prepared for use in a primary PCR. The primary PCR was carried out in accordance with the procedure of Example 2-(2) using the sense primer p-s04 thus obtained, a BamHI antisense primer (SEQ ID NO: 81) (FIG. 9C) obtained in Example 2-(2) and the plasmid pM552 as a template. After completion of the primary PCR, the thus amplified product containing about 140 bp fragment was extracted, purified and then dissolved in TE buffer.

Next, a secondary PCR was carried out using the thus amplified product as an antisense primer and the plasmid pM552 as a template similar to the case of the primary PCR. In this instance, a HindIII sense primer (SEQ ID NO: 79) (FIG. 9A) obtained in Example 2-(2) was used. The thus amplified product was double-digested with HindIII and BamHI and then extracted with phenol and purified by ethanol precipitation. In similar protocol of Example 2-(3), the thus purified amplified fragment was inserted into plasmid pM463 to construct plasmid pM569. A DNA sequence of a region of the thus obtained plasmid pM569 from its HindIII recognition site to BamHI site containing the DNA fragment of interest, which has been confirmed using the aforementioned DNA sequencer, is shown in FIG. 35 together with its encoded amino acid sequence (SEQ ID NOS: 105 and 106).

(2) Preparation and cultivation of transformant

An E. coli strain JE5505 was transformed with the expression plasmid pM569 prepared in the above procedure (1) in accordance with the method of Hanahan to obtain E. coli JE5505 (pM569). The thus obtained E. coli JE5505 (pM569) was cultured in the same manner as in Example 2-(4), and the resulting culture supernatant was prepared by centrifugation. The culture supernatant was diluted to each level of predetermined concentration with 0.1% BSA/0.2M triethanolamine-HCl buffer (pH 7.8), and the diluted sample was assayed for its trypsin-inhibiting activity according to the procedure of Example 4-(1). Separately from this, the culture supernatant was diluted to various concentrations with 0.1% BSA/150 mM NaCl/5 mM $CaCl_2$/50 mM tris-HCl buffer (pH 8.3), and each of the diluted samples was assayed for its FXa-inhibiting activity according to the procedure of Example 4-(5). Similar to the case of Example 2-(4), a culture supernatant of E. coli JE5505 (pM463C) was used as a control.

As the results, trypsin- or FXa-inhibiting activity was not found in these culture supernatant.

Thus, it is apparent that there have been provided, in accordance with the present invention, novel polypeptides having activities to inhibit various proteases, DNA fragments which encode the polypeptides, vectors containing the DNA fragments, transformants transformed with the DNA fragments or the vectors and processes for the production of the novel polypeptides. This invention also provides novel enzyme inhibition processes and novel drug compositions making use of the polypeptides.

Although some preferred embodiments have been described, many modifications and variations may be made thereto in the light of the above teachings. It is therefore to be understood that within the scope of the appended claims, the invention may be practiced otherwise than as specifically described.

What is claimed is:

1. An isolated protease inhibitor polypeptide, which consists of the following amino acid sequence SEQ ID NO: 2:

```
X1  Asn Leu Pro Ile Val Arg Gly Pro Cys Arg
Ala Phe Ile Gln Leu Trp Ala Phe Asp Ala Val
Lys Gly Lys Cys Val Leu Phe Pro Tyr Gly Gly
Cys Gln Gly Asn Gly Asn Lys Phe Tyr Ser Glu
Lys Glu Cys Arg Glu Tyr X2
``` wherein X1 is one amino acid sequence selected from the group consisting of the sequences (1) to (5) and (23):
  (1) Thr Val Ala Ala Cys SEQ ID NO: 20,
  (2) Val Ala Ala Cys SEQ ID NO: 21,
  (3) Ala Ala Cys,
  (4) Ala Cys,
  (5) Cys, and
  (23) Asp Asp Ala Ala Cys SEQ ID NO: 107;
X2 is one amino acid sequence selected from the group consisting of the sequences (6) to (21):
  (6) Cys Gly Val Pro Gly Asp Gly Asp Glu Glu Leu Leu Arg Phe Ser Asn SEQ ID NO: 25,
  (7) Cys Gly Val Pro Gly Asp Gly Asp Glu Glu Leu Leu Arg Phe Ser SEQ ID NO: 26,
  (8) Cys Gly Val Pro Gly Asp Gly Asp Glu Glu Leu Leu Arg Phe SEQ ID NO: 27,
  (9) Cys Gly Val Pro Gly Asp Gly Asp Glu Glu Leu Leu Arg SEQ ID NO: 28,
  (10) Cys Gly Val Pro Gly Asp Gly Asp Glu Glu Leu Leu SEQ ID NO: 29,
  (11) Cys Gly Val Pro Gly Asp Gly Asp Glu Glu Leu SEQ ID NO: 30,
  (12) Cys Gly Val Pro Gly Asp Gly Asp Glu Glu SEQ ID NO: 31,
  (13) Cys Gly Val Pro Gly Asp Gly Asp Glu SEQ ID NO: 32,
  (14) Cys Gly Val Pro Gly Asp Gly Asp SEQ ID NO: 33,
  (15) Cys Gly Val Pro Gly Asp Gly SEQ ID NO: 34,
  (16) Cys Gly Val Pro Gly Asp SEQ ID NO: 35,
  (17) Cys Gly Val Pro Gly SEQ ID NO: 36,
  (18) Cys Gly Val Pro SEQ ID NO: 37,
  (19) Cys Gly Val,
  (20) Cys Gly, and
  (21) Cys;
provided that X1 is not (1) when X2 is (6), (7), (8), (9) or (10).

2. The protease inhibitor polypeptide according to claim 1, wherein X1 is (3); and X2 is (6).

3. A pharmaceutical composition of matter for use in the prevention and/or treatment of a disorder involving at least one enzyme selected from the group consisting of trypsin, elastase, plasmin, plasma kallikrein, and activated blood coagulation factor X (FXa) in a patient, said composition comprising a pharmaceutically effective amount of the protease inhibitor polypeptide of claim 1 as its active ingredient, and a pharmaceutically acceptable carrier therefor.

4. A pharmaceutical composition of matter for use in the prevention and/or treatment of a disorder involving at least one enzyme selected from the group consisting of trypsin, elastase, plasmin, plasma kallikrein, and activated blood coagulation factor X (FXa) in a patient, said composition comprising a pharmaceutically effective amount of the protease inhibitor polypeptide of claim 2 as its active ingredient, and a pharmaceutically acceptable carrier therefor.

5. An isolated protease inhibitor polypeptide, which consists of the following amino acid sequence SEQ ID NO: 108:

```
X1  Asn Leu Pro   Ile Val Arg Gly Pro   Cys Arg
Ala Phe Ile Xaa-1 Leu Trp Ala Phe Asp   Ala Val
Lys Gly Lys Cys   Val Leu Phe Pro Tyr   Gly Gly
Cys Gln Gly Asn   Gly Asn Lys Phe Xaa-2 Ser Glu
Lys Glu Cys Arg   Glu Tyr X2
``` wherein X1 is one amino acid sequence selected from the group consisting of the sequences (1) to (5) and (23):
- (1) Thr Val Ala Ala Cys SEQ ID NO: 20,
- (2) Val Ala Ala Cys SEQ ID NO: 21,
- (3) Ala Ala Cys,
- (4) Ala Cys,
- (5) Cys, and
- (23) Asp Asp Ala Ala Cys SEQ ID NO: 107;

X2 is one amino acid sequence selected from the group consisting of the sequences (6) to (21):
- (6) Cys Gly Val Pro Gly Asp Gly Asp Glu Glu Leu Leu Arg Phe Ser Asn SEQ ID NO: 25,
- (7) Cys Gly Val Pro Gly Asp Gly Asp Glu Glu Leu Leu Arg Phe Ser SEQ ID NO: 26,
- (8) Cys Gly Val Pro Gly Asp Gly Asp Glu Glu Leu Leu Arg Phe SEQ ID NO: 27,
- (9) Cys Gly Val Pro Gly Asp Gly Asp Glu Glu Leu Leu Arg SEQ ID NO: 28,
- (10) Cys Gly Val Pro Gly Asp Gly Asp Glu Glu Leu Leu SEQ ID NO: 29,
- (11) Cys Gly Val Pro Gly Asp Gly Asp Glu Glu Leu SEQ ID NO: 30,
- (12) Cys Gly Val Pro Gly Asp Gly Asp Glu Glu SEQ ID NO: 31,
- (13) Cys Gly Val Pro Gly Asp Gly Asp Glu SEQ ID NO: 32,
- (14) Cys Gly Val Pro Gly Asp Gly Asp SEQ ID NO: 33,
- (15) Cys Gly Val Pro Gly Asp Gly SEQ ID NO: 34,
- (16) Cys Gly Val Pro Gly Asp SEQ ID NO: 35,
- (17) Cys Gly Val Pro Gly SEQ ID NO: 36,
- (18) Cys Gly Val Pro SEQ ID NO: 37,
- (19) Cys Gly Val,
- (20) Cys Gly, and
- (21) Cys;

wherein Xaa-1 is Gln and Xaa-2 is Glu or Xaa-1 is Lys and Xaa-2 is Tyr.

6. The protease inhibitor polypeptide according to claim 5, wherein X1 is (1); X2 is (6); and Xaa-1 is Gln and Xaa-2 is Glu.

7. The protease inhibitor polypeptide according to claim 5, wherein X1 is (23); X2 is (6); and Xaa-1 is Lys and Xaa-2 is Tyr.

8. A pharmaceutical composition of matter for use in the prevention and/or treatment of a disorder involving at least one enzyme selected from the group consisting of trypsin, elastase, plasmin, plasma kallikrein, and activated blood coagulation factor X (FXa) in a patient, said composition comprising a pharmaceutically effective amount of the protease inhibitor polypeptide of claim 5 as its active ingredient, and a pharmaceutically acceptable carrier therefor.

9. A pharmaceutical composition of matter for use in the prevention and/or treatment of a disorder involving at least one enzyme selected from the group consisting of trypsin, elastase, plasmin, plasma kallikrein, and activated blood coagulation factor X (FXa) in a patient, said composition comprising a pharmaceutically effective amount of the protease inhibitor polypeptide of claim 6 as its active ingredient, and a pharmaceutically acceptable carrier therefor.

10. A pharmaceutical composition of matter for use in the prevention and/or treatment of a disorder involving at least one enzyme selected from the group consisting of trypsin, elastase, plasmin, plasma kallikrein, and activated blood coagulation factor X (FXa) in a patient, said composition comprising a pharmaceutically effective amount of the protease inhibitor polypeptide of claim 7 as its active ingredient, and a pharmaceutically acceptable carrier therefor.

* * * * *